United States Patent
Kotov et al.

(10) Patent No.: US 9,922,746 B2
(45) Date of Patent: Mar. 20, 2018

(54) STRETCHABLE COMPOSITE CONDUCTORS FOR FLEXIBLE ELECTRONICS, STRETCHABLE PLASMONIC DEVICES, OPTICAL FILTERS, AND IMPLANTABLE DEVICES AND METHODS FOR MANUFACTURE THEREOF

(71) Applicant: The Regents of the University of Michigan, Ann Arbor, MI (US)

(72) Inventors: Nicholas A. Kotov, Ypsilanti, MI (US); Yoonseob Kim, Ann Arbor, MI (US); Jian Zhu, Ann Arbor, MI (US); Matthew Di Prima, Bowie, MD (US); Bongjun Yeom, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 542 days.

(21) Appl. No.: 14/193,837

(22) Filed: Feb. 28, 2014

(65) Prior Publication Data
US 2014/0249526 A1    Sep. 4, 2014

Related U.S. Application Data

(60) Provisional application No. 61/771,398, filed on Mar. 1, 2013.

(51) Int. Cl.
*H01B 1/22* (2006.01)
*A61L 29/12* (2006.01)
(Continued)

(52) U.S. Cl.
CPC .......... *H01B 1/22* (2013.01); *A61B 18/1492* (2013.01); *A61L 29/126* (2013.01); *A61L 29/14* (2013.01);
(Continued)

(58) Field of Classification Search
CPC ... H01B 1/20; H01B 1/22; H01B 1/24; H01B 13/008; H05K 1/095; H05K 1/097;
(Continued)

(56) References Cited

U.S. PATENT DOCUMENTS

| 6,107,699 A * | 8/2000 | Swanson | A61B 18/1492 |
| | | | 307/112 |
| 6,123,718 A * | 9/2000 | Tu | A61B 18/1492 |
| | | | 606/41 |

(Continued)

OTHER PUBLICATIONS

Johnson, P. B., et al., "Optical Constants of the Noble Metals," Physical Review B, vol. 6, No. 12, pp. 4370-4379 (Dec. 15, 1972).
(Continued)

*Primary Examiner* — Harold Pyon
*Assistant Examiner* — Matthew R Diaz
(74) *Attorney, Agent, or Firm* — Harness, Dickey & Pierce, P.L.C.

(57) ABSTRACT

New stretchable electrically conductive composite materials comprising at least one polymer and a plurality of nanoparticles are provided, which exhibit high conductivity even at high strain levels. The composite may comprise polyurethane as the polymer and spherical gold nanoparticles. Such materials have conductivity levels as high as 11,000 Scm$^{-1}$ at 0% strain and 2,400 Scm$^{-1}$ at 110% strain. Furthermore, certain embodiments of the composite have a maximum tensile strain of 480% while still exhibiting conductivity of 35 Scm$^{-1}$. The inventive materials are highly flexible, highly conductive and suitable for a variety of applications, especially for advanced medical devices, implants, and flexible electronics. The disclosure also provides methods of making such stretchable electrically conductive nanocomposites, including formation by layer-by-layer and vacuum assisted flocculation. In certain embodiments, stretchable chiral plasmonic composite materials for use as optic devices and methods for making them are provided.

28 Claims, 33 Drawing Sheets

(51) Int. Cl.
*A61L 29/14* (2006.01)
*A61L 31/12* (2006.01)
*A61L 31/14* (2006.01)
*A61B 18/14* (2006.01)
*A61B 18/00* (2006.01)

(52) U.S. Cl.
CPC ............ *A61L 31/125* (2013.01); *A61L 31/128* (2013.01); *A61L 31/14* (2013.01); *A61B 2018/0022* (2013.01); *A61B 2018/00577* (2013.01); *A61L 2400/12* (2013.01); *Y10T 428/24628* (2015.01); *Y10T 428/31554* (2015.04)

(58) Field of Classification Search
CPC ........ C08L 75/04–75/16; A61L 29/126; A61L 29/14; A61L 29/146; A61L 31/12; A61L 31/121; A61L 31/125; A61L 31/126; A61L 31/127; A61L 31/128; A61L 31/129; A61M 2025/1075; A61M 2025/1088; A61M 25/10; A61B 17/12136; A61B 18/1492; A61B 2018/00071; A61B 2018/00077
USPC ................................ 252/512, 514, 502, 503
See application file for complete search history.

(56) References Cited

U.S. PATENT DOCUMENTS

| | | | |
|---|---|---|---|
| 7,557,367 B2 | 7/2009 | Rogers et al. | |
| 7,758,572 B2 * | 7/2010 | Weber ................... | A61L 29/126 604/103.06 |
| 7,763,574 B2 | 7/2010 | Donnelly et al. | |
| 8,198,621 B2 | 6/2012 | Rogers et al. | |
| 2008/0086073 A1 * | 4/2008 | McDaniel .......... | A61B 18/1492 604/22 |
| 2009/0291608 A1 * | 11/2009 | Choi .................... | H05K 9/0015 442/394 |
| 2010/0179530 A1 * | 7/2010 | Long .................. | A61B 18/1206 606/33 |
| 2011/0160514 A1 * | 6/2011 | Long ..................... | A61B 18/02 600/2 |
| 2011/0256383 A1 * | 10/2011 | Cochet .................... | C08K 3/10 428/328 |
| 2012/0251824 A1 * | 10/2012 | Hur .......................... | H01B 1/02 428/378 |

OTHER PUBLICATIONS

Kim, Yoonseob, et al., "Elastic Conductors with Extreme Nanoparticle Content," Poster Presentation at Symposium CC: Hierarchically Self-assembled Materials—From Molecule to Nano and Beyond, 2012 Materials Research Society Spring Meeting & Exhibit, San Francisco, CA, Presentation CC3.24 (Apr. 10, 2012) (9 pages).

Kim, Yoonseob, et al., "Stretchable nanoparticle conductors with self-organized conductive pathways," Nature, vol. 500, pp. 59-63 (Aug. 1, 2013) (published online Jul. 17, 2013) and Supplementary Information (14 pages).

Lacour, Stéphanie Périchon, et al., "Stretchable gold conductors on elastomeric substrates," Applied Physics Letters, vol. 82, No. 15, pp. 2404-2406 (Apr. 14, 2003).

Turkevich, John, et al., "A Study of the Nucleation and Growth Processes in the Synthesis of Colloidal Gold," Discuss. Faraday Soc., vol. 11, pp. 55-75 (Jan. 1, 1951).

* cited by examiner

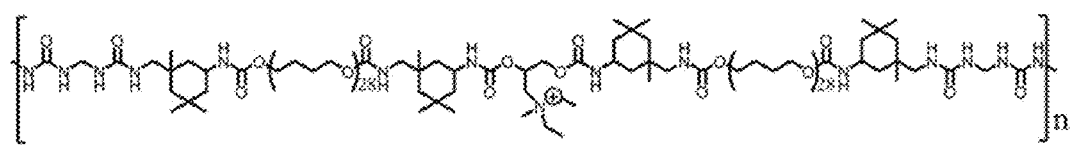
FIG. 2A
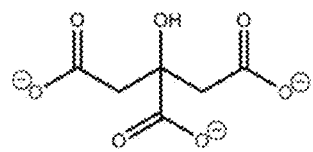
FIG. 2B
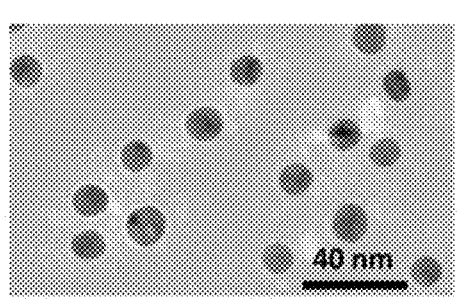 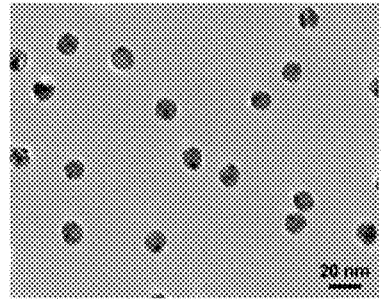
FIG. 3A    FIG. 3B

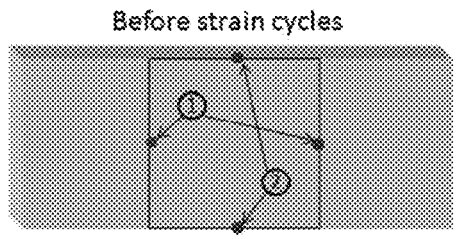
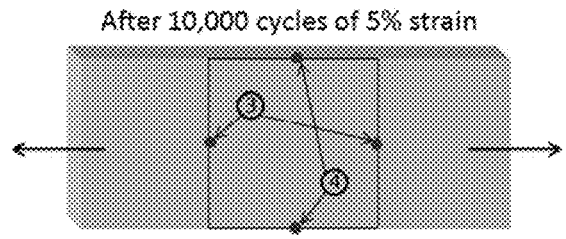
FIG. 10A  FIG. 10B
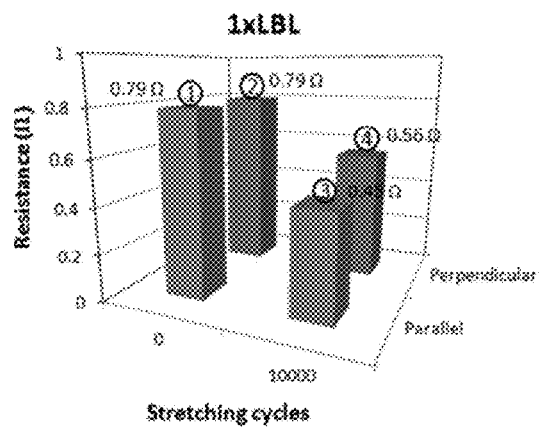
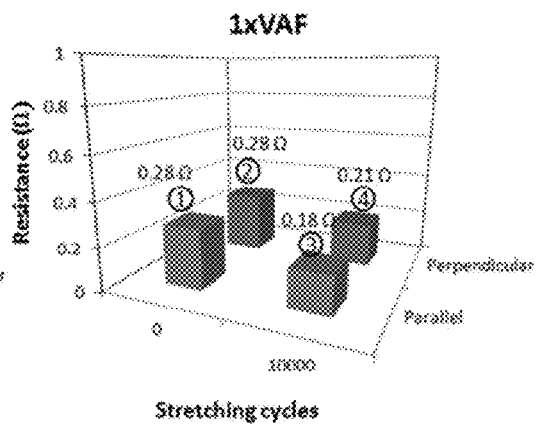
FIG. 10C  FIG. 10D
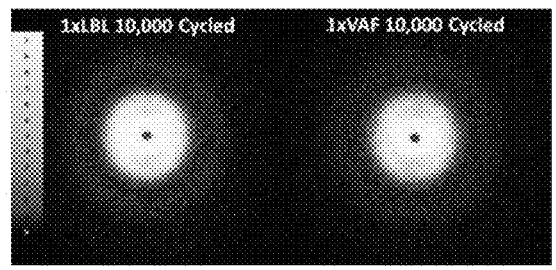
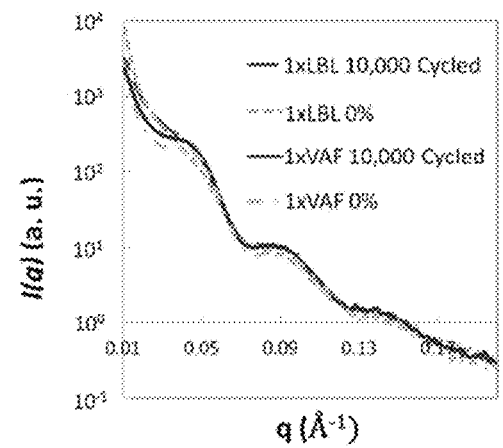
FIG. 10E  FIG. 10F

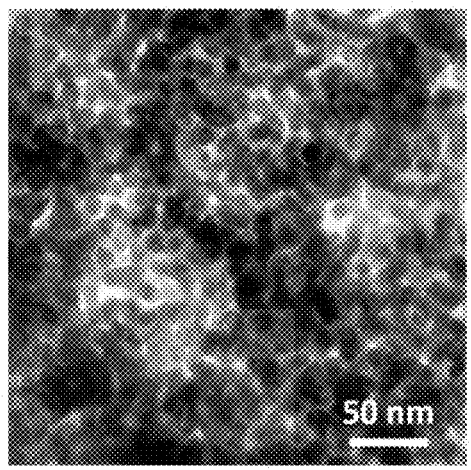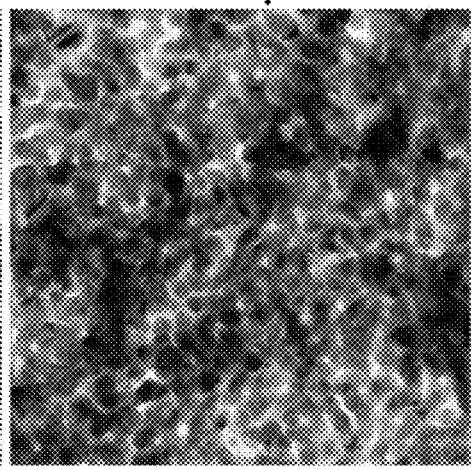
FIG. 12A  FIG. 12B
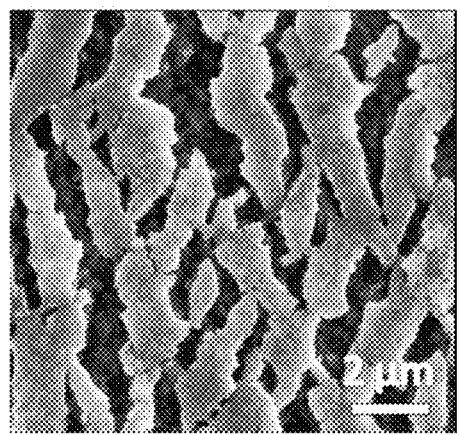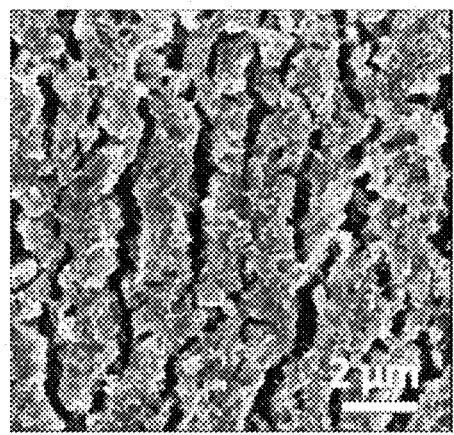
FIG. 13A  FIG. 13B

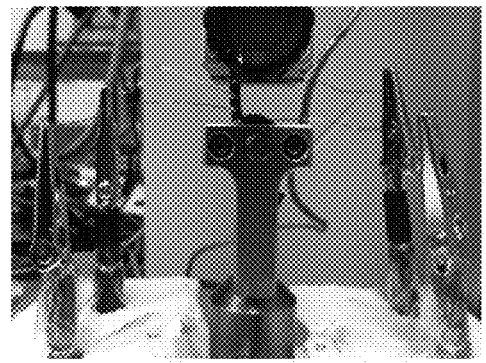
FIG. 17A
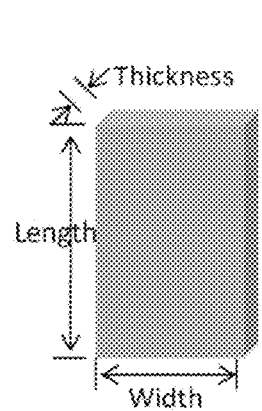  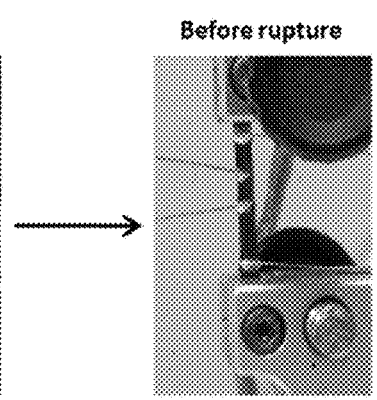 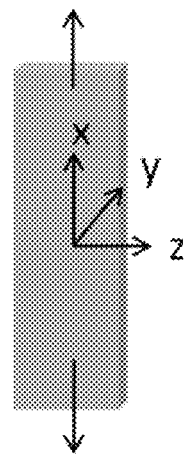
FIG. 17B    FIG. 17C         FIG. 17D    FIG. 17E stretched because interatomic bonds are not strong enough.

Best known stretchable conductors partially overcome these problems by using percolated networks of high aspect ratio nanotubes or nanowires. Such materials typically have electrical conductivity of about 10 Scm$^{-1}$ (or S/cm) and a maximum tensile strength ($\varepsilon_{max}$) of 100%. However, these materials suffer from issues such as relatively low electrical conductivity and/or loss of elasticity that occurs with high carbon nanotube loading. Advanced and performance-hungry devices, such as neuroprosthetic implants or stretchable displays, require materials having conductivities 10,000 times higher, e.g., approaching the conductivities in metals (10$^5$ Scm$^{-1}$), while retaining strains over 100%. Hence, realization of such devices thus far has been impeded by the lack of materials having the desired performance levels, which is in part due to the stretchability-conductivity dilemma. Accordingly, it would be desirable to develop highly stretchable electrically conductive materials that retain relatively high electrical conductivity even at high tensile strain levels. It would also be desirable to develop plasmonic materials based on stretchable materials having electric conductivity to provide plasmonic optical properties.

STRETCHABLE COMPOSITE CONDUCTORS FOR FLEXIBLE ELECTRONICS, STRETCHABLE PLASMONIC DEVICES, OPTICAL FILTERS, AND IMPLANTABLE DEVICES AND METHODS FOR MANUFACTURE THEREOF

CROSS-REFERENCE TO RELATED APPLICATIONS

This application claims the benefit of U.S. Provisional Application No. 61/771,398, filed on Mar. 1, 2013. The entire disclosure of the above application is incorporated herein by reference.

GOVERNMENT RIGHTS

This invention was made with government support under CBET1036672 awarded by the National Science Foundation and CA121841 awarded by the National Institutes of Health. The Government has certain rights in the invention.

FIELD

The present disclosure relates to stretchable conductors, and more specifically to stretchable, flexible electrically conductive composite materials and methods of making such materials for use in a variety of applications, including flexible electronics, stretchable electronics, stretchable plasmonic devices, plasmonic light filters, and implantable devices, by way of non-limiting example.

BACKGROUND

This section provides background information related to the present disclosure which is not necessarily prior art.

There is a strong interest in stretchable electrically conductive materials for use in a variety of diverse technological areas. Advanced implants and stretchable electronics require highly conductive materials that are elastic. For example, flexible electronics, neuroprosthetic and cardiostimulating implants, responsive curvilinear systems, advanced skins for robotics, and a variety of other applications require materials with increasingly high conductivity over increasingly large strains. However, while materials combining high stretchability and electrical conductivity are highly desirable, they are difficult to realize in practice. Molecular mechanisms of deformations and stiffening make combining high stretchability and conductivity fundamentally difficult.

Macroscale stretching of solids causes elongation and bending of chemical bonds. Such deformations lead to reduced overlap and delocalization of electronic orbitals, as well as degeneration of conduction pathways required for electronic conduction. Thus, macroscale stretching of solid materials causes elongation and bending of chemical bonds that are needed for electrical conduction (due to the transport of electrons along orbitals), causing a reduction in electrical conductivity. As such, even for purposefully designed stretchable conductors, electrical conductivity in materials decreases precipitously at tensile strains ranging from 130-150%. Aside from deformable solids, the dilemma between conductivity and stretchability can also be exemplified in liquid metals. Liquid metals have high electrical conductivities and can flow, but cannot be stretched because they are held by weak interatomic bonds. Thus, for these materials, efficient electron transport pathways are retained upon large deformation of shape, but liquid metals cannot be stretched because interatomic bonds are not strong enough.

SUMMARY

This section provides a general summary of the disclosure and is not a comprehensive disclosure of its full scope or all of its features.

In certain variations, the present disclosure provides stretchable electrically conductive composite materials. For example, in one aspect, the disclosure provides a stretchable composite material comprising an elastic polymer with a strain equal to or exceeding 50% and a plurality of conductive nanoparticles. In certain variations, the stretchable composite material may be made from gold nanoparticles and exhibits an electrical conductivity of greater than or equal to about 500 Scm$^{-1}$ at a tensile strain of greater than or equal to about 50%.

In other aspects, the present disclosure provides a stretchable electrically conductive composite material that comprises a plurality of laminated layers. Each layer of the plurality comprises an elastic polymer and a plurality of conductive nanoparticles. The stretchable composite material exhibits an electrical conductivity of greater than or equal to about 1,700 Scm$^{-1}$ at a tensile strain of 0%, where a maximum tensile strain of the stretchable composite material is greater than or equal to about 10%.

In yet other aspects, the present disclosure provides methods for making stretchable electrically conductive composite materials. For example, in certain aspects, the disclosure provides a method for forming a stretchable electrically conductive composite material that comprises applying a first charged material having a first polarity to a substrate having a second polarity opposite to the first polarity. Then, a second charged material having the second polarity is applied over the first charged material in a layer-by-layer process. The first charged material and the second charged material are distinct from one another and selected from a polymer and a plurality of conductive nanoparticles. Next, the first charged material and the second charged material are removed from the substrate. Together, the removed first charged material and second charged material define at least one layer of a composite material that exhibits an electrical conductivity of greater than or equal to about 6,750 Scm$^{-1}$ at a tensile strain of greater than or equal to about 15%.

In yet another aspect, the present disclosure provides a method for making stretchable electrically conductive composite materials that comprises introducing a first charged material having a first polarity into a suspension comprising a second charged material having a second polarity opposite to the first polarity. The first charged material comprises a polymer and the second charged material comprises a plurality of nanoparticles. The introducing of the first charged material causes flocculation of moieties (out of the suspension). The flocculated moieties thus comprise the first charged material and the second charged material. Next, the flocculated moieties are filtered from the suspension. Finally, the flocculated moieties are dried. The dried filtered flocculated moieties together define at least one layer of a composite material that exhibits an electrical conductivity of greater than or equal to about 500 $Scm^{-1}$ at a tensile strain of greater than or equal to about 75%.

In other aspects, the present disclosure contemplates a stretchable chiral plasmonic material. The plasmonic material comprises a twisted film comprising an elastic polymer having a maximum strain of greater than or equal to about 50% and a plurality of nanoparticles dispersed in the elastic polymer. The twisted film has either a left-handed chirality or a right-handed chirality based on a rotational direction of the twisted film. Further, the twisted film is capable of reversibly transitioning from a first twisted state to a second relaxed state to control chiroptical properties of the stretchable composite chiral plasmonic material.

In certain other aspects, the present disclosure contemplates a method for forming a stretchable chiral plasmonic material comprising applying a first charged material having a first polarity to a twisted substrate having a second polarity opposite to the first polarity. The method further comprises applying a second charged material having the second polarity over the first charged material in a layer-by-layer process. The first charged material and the second charged material are distinct from one another and selected from a polymer and a plurality of nanoparticles. The method further comprises removing the first charged material and the second charged material from the twisted substrate. The first charged material and the second charged material together define a plasmonic film having a left-handed chirality or a right-handed chirality based on a rotational direction of the twisted substrate.

In yet other aspects, the disclosure contemplates a medical device comprising a stretchable electrically conductive composite material. The stretchable composite material comprises an elastic polymer with a strain equal to or exceeding 50% and a plurality of conductive nanoparticles. In certain variations, the stretchable electrically conductive composite material may be made from gold nanoparticles and exhibits an electrical conductivity of greater than or equal to about 500 $Scm^{-1}$ at a tensile strain of greater than or equal to about 50%. In certain aspects, the medical device may comprise an inflatable balloon, where the stretchable electrically conductive composite material is disposed on one or more regions of a surface of the inflatable balloon to serve as one or more electrodes.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 2A-2B show a chemical structure of a cationic polyurethane polymer (FIG. 2A) and an optional anionic citrate (FIG. 2B) for stabilizing gold nanoparticles for use in forming stretchable electrically conductive composite materials according to certain aspects of the present disclosure.

FIGS. 3A-3B show transmission electron microscopy (TEM) images of gold nanoparticles (Au NPs) for use in stretchable electrically conductive composite materials according to certain aspects of the present disclosure.

Figure 4A:
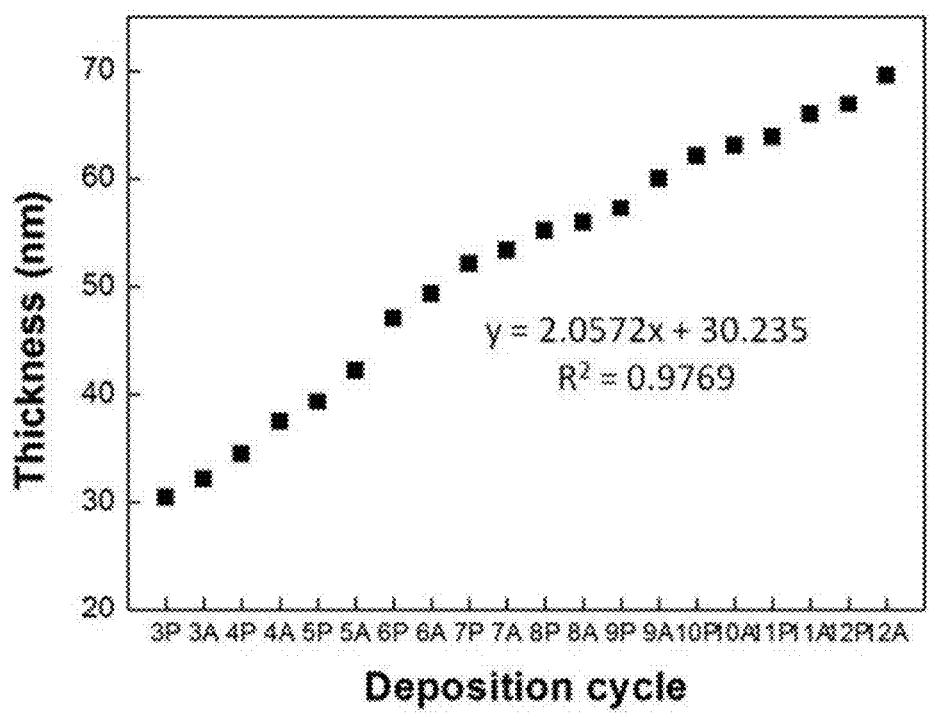
Figure 4B:
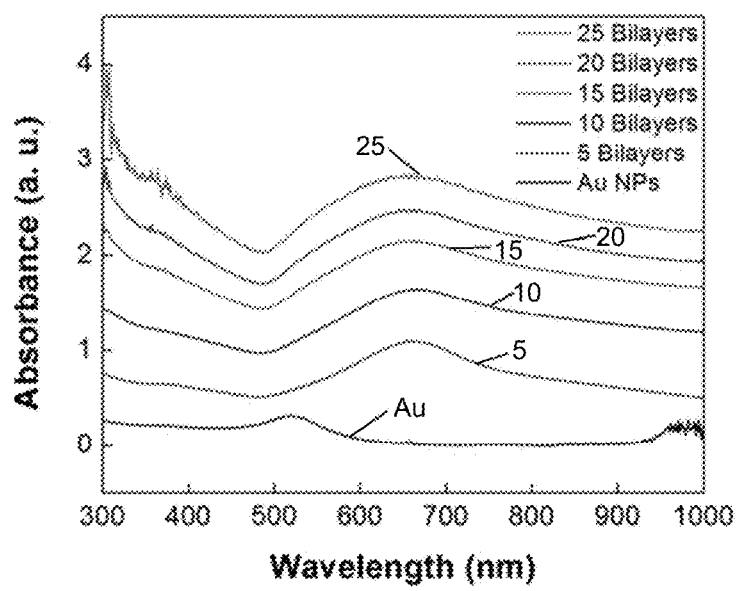

FIGS. 4A-4B. FIG. 4A shows dependence of thickness of films of stretchable electrically conductive composite materials comprising polyurethane (PU) polymer and gold nanoparticles (NP)–$(PU/NP)_n$ where n is number of deposition cycles each forming a distinct layer. PU (3P, 4P, 5P . . . ) and gold NPs (3A, 4A, 5A . . . ) layers with the same number correspond to one deposition cycle. Thickness change is measured by ellipsometry as the film is deposited via a layer-by-layer process on a silicon (Si) wafer as a substrate. Thickness of each layer is averaged based on three independent measurements. Average thickness increments for PU and Au NPs layers are 1.89 nm and 2.04 nm, respectively. FIG. 4B shows UV-Vis absorbance spectra measured at every fifth bilayer of $(PU/NP)_n$ LBL assemblies. The multilayers are formed on both sides of a glass substrate.

Figure 5:
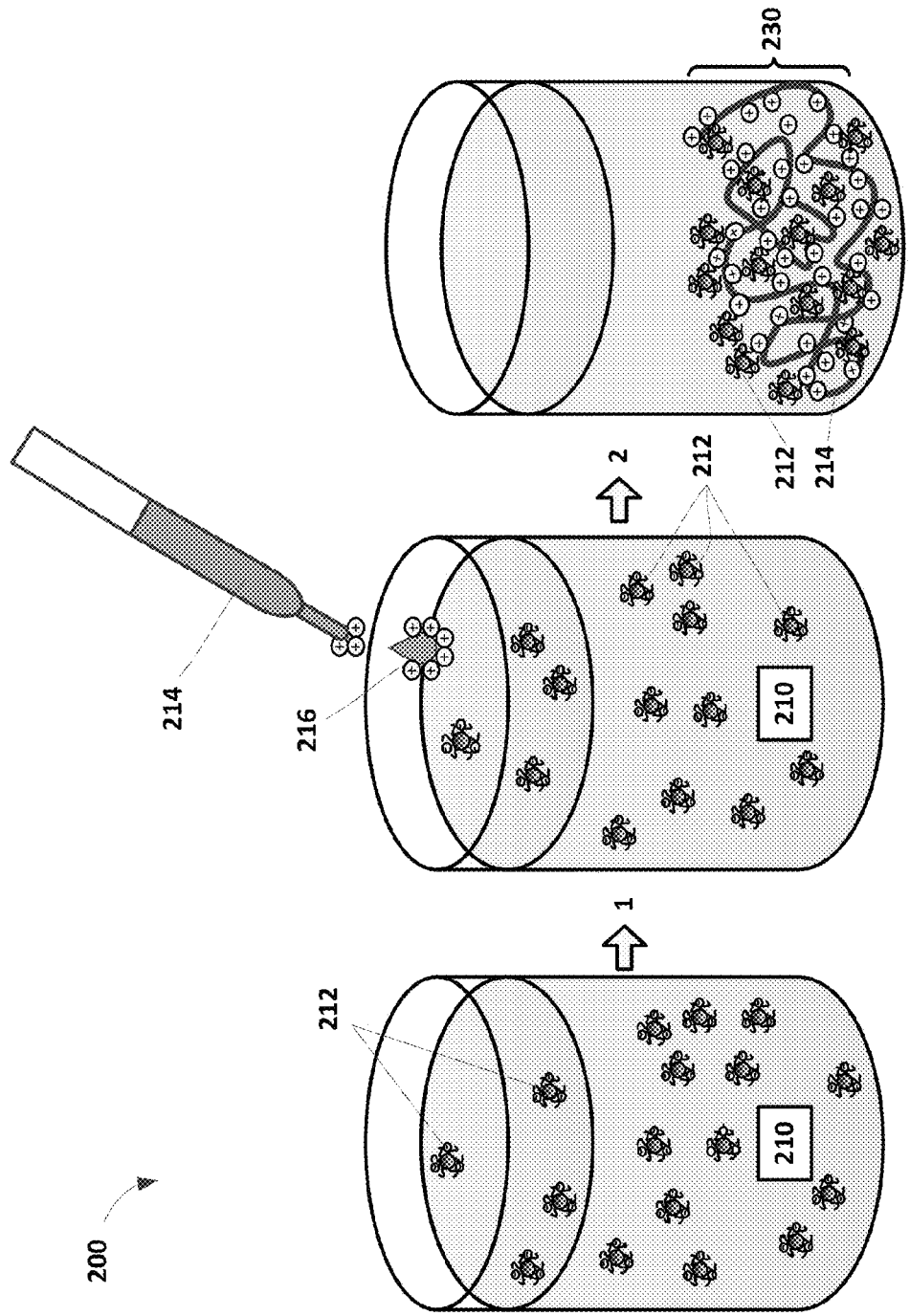

FIG. 5 shows an alternative method for forming a stretchable electrically conductive composite material via a vacuum assisted flocculation process according to certain aspects of the present disclosure.

Figures 6A, 6B, 6C, 6D:
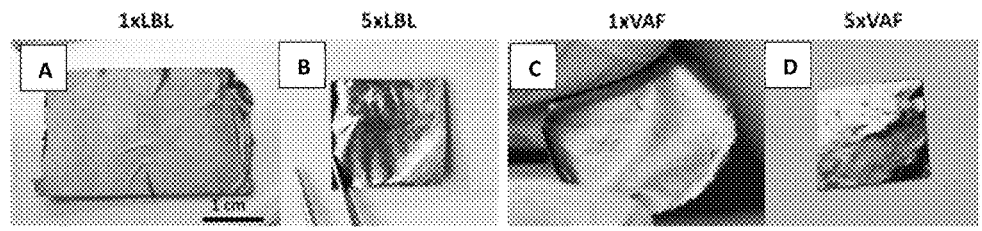
Figures 6E, 6F, 6G, 6H:
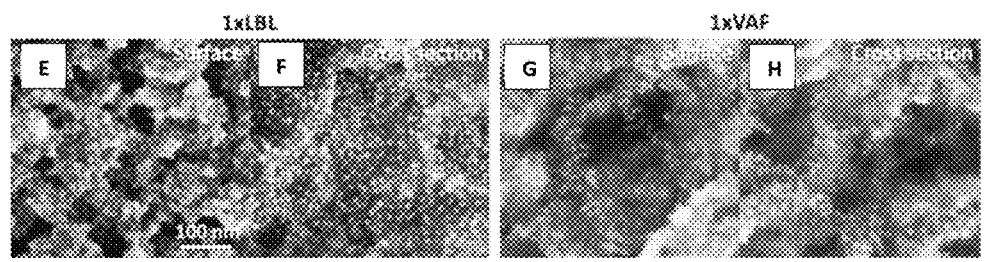
Figures 6I, 6J, 6K, 6L:
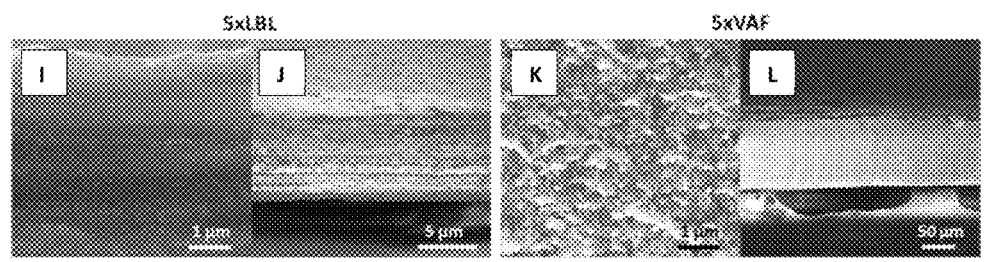

FIGS. 6A-6L. FIGS. 6A-6D show photographs of a free-standing single layer of film $(PU/NP)_{500}$ made in a layer-by-layer process (1×LBL) according to certain aspects of the present disclosure (FIG. 6A), a consolidated five layer (5×LBL) stack made in a layer-by-layer process according to certain aspects of the present disclosure (FIG. 6B), a free-standing single layer of film made by a vacuum assisted flocculation process (1×VAF) according to certain aspects of the present disclosure (FIG. 6C), and a consolidated five layer (5×VAF) stack made by a vacuum assisted flocculation process according to certain aspects of the present disclosure (FIG. 6D). FIGS. 6E-6H show scanning electron microscopy (SEM) images comparing a free-standing single layer of film made in a layer-by-layer process (1×LBL) according to certain aspects of the present disclosure and a free-standing single layer of film made by a vacuum assisted flocculation process (1×VAF) according to other aspects of the present disclosure. FIGS. 6E and 6G are taken on a surface of the 1×LBL film and 1×VAF film respectively (each having a scale bar of 100 nm), while FIGS. 6F and 6H are cross-sectional views of the 1×LBL film and 1×VAF film, respectively. FIGS. 6I-6L show SEM images of cross sections taken from a consolidated five layer (5×LBL) stack made in a layer-by-layer process according to certain aspects of the present disclosure (FIGS. 6I, 6J) and a consolidated five layer (5×VAF) stack made by a vacuum assisted flocculation process according to certain other aspects of the present disclosure (FIGS. 6K, 6L). FIGS. 6I and 6K have a scale bar of 1 micrometer (m), while 6J has a scale bar of 5 µm and 6L has a scale bar of 50 µm.

Figure 7:
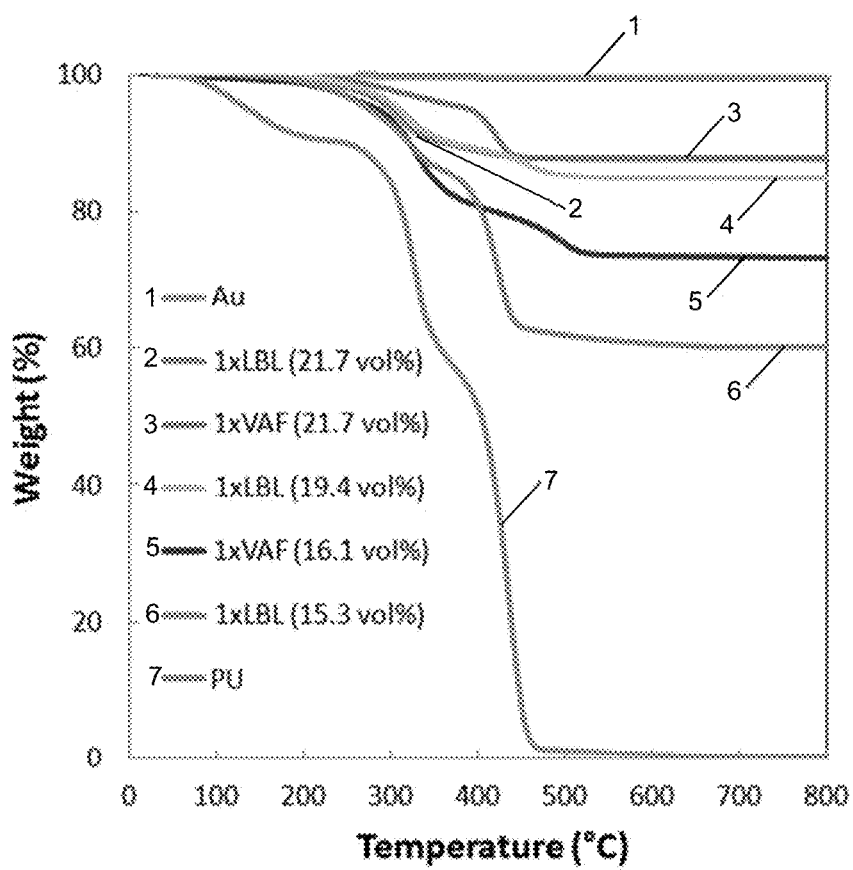

FIG. 7 shows thermal gravimetric analysis (TGA) traces of various materials for comparison: pure gold (Au), single layers of stretchable electrically conductive composite film formed by a layer-by-layer (1×LBL) process according to certain variations of the present disclosure, including embodiments having gold nanoparticles present at 15.3 vol. %, 19.4 vol. %, and 21.7 vol. % of the total film volume, single layers of stretchable electrically conductive composite film formed by a vacuum assisted flocculation (1×VAF) process according to certain variations of the present disclosure, including embodiments having gold nanoparticles present at 16.1 vol. % and 21.7 vol. % of the total film volume, and pure polyurethane (PU) polymer.

Figure 8A:
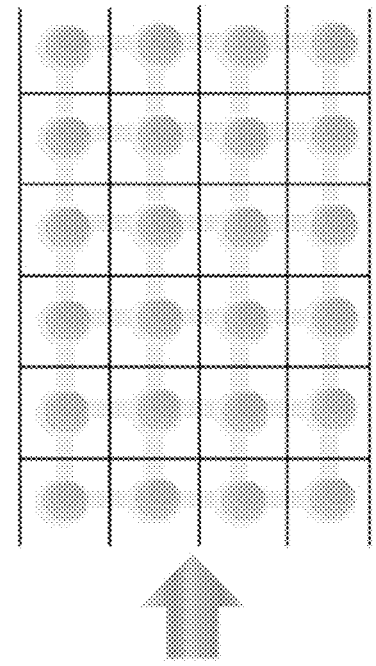
Figure 8B:
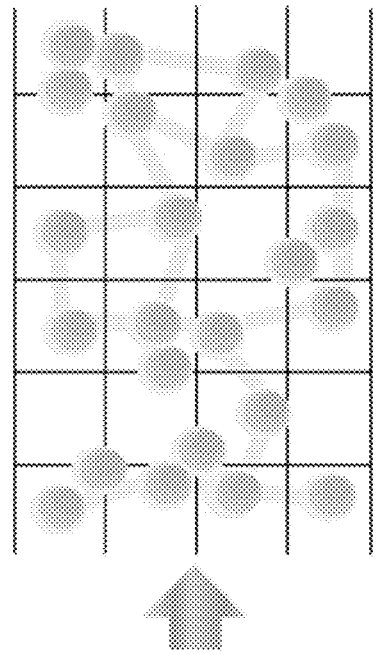
Figure 8C:
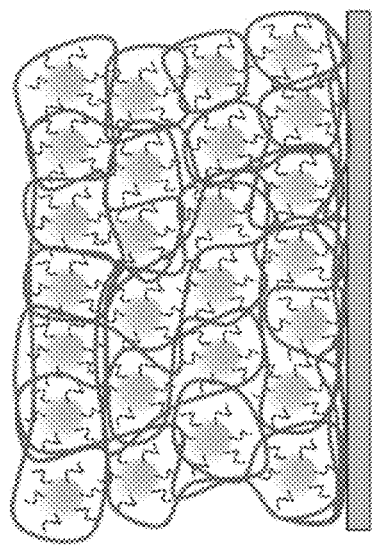
Figure 8D:
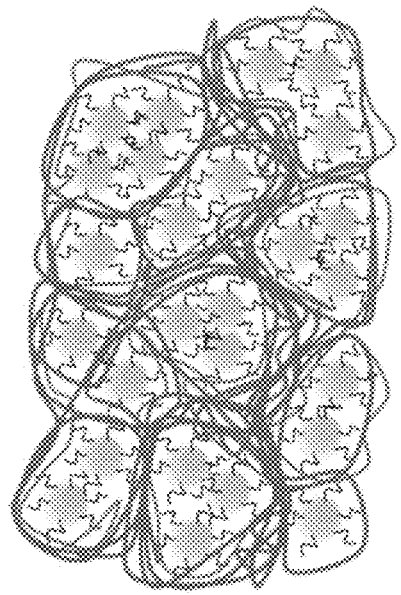

FIGS. 8A-8D show idealized schematics of well-dispersed nanoparticles in stretchable electrically conductive composite materials formed by a layer-by-layer process (LBL—FIGS. 8A-8B) and alternatively by a vacuum assisted flocculation process (VAF—FIGS. 8C-8D) in accordance with certain aspects of the present disclosure. FIGS. 8A and 8C are schematics showing the polymer and nanoparticle arrangements for LBL-formed and VAF-formed composites, respectively (the number of nanoparticles is same in both embodiments). The LBL-formed composite in FIG. 8A shows regular ordering of nanoparticles within the polymer, while the VAF-formed composite in FIG. 8C shows randomly distributed aggregates within the polymer. FIGS. 8B and 8D show percolation pathways between nearest neighbors of nanoparticles within the LBL-formed and VAF-formed composites in a two dimensional (2D) cross-sectional grid.

Figure 9A:
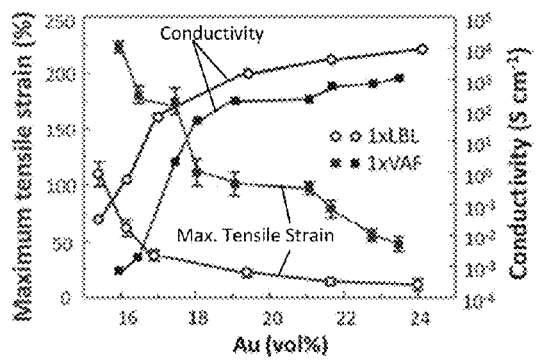
Figure 9B:
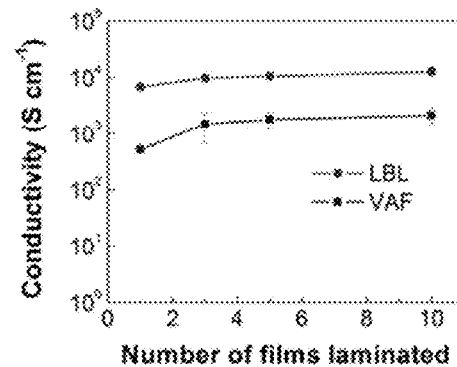
Figure 9C:
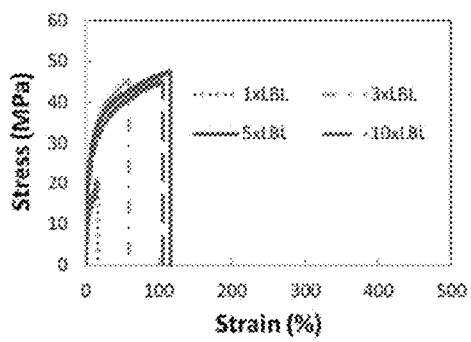
Figure 9D:
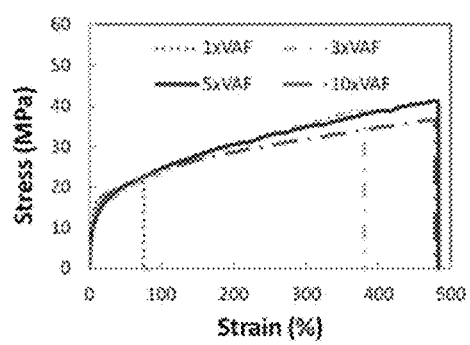
Figure 9E:
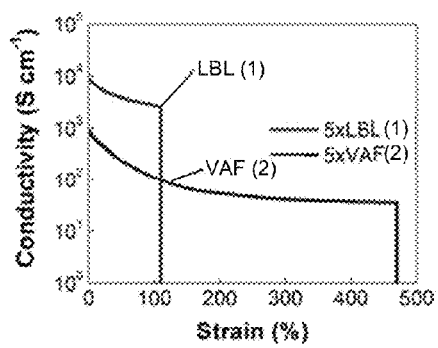
Figure 9F:
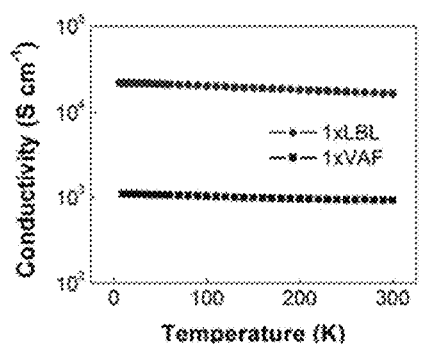
Figure 9G:
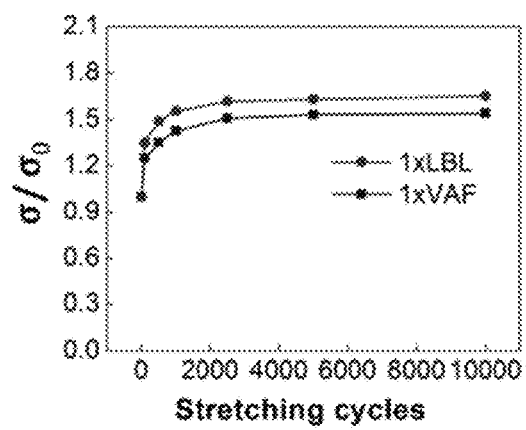
Figure 9H:
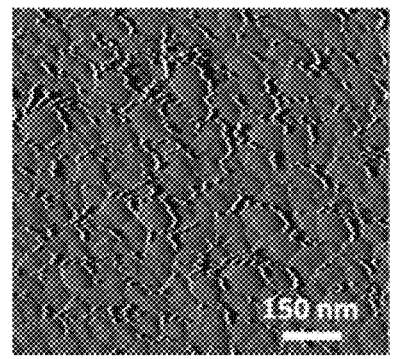
Figure 9I:
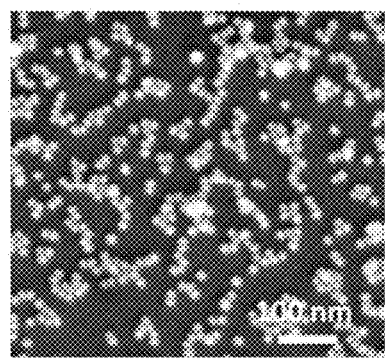
Figure 9J:
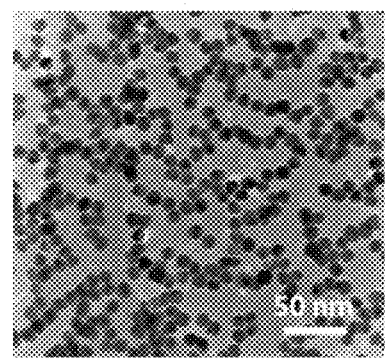
Figure 9K:
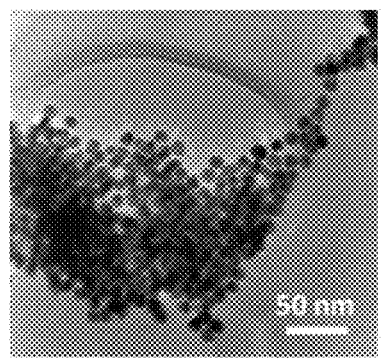

FIGS. 9A-9K. FIG. 9A shows dependence of strain and conductivity for stretchable electrically conductive composite materials in accordance with certain variations of the present disclosure, including a composite material formed by a layer-by-layer process (a single 1×LBL layer) and by a vacuum assisted flocculation process (a single 1×VAF layer) having varying gold nanoparticle content (volume %). FIG. 9B shows conductivity data of stretchable electrically conductive composite materials comprising a plurality of laminated film layers composed of consolidated 1, 3, 5, and 10 film layers for materials formed by either a layer-by-layer process (LBL) or a vacuum assisted flocculation process (VAF) according to certain aspects of the present disclosure. FIG. 9C shows stress-strain curves for consolidated LBL stacks composed of 1, 3, 5, and 10 LBL films. FIG. 9D shows stress-strain curves for consolidated VAF stacks composed of 1, 3, 5, and 10 VAF films. FIG. 9E shows conductivity as a function of uniaxial strain for stretchable electrically conductive composite materials comprising five consolidated/laminated layers of films, either formed by a layer-by-layer process (5×LBL) or a vacuum assisted flocculation process (5×VAF) in accordance with certain aspects of the present disclosure. FIGS. 9F and 9G show temperature dependence of conductivity for 1×LBL and 1×VAF composite films formed in accordance with the inventive principles, as well as a change in conductivity ($\sigma/\sigma_0$) of these 1×LBL and 1×VAF after recurrent stretching cycles, where strain $\in$=5%. FIGS. 9H-9J show atomic force microscopy (AFM) amplitude, SEM, and TEM images respectively of a single layer of stretchable electrically conductive composite materials formed by a layer-by-layer process comprising polyurethane and gold nanoparticles $(PU/NP)_1$ according to certain aspects of the present teachings. FIG. 9K shows a TEM image of a single layer of stretchable electrically conductive nanocomposite material formed by a vacuum assisted flocculation process comprising polyurethane and gold nanoparticles formed according to certain aspects of the present teachings.

FIGS. 10A-10F show conductivity and small angle X-ray scattering (SAXS) after recurrent stretching cycles in stretchable electrically conductive composite materials prepared in accordance with certain aspects of the present teachings. FIGS. 10A-10B are illustrations of the conductivity measurements by a two-probe method in different directions after 10,000 stretching cycles with $\in$=5% strain. Designation 1 indicates parallel to the tensile direction before strain cycles, 2 indicates perpendicular to the tensile direction before strain cycles, 3 indicates parallel to the tensile direction after strain cycles, and 4 indicates perpendicular to tensile direction after strain cycles. FIGS. 10C-10D show resistance data by two-probe method in the directions and recurrent stretching cycles for a single layer of stretchable electrically conductive composite materials formed by a layer-by-layer process (1×LBL FIG. 10C) and alternatively by a vacuum assisted flocculation process (1×VAF—FIG. 10D). FIG. 10E shows SAXS beam images of 10,000 cycled 1×LBL and 1×VAF films. Samples are horizontally placed for measurements and SAXS measurements are performed on the center of the films. FIG. 10F shows plots of scattering intensity, I(q), in respect to scattering vextor, q, for 1×LBL and 1×VAF films.

Figures 11A, 11N:
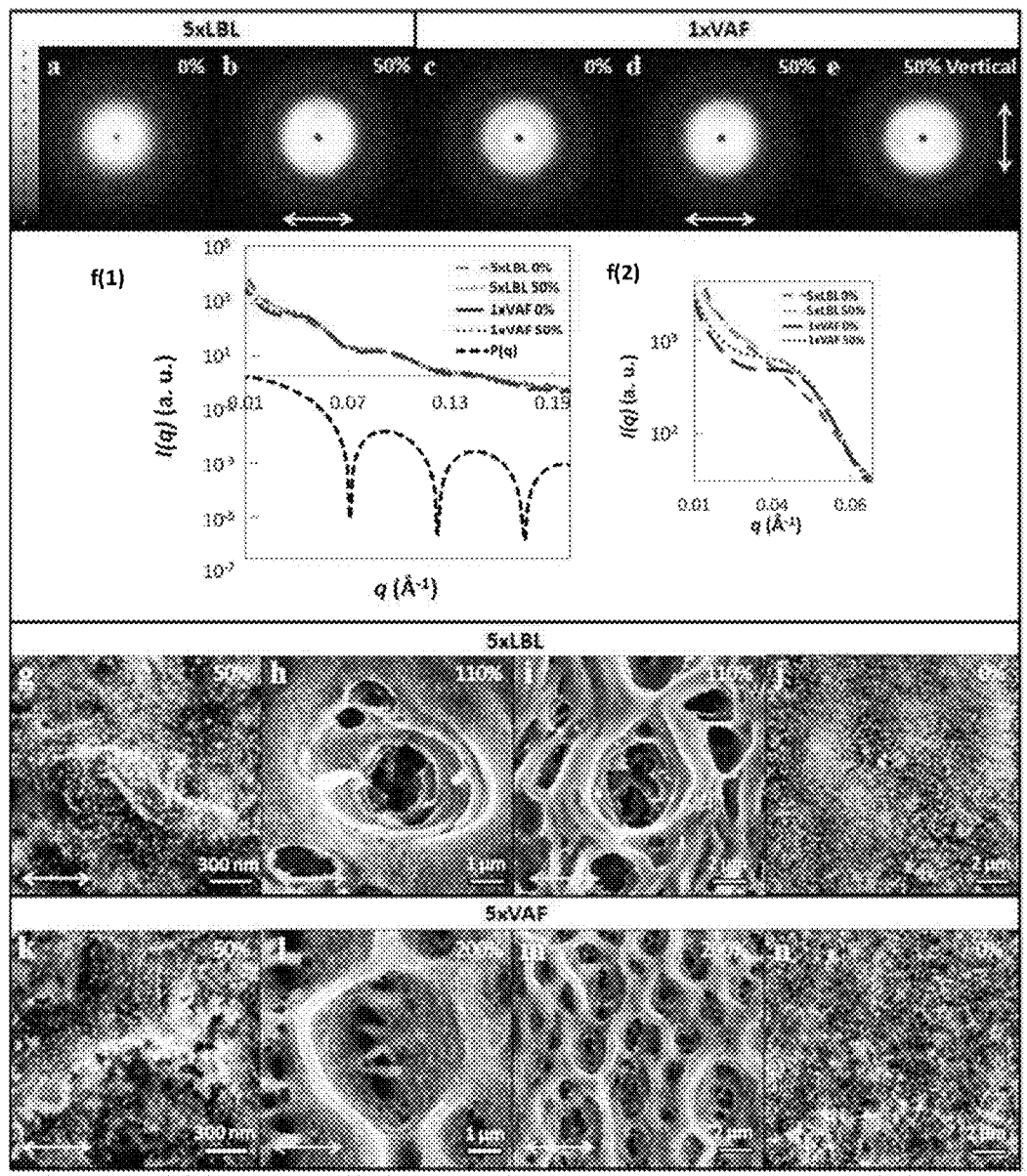

FIGS. 11A-11N. FIGS. 11A-11E show SAXS beam images of stretchable electrically conductive composite materials comprising five consolidated/laminated layers of films formed by a layer-by-layer process (5×LBL) or a single layer formed by vacuum assisted flocculation methods (1×VAF) at various strain levels. FIGS. 11A-11B are the 5×LBL material, where in FIG. 11A, $\in$=0% and in FIG. 11B, E=50% in direction indicated by arrow for the 5×LBL. FIGS. 11C-11E are images of 1×VAF material, where in FIG. 11C, $\in$=0%, FIG. 11D, $\in$=50% horizontal indicated by arrows, and in FIG. 11E, $\in$=50% vertical indicated by arrows. FIGS. 11F(1)-11F(2) show SAXS difraction curves for 5×LBL and 1×VAF films at 0% or 50% strain. The diffraction curve segments in FIG. 11F(1) around the peak at q=0.045 Å$^{-1}$ are given in a separate graph (FIG. 11F(2)). FIGS. 11G-11N show focused ion beam (FIB) milled samples of stretchable electrically conductive composite materials comprising five consolidated/laminated layers of films formed either by a layer-by-layer process (5×LBL) or vacuum assisted flocculation methods (5×VAF) at various strains (0%, 50%, 110% and 200%). The images are taken after five consecutive stretches to 110% and 200%, respectively. Unless otherwise mentioned, milling depths for samples are 1 μm for 5×LBL and 2 μm for 5×VAF. Stretching direction for all figures tested and imaged under stress is indicated by the double arrows.

FIGS. 12A-12B show high-voltage electron microscopy (HVEM) images for a stretchable electrically conductive composite material single layer film formed by vacuum assisted flocculation methods (1×VAF) in accordance with certain aspects of the present teachings. Imaging is performed on an initial point before stretching and a ruptured point after stretching. The specimens are prepared by using FIB.

Figure 13C:
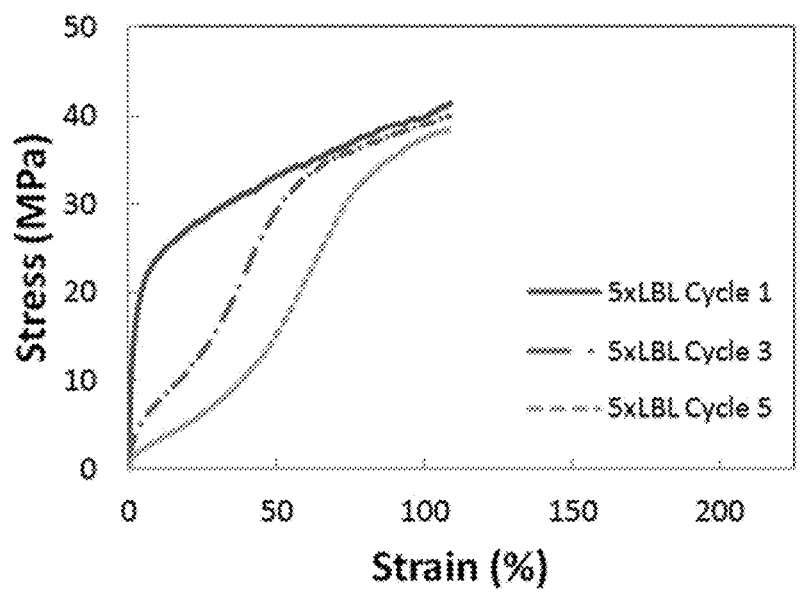
Figure 13D:
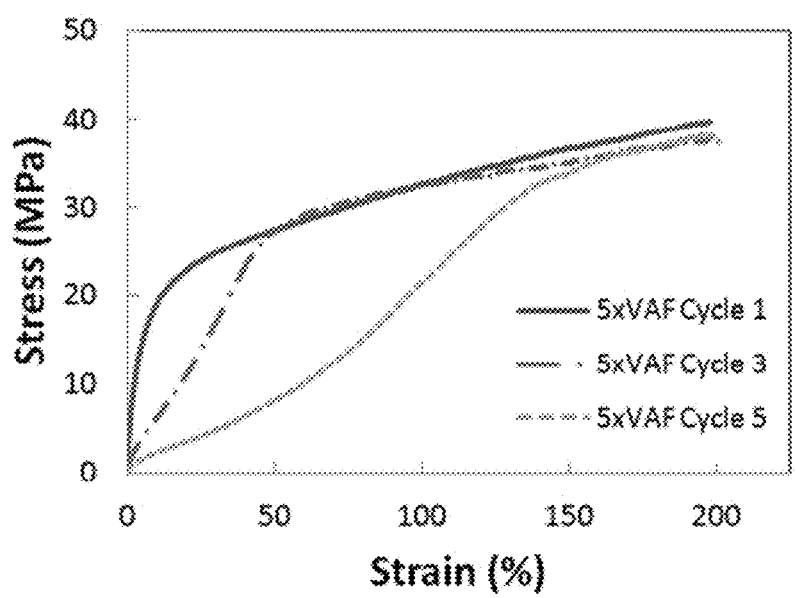

FIGS. 13A-13D show SEM images of surfaces of samples of stretchable electrically conductive composite materials according to certain aspects of the present disclosure comprising five consolidated/laminated layers of films formed either by a layer-by-layer process (5×LBL) in FIG. 13A or vacuum assisted flocculation methods (5×VAF) in FIG. 13B in a relaxed state after five consecutive stretches to 110% and 200%, respectively. Stress-strain curves for 5×LBL (FIG. 13C) and 5×VAF (FIG. 13D) are shown after specific stretching cycles with strain of 110% and 200%, respectively.

Figure 14A:
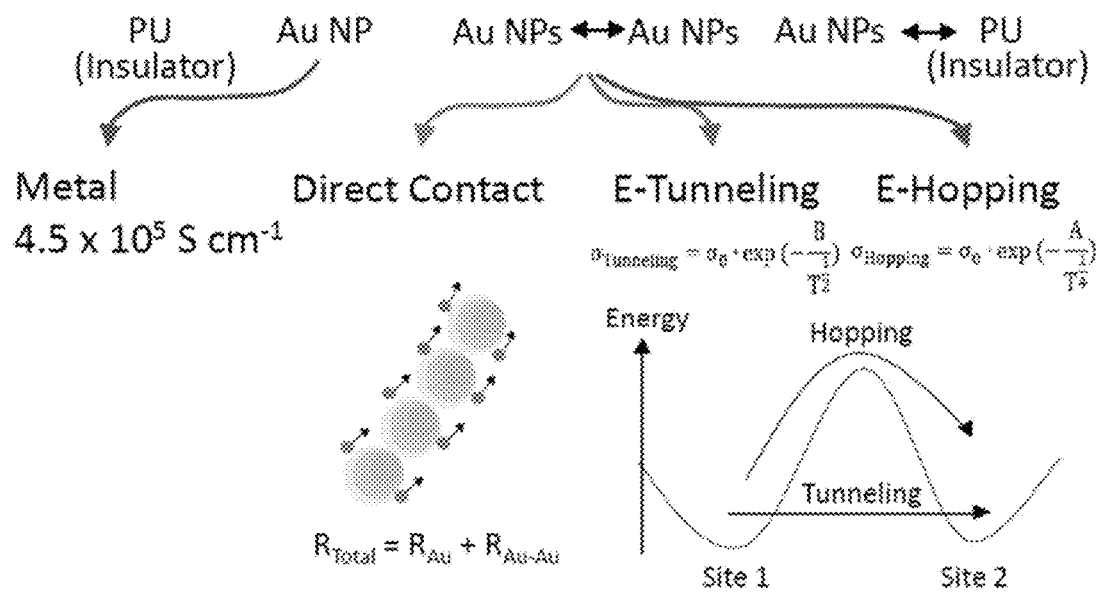
Figure 14B:
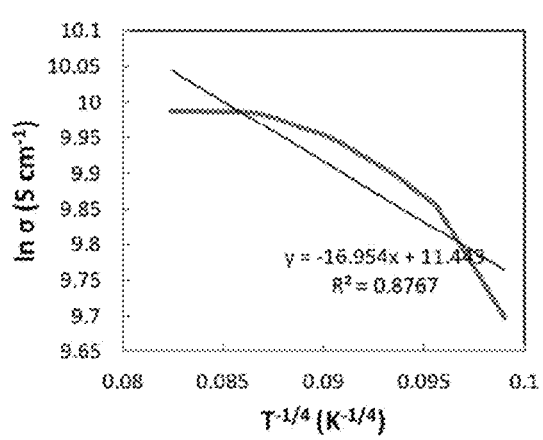
Figure 14C:
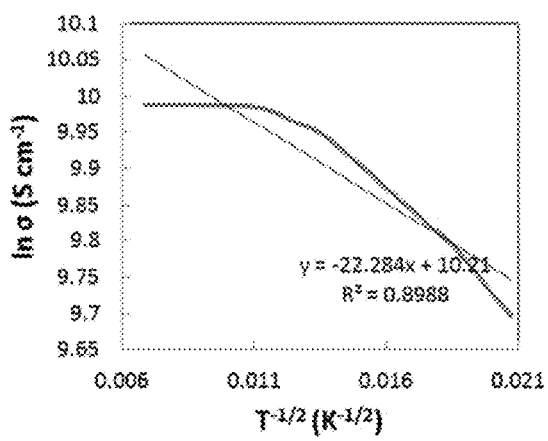
Figure 14D:
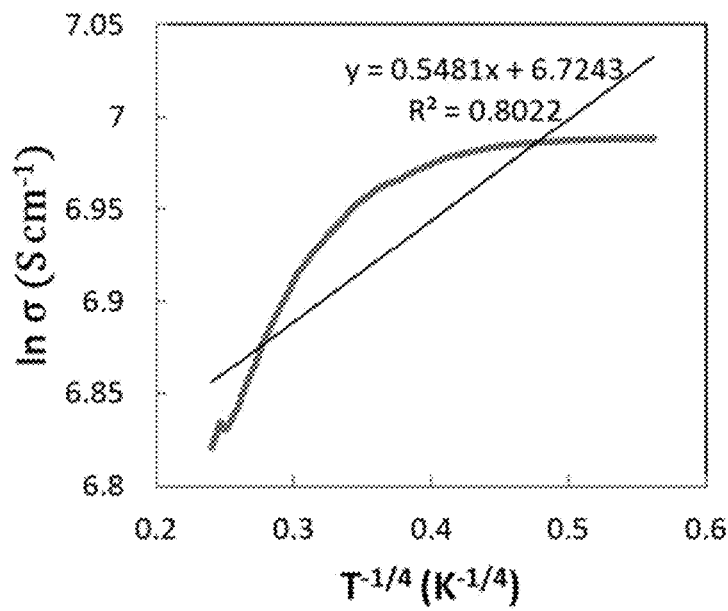
Figure 14E:
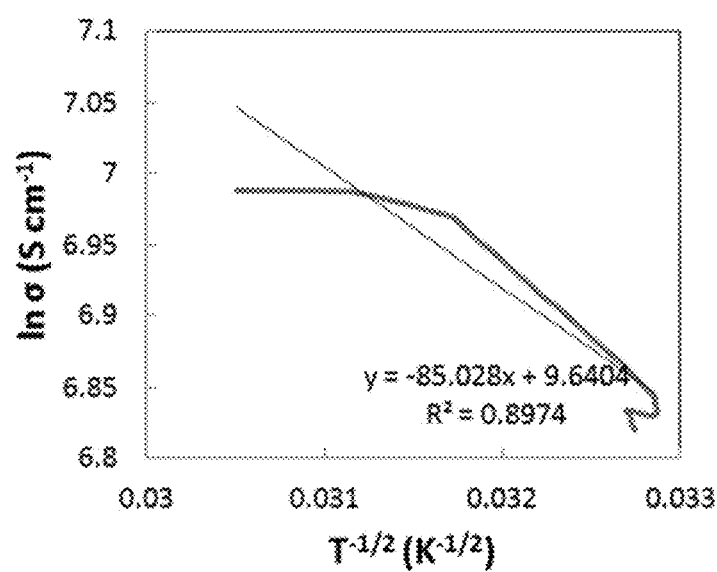

FIGS. 14A-14E show charge transport in stretchable electrically conductive composite materials in accordance with certain aspects of the present teachings. FIG. 14A is a schematic showing potential conduction behavior mechanisms in polyurethane-gold nanoparticle composites. FIGS. 14B and 14C are plots of ln σ vs. $T^{-1/4}$ and ln σ vs. $T^{-1/2}$ from data points of 1×LBL film (in FIG. 9F). FIGS. 14D and 14E show plots of ln σ vs. $T^{-1/4}$ and ln σ vs. $T^{-1/2}$ from data points of 1×VAF film (in FIG. 9F).

Figure 15A:
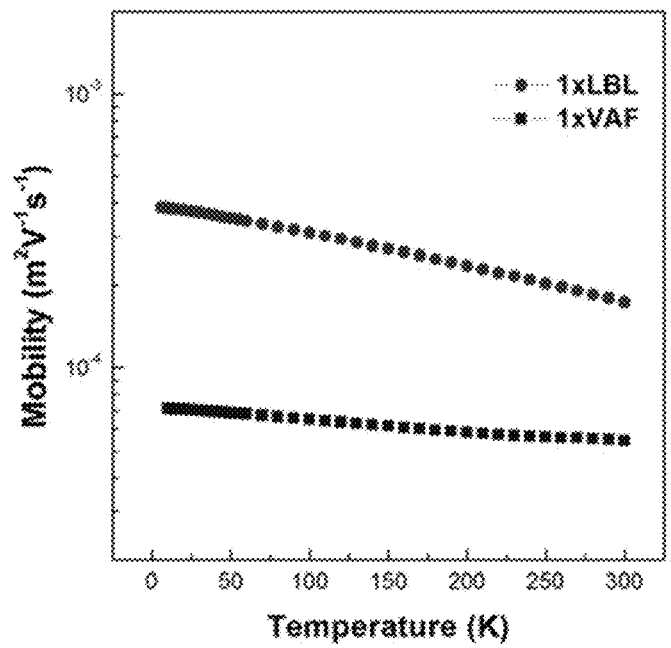
Figure 15B:
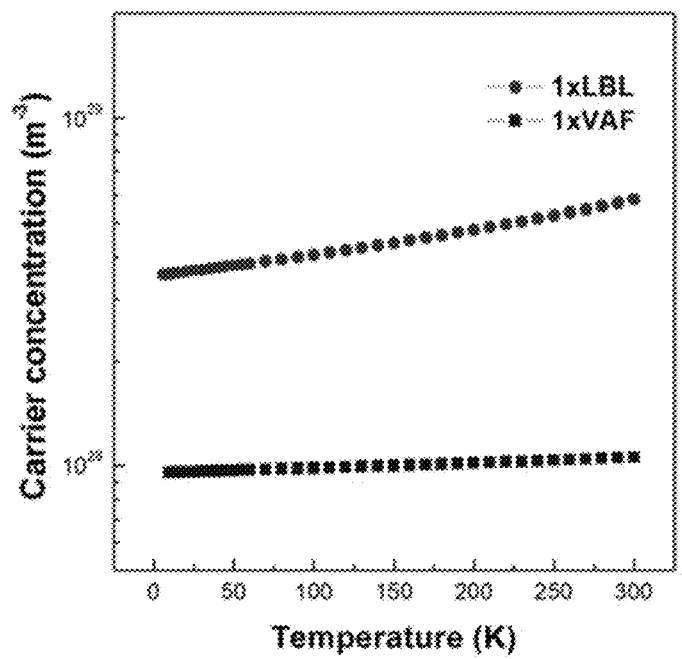

FIGS. 15A-15B. FIG. 15A shows electron mobility and FIG. 15B shows carrier concentration of a single layer composite formed by layer-by-layer techniques (1×LBL) in accordance with certain aspects of the present disclosure and a single layer composite formed by vacuum assisted flocculation techniques (1×VAF) in accordance with certain aspects of the present disclosure determined by the Hall Effect measurements.

Figure 16:
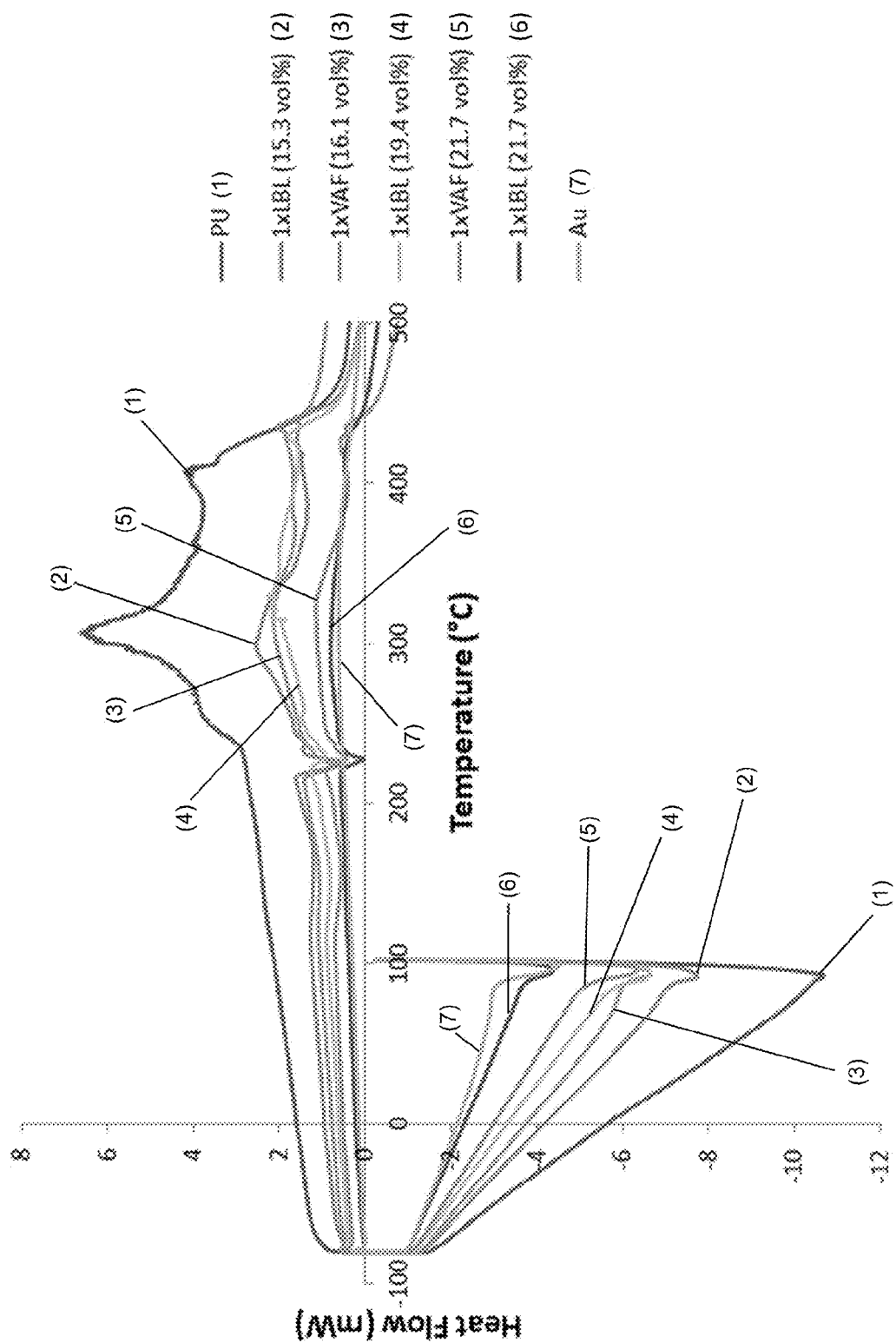

FIG. 16 shows differential scanning calorimetry (DSC) curves for pure polyurethane (PU), layer-by-layer formed (LBL) composites formed according to certain aspects of the present disclosure, vacuum assisted flocculation (VAF) composites formed according to certain aspects of the present disclosure, and pure gold nanoparticles (Au NPs). Nanoparticle contents of composites are given in parentheses and refer to the volume % of gold nanoparticles (Au NPs) in each material.

FIGS. 17A-17E. FIGS. 17A, 17C, and 17D show photographic images for the set-up used in measuring conductivity versus tensile strain dependence with four-probe method exemplified for a single layer composite formed by vacuum assisted flocculation techniques (1×VAF) in accordance with certain aspects of the present disclosure. Geometrical terms and directions of Cartesian coordinates are specified. The four probes are placed on the sample as shown in FIGS. 17A, 17C, and 17D. The sample being stretched is photographed to see change of length and width (one photograph every second) to calculate thickness of sample at each photograph under the assumption that there is no volume change. FIG. 17B shows a schematic of a sample before any stretching (as photographed in FIG. 17C), while FIG. 17E shows a schematic of the same sample after stretching and at a point before rupture (photographed in FIG. 17D). Video recorded resistance, strain, and thickness data are used to calculate data points for the conductivity values.

Figures 18A, 18B, 18C, 18D:
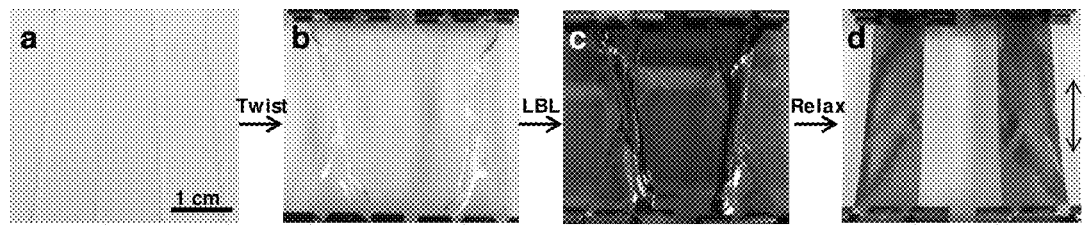
Figure 18E:
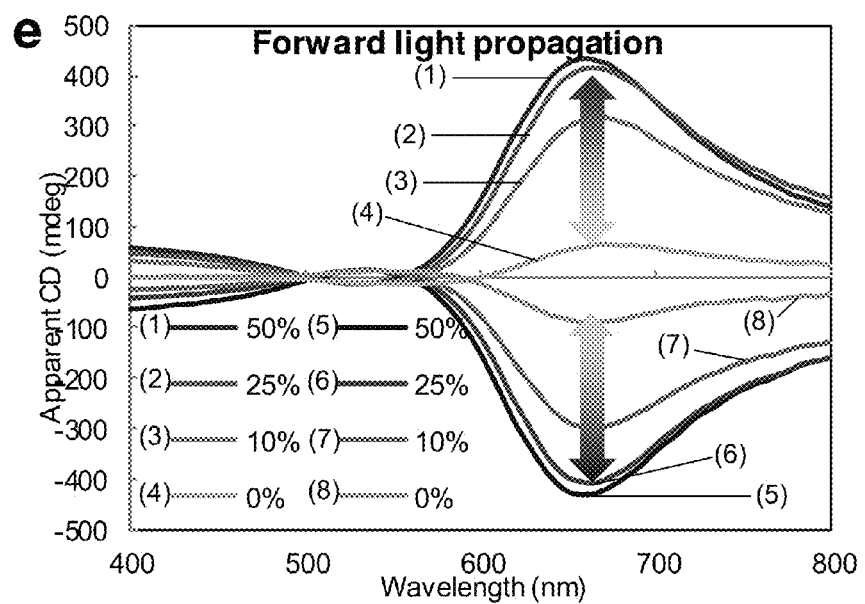
Figure 18F:
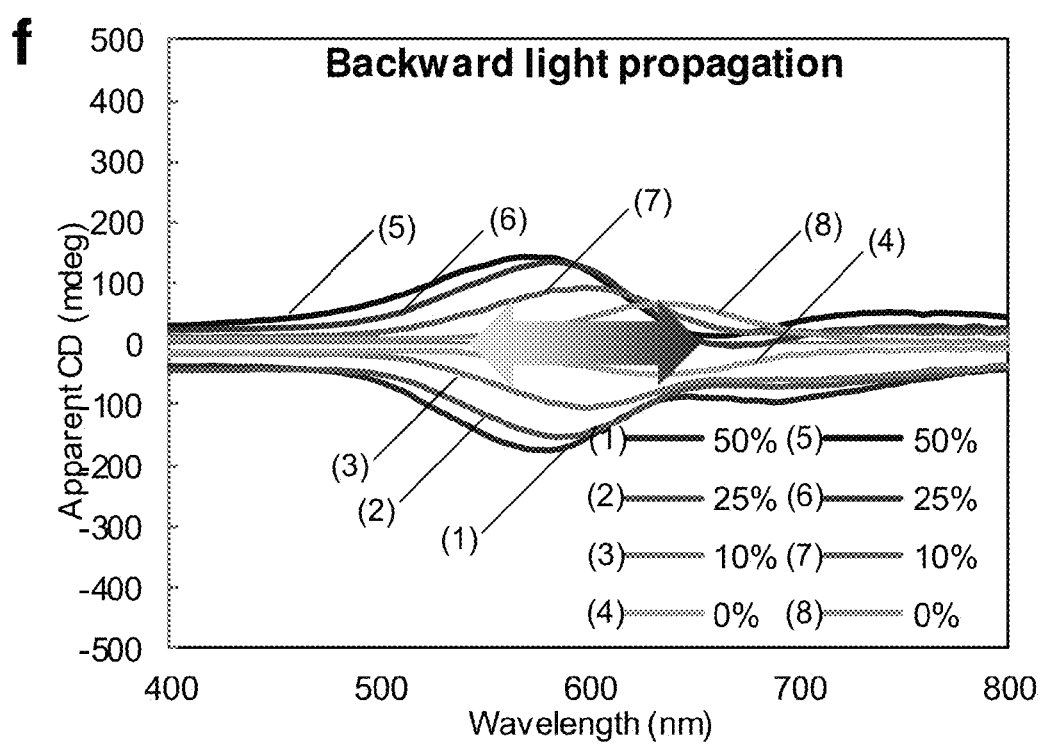

FIGS. 18A-18F show preparation and properties of chiral plasmonic thin films prepared in accordance with certain aspects of the present disclosure. FIG. 18A shows a neat PDMS substrate on a glass slide. FIG. 18B shows fixed PDMS substrates after twist of the PDMS substrate like in FIG. 18A in different directions (left is left handed (LH) from a clockwise twist and right is right handed (RH) from counterclockwise twist along the x-axis). FIG. 18C shows a substrate having five layer pairs of PU and Au NPs deposited on the substrate of FIG. 18B. FIG. 18D shows release of tension from a pre-twist position. FIGS. 18E-18F show chiroptical properties of samples measured after being relaxed to be flattened. Stretching directions are indicated by the double arrows. FIG. 18E shows circular dichroism (CD) spectra signals from forward light propagation (from buckle-side to crack-side) and FIG. 18F shows CD spectra from backward light propagation (from crack-side to buckle-side) under various strain levels of 0%, 10%, 25%, and 50%, respectively. Numbers 1-4 are LH samples and 5-8 are RH samples.

Figures 19A, 19B, 19C, 19D:
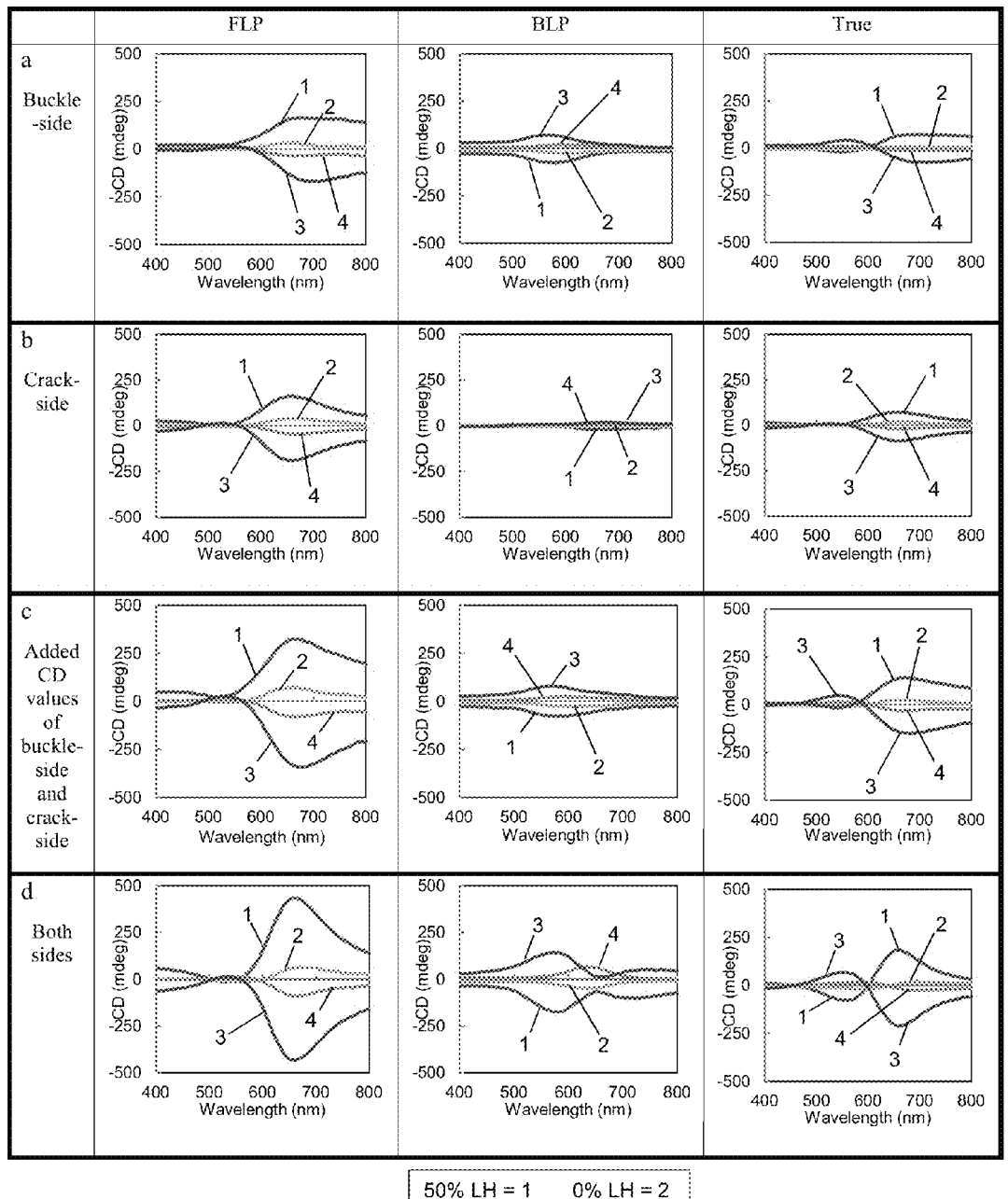

FIGS. 19A-19D show comparisons of circular dichroism (CD) spectra signals from one-sided samples and from both sides. FIG. 19A shows CD signals from a buckle side, FIG. 19B from a crack side, FIG. 19C shows addition of CD values from both the buckle and crack sides, while FIG. 19D shows CD signals from both sides. 1 designates a left handed (LH) chirality at 50% stretching, 2 designates LH at 0% stretching, 3 designates right handed (RH) chirality at 50% stretching, while 4 designates RH at 0% stretching.

Figure 20:
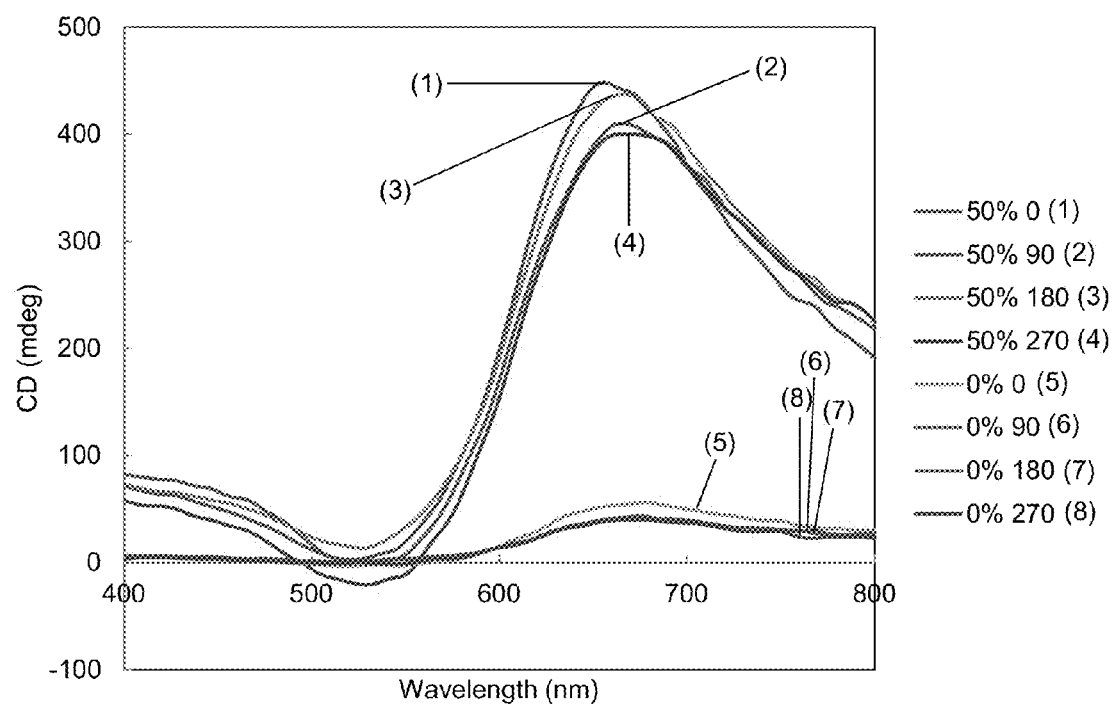

FIG. 20 shows intrinsic properties for left-handed (LH) embodiments, including CD signals to rotations for 0% and 50% stretching levels.

Figure 21A:
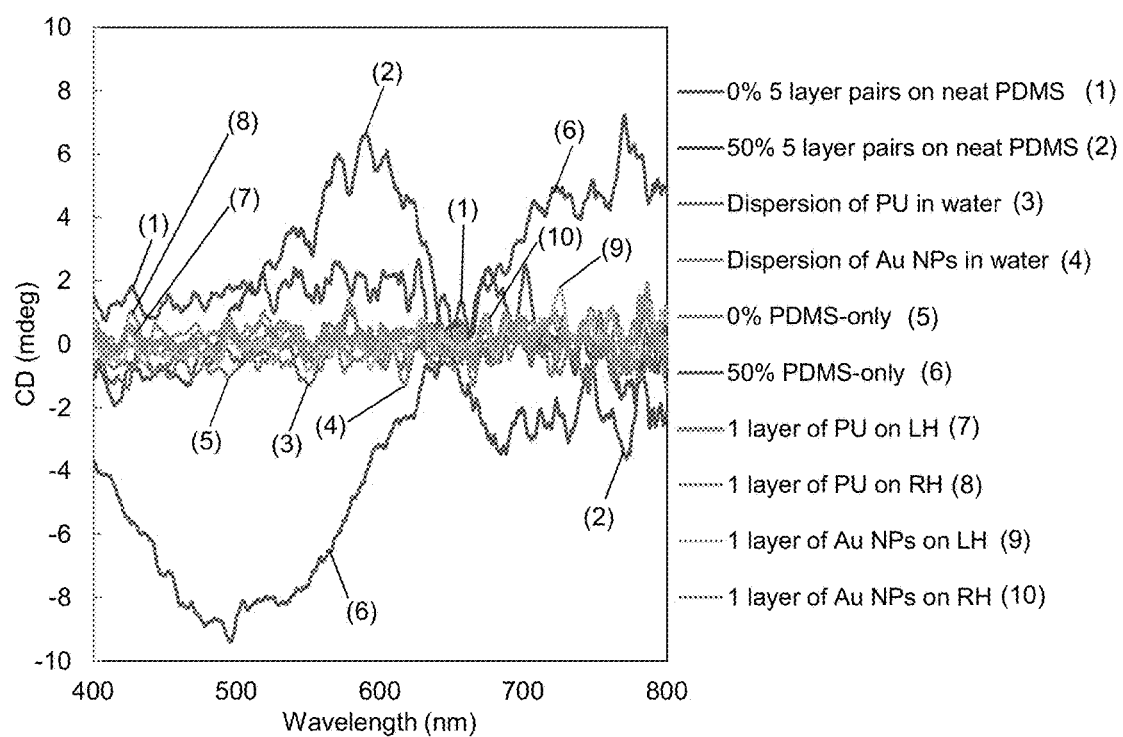
Figure 21B:
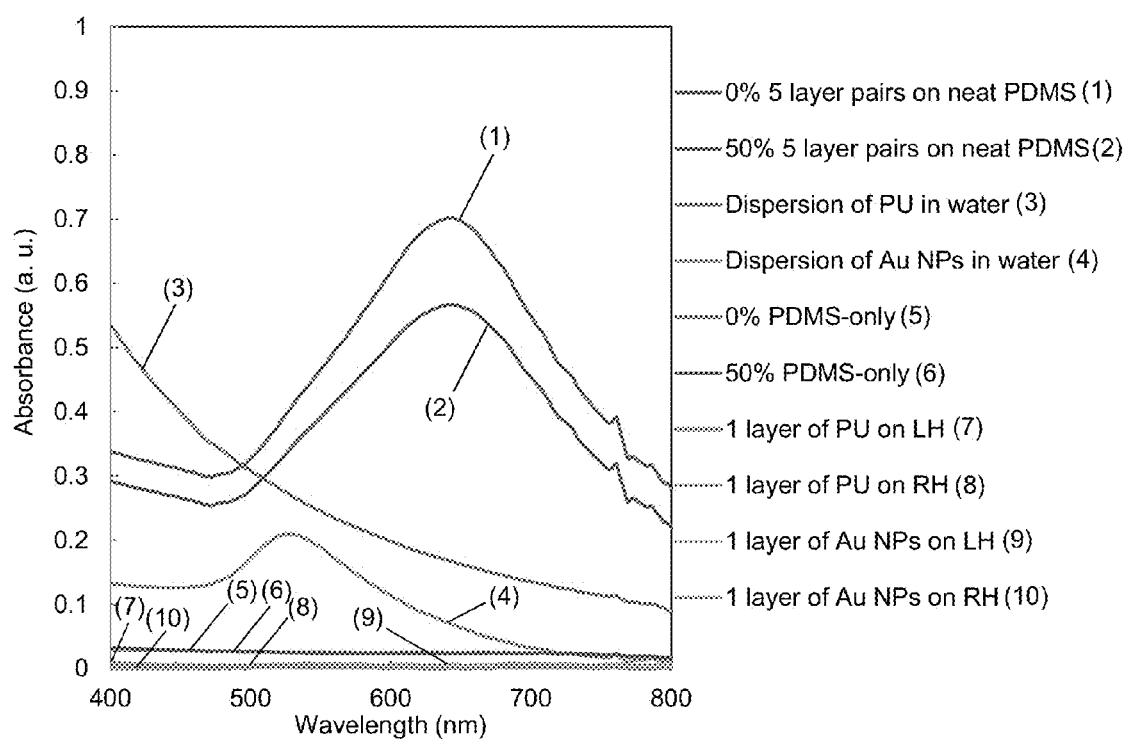

FIGS. 21A-21B show control experiments of chiroptical properties of comparative materials. FIG. 21A shows CD and FIG. 21B shows absorbance spectra of various control samples.

Figure 22:
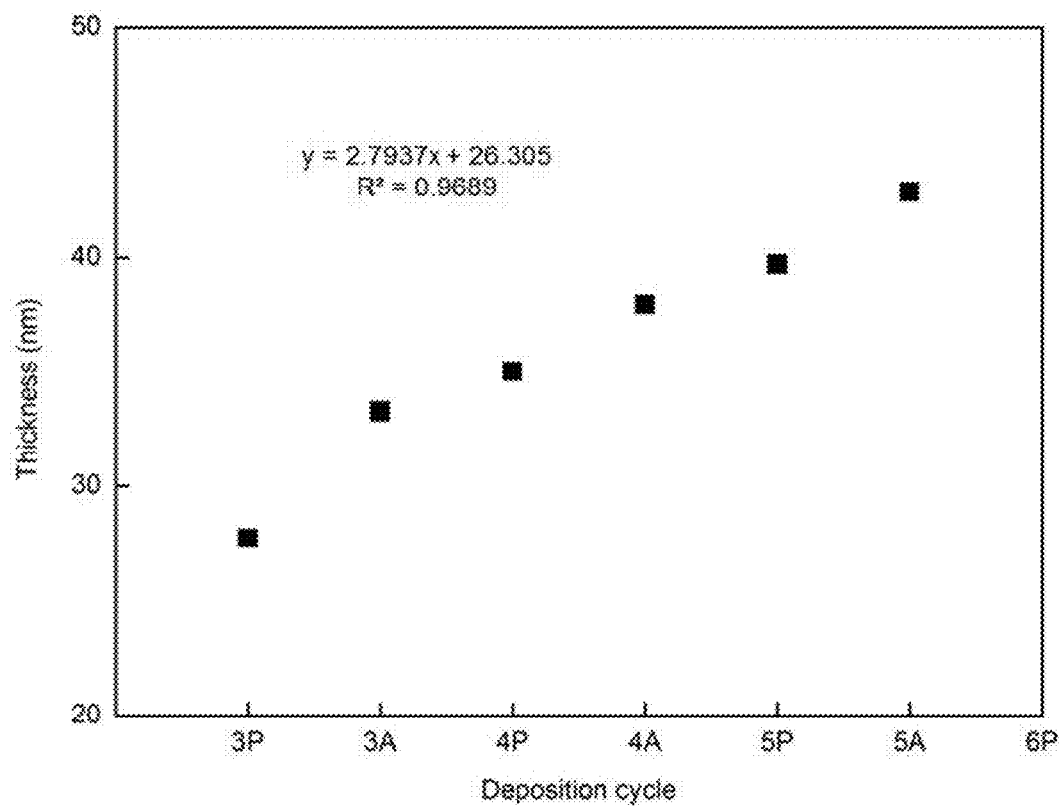

FIG. 22 shows dependence of thickness of layers on a number of the deposition cycles. Polyurethane layers (3P, 4P, and 5P) and gold nanoparticle layers (3A, 4A, and 5A) with the same number correspond to one deposition cycle. Thickness change is measured by ellipsometry as the LBL film is deposited on a silicon wafer.

Figure 23:
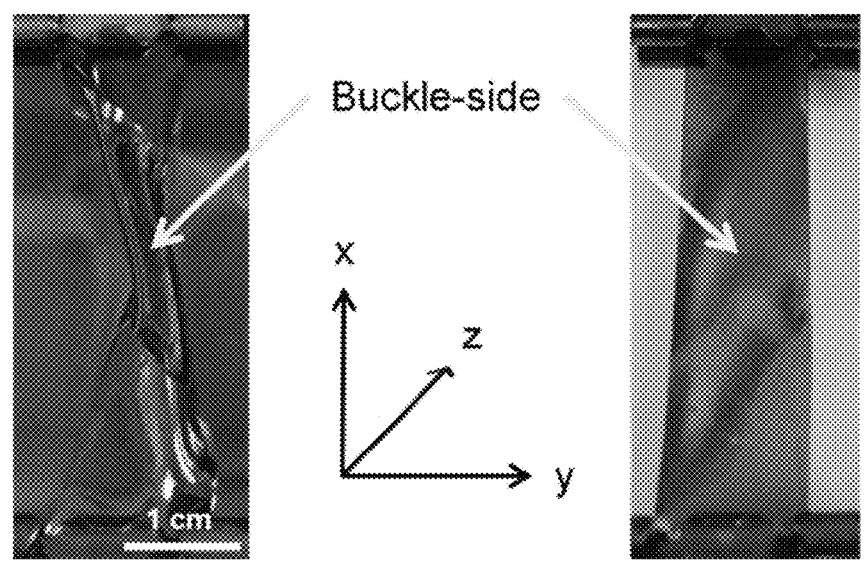

FIG. 23 shows designation of sides and Cartesian coordinates for a left-handed (LH) chirality sample. A crack-side is the opposite of buckle-side and same designations are applied to right-handed (RH) chirality. All parameters are defined to the right-handed Cartesian coordinate system with the z-axis directed perpendicular to the buckle-side of the film.

Figures 24A, 24B:
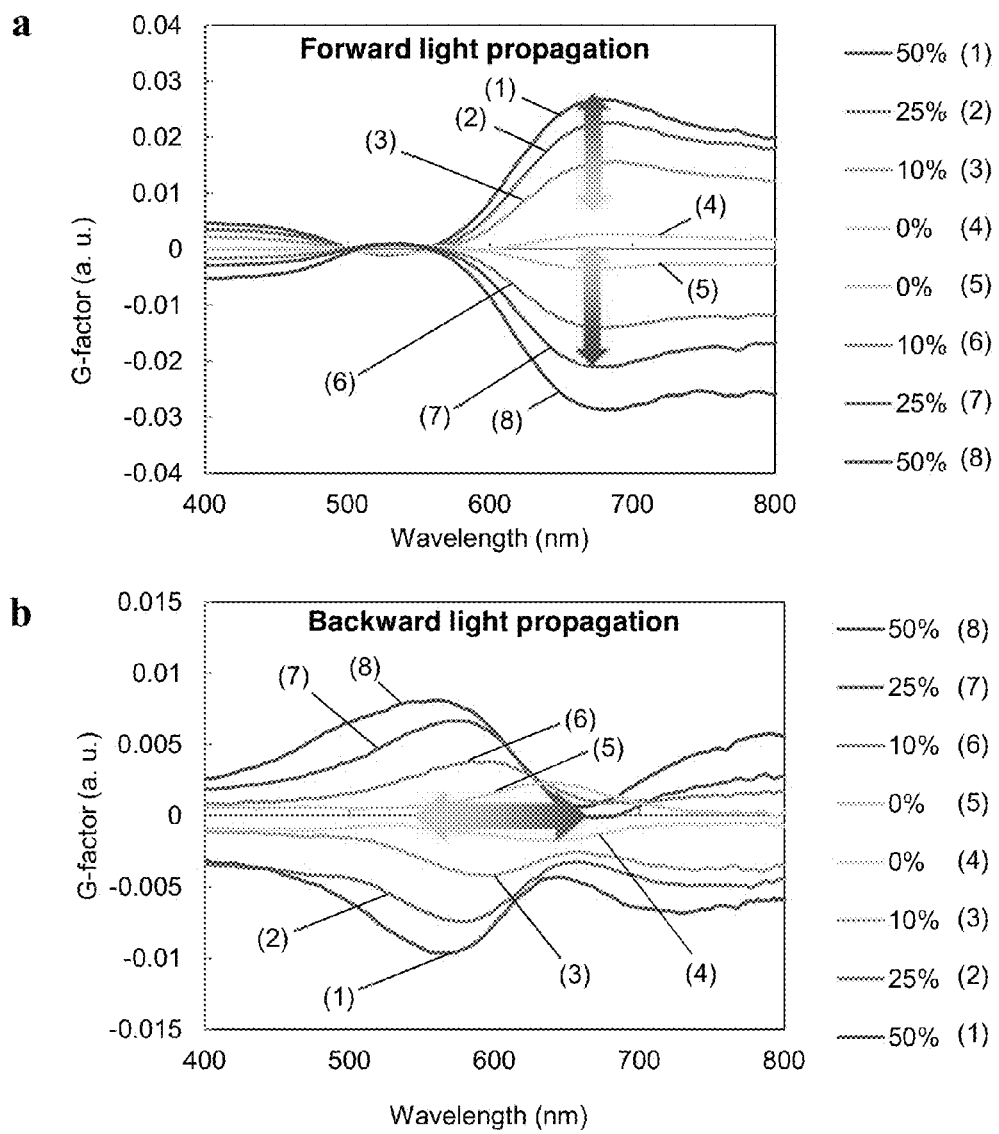

FIGS. 24A-24B show G-factor spectra from forward (FIG. 24A) and backward (FIG. 24B) light propagation under various strain levels at 0%, 10%, 25%, and 50%, respectively. For all spectra, left-handed chirality (LH) is designated (1)-(4) and right handed chirality (RH) is (5)-(8).

Figure 25:
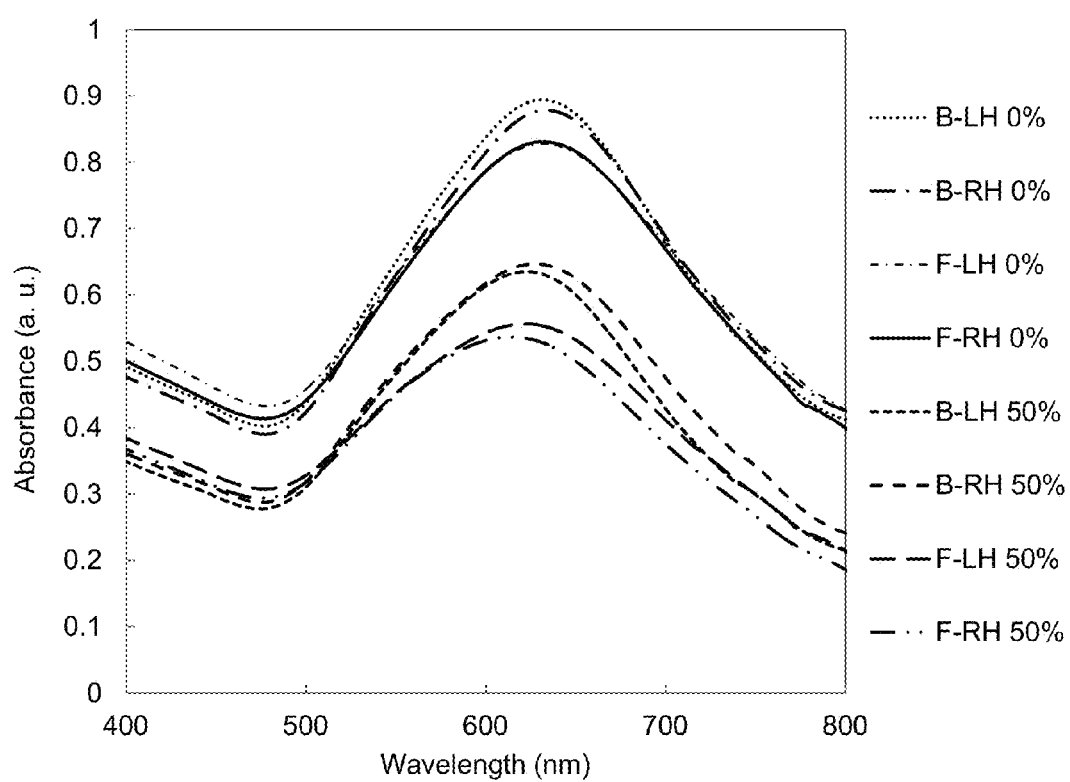

FIG. 25 shows absorbance spectra of stretchable chiral films prepared in accordance with certain aspects of the present disclosure for front left handed (F-LH) and back left handed (B-LH) and front right handed (F-RH) and back right handed (B-RH) under strains of 0% and 50%.

Figures 26A, 26B:
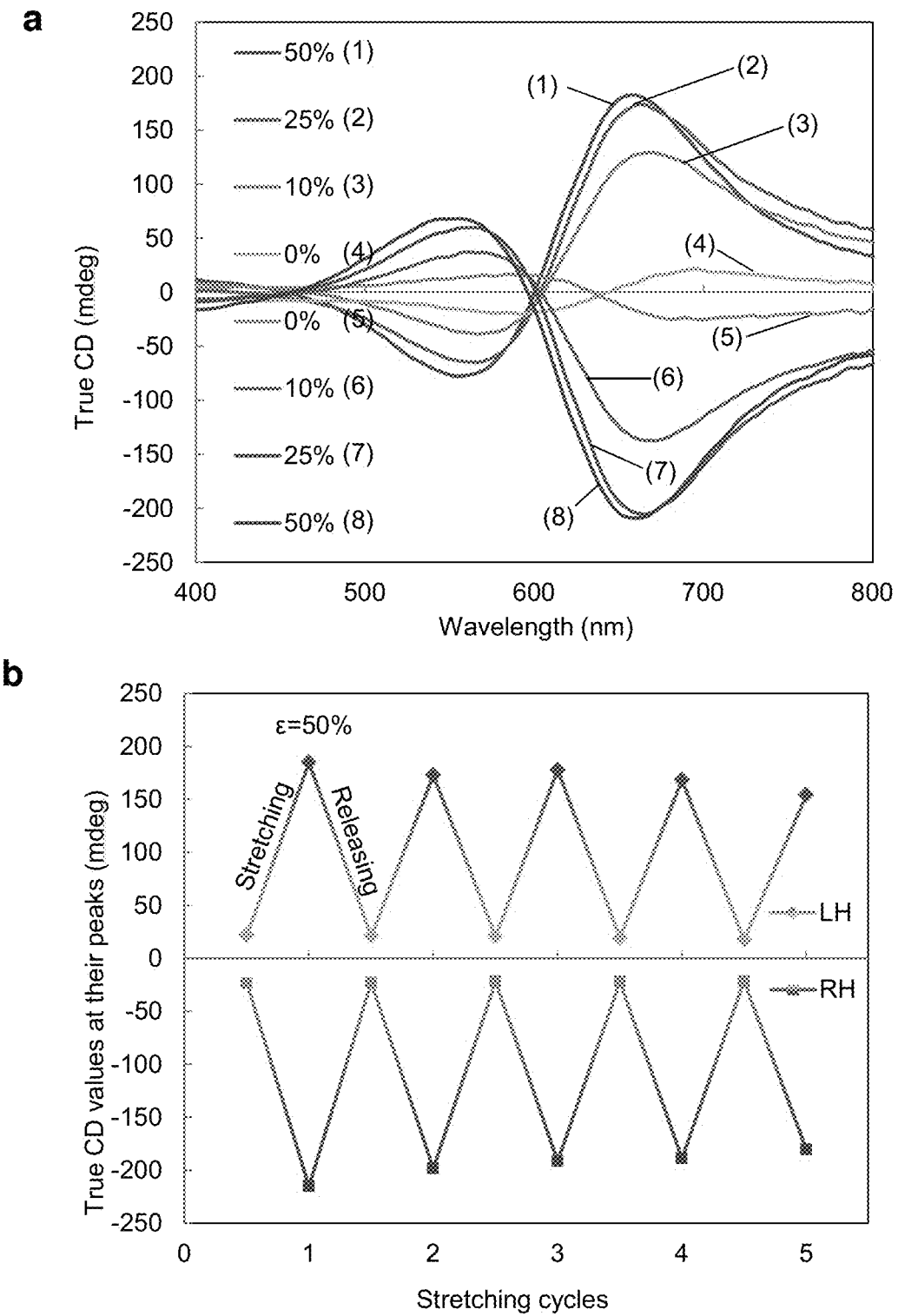
Figures 27A, 27B, 27C, 27D, 27E, 27F, 27G, 27H, 27I, 27J, 27K, 27L:
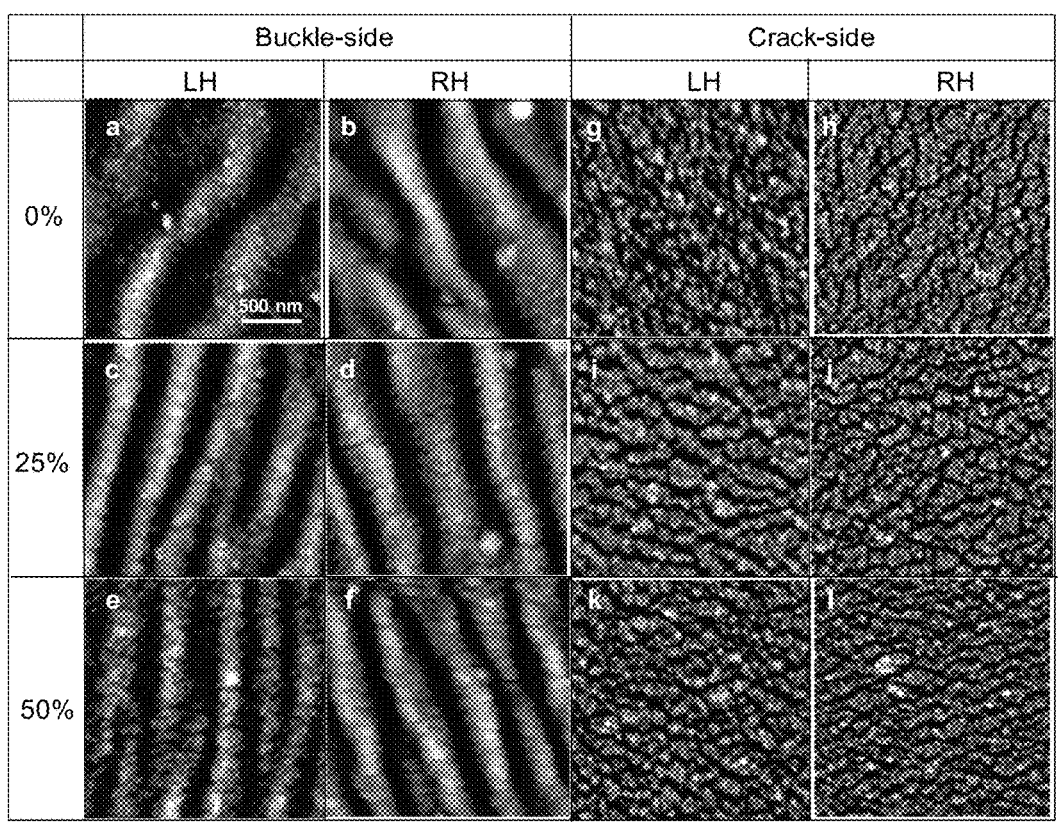
Figures 28A, 28B, 28C, 28D, 28E, 28F, 28G, 28H, 28I, 28J, 28K, 28L:
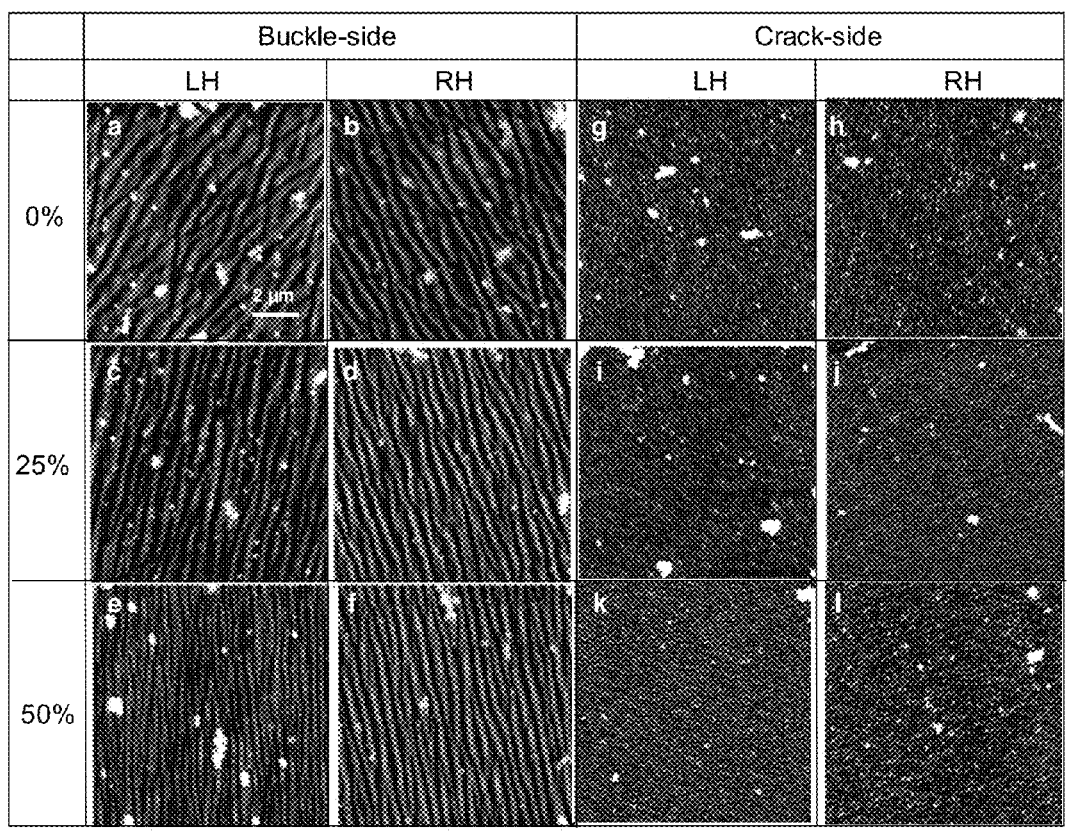

FIGS. 26A-26B. True CD signals excluding linear effects are shown. FIG. 26A shows true CD spectra under various strain levels of 0%, 10%, 25%, and 50%, respectively. Designations (1)-(4) are for left-handed (LH) chirality and (5)-(8) for right-handed chirality. FIG. 26B shows true CD values at their peaks for five cycles of reversible stretching to 50% and releasing to 0%.

FIGS. 27A-27L. FIGS. 27A-27L show atomic force microscopy (AFM) images at 500 nm scale of the evolution of morphology of flattened to stretched positions (from 0% to 25% to 50% strain) for chiral plasmonic thin films prepared in accordance with certain aspects of the present disclosure. Buckle-sides of left handed chirality (LH) and right handed (RH) chiral plasmonic films are respectively shown at various strain levels in FIGS. 27A-27F, while images of crack-sides of the left handed chirality (LH) and right handed (RH) chiral plasmonic films are shown in FIGS. 27G-27L.

FIGS. 28A-28L show atomic force microscopy (AFM) images over a large area (2 μm scale) showing the evolution of morphology of flattened to stretched positions (from 0% to 25% to 50% strain) for chiral plasmonic thin films prepared in accordance with certain aspects of the present disclosure. Buckle-sides of left handed chirality (LH) and right handed (RH) chiral plasmonic films are respectively shown at various strain levels in FIGS. 28A-28F, while images of crack-sides of the left handed chirality (LH) and right handed (RH) chiral plasmonic films are shown in FIGS. 28G-28L.

Figures 29A, 29B, 29C:
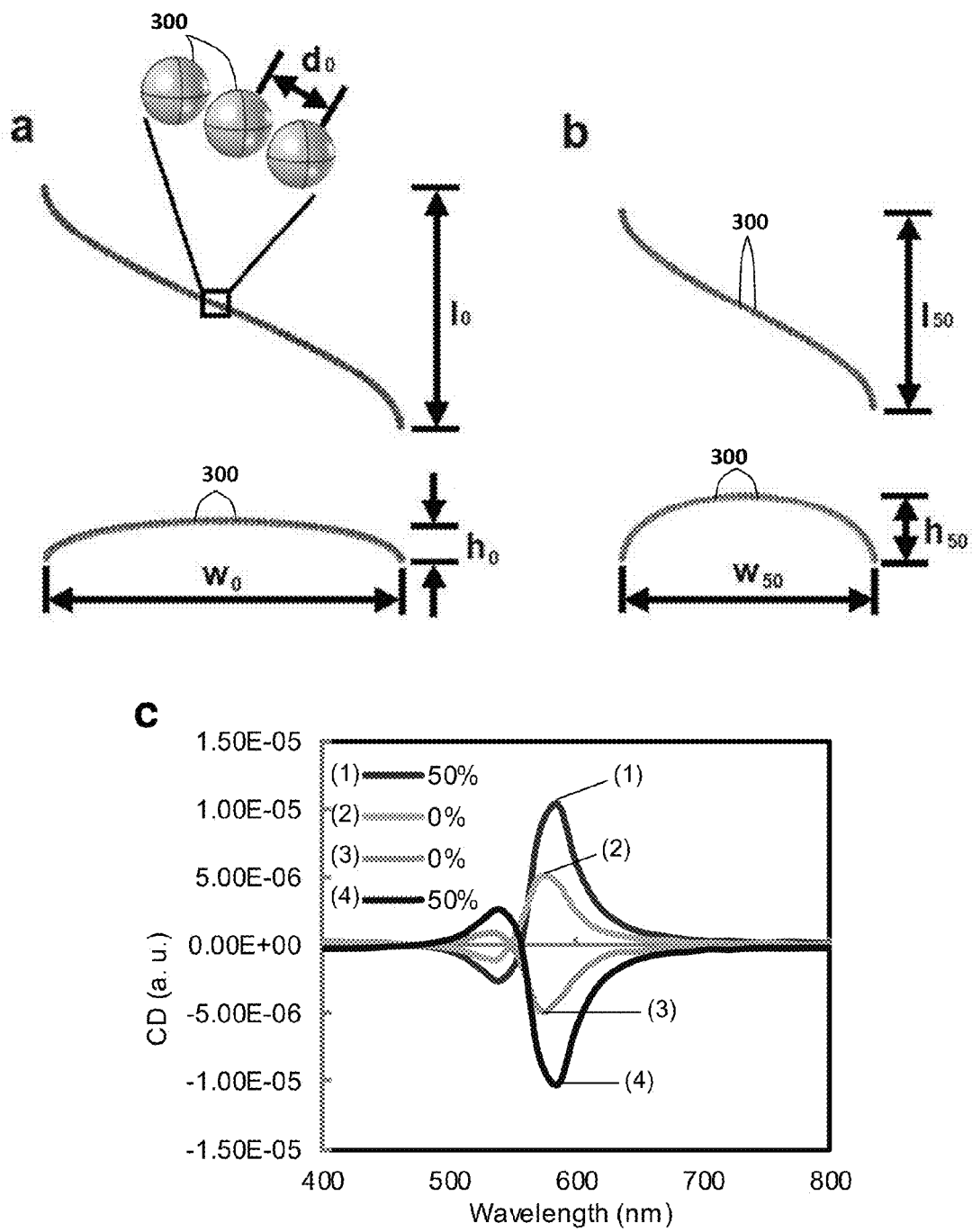
Figure 29D:
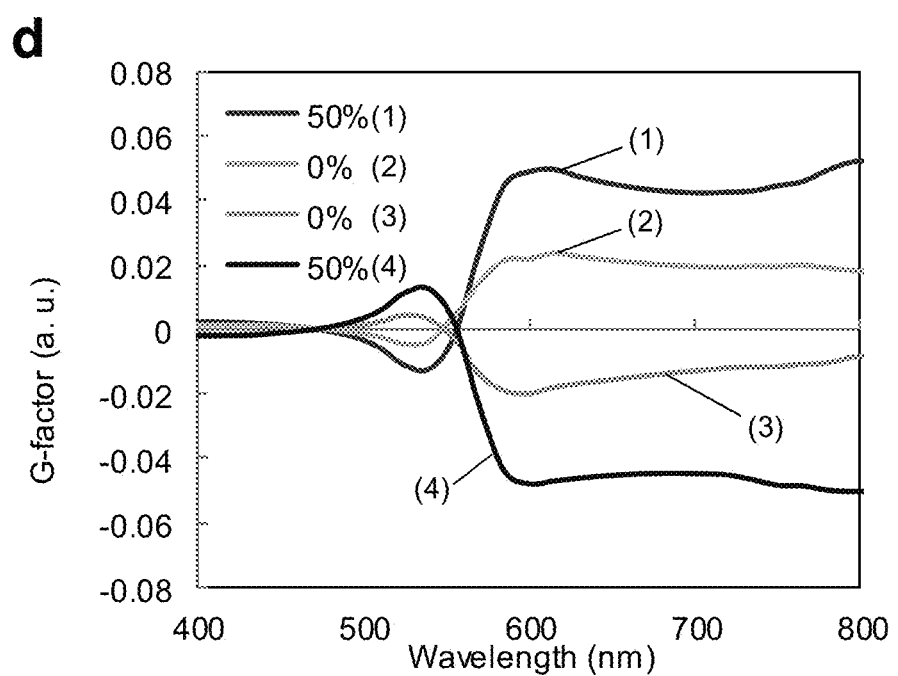

FIGS. 29A-29D show theoretical data and mechanisms for certain stretchable plasmonic films prepared in accordance with the present disclosure. FIGS. 29A-29B show a schematic of a unit model of helically organized nanoparticles (NPs) for a left handed chirality (LH) sample prepared in accordance with certain aspects of the present disclosure under strains of 0%, and 50%, respectively. FIGS. 29C-29D show theoretical chiroptical activities of left handed (LH) (designated (1) and (2)) and right handed (RH) (designated (3) and (4)) chiral films under strains of 0%, and 50% of CD spectra and G-factor, respectively.

Figure 30:
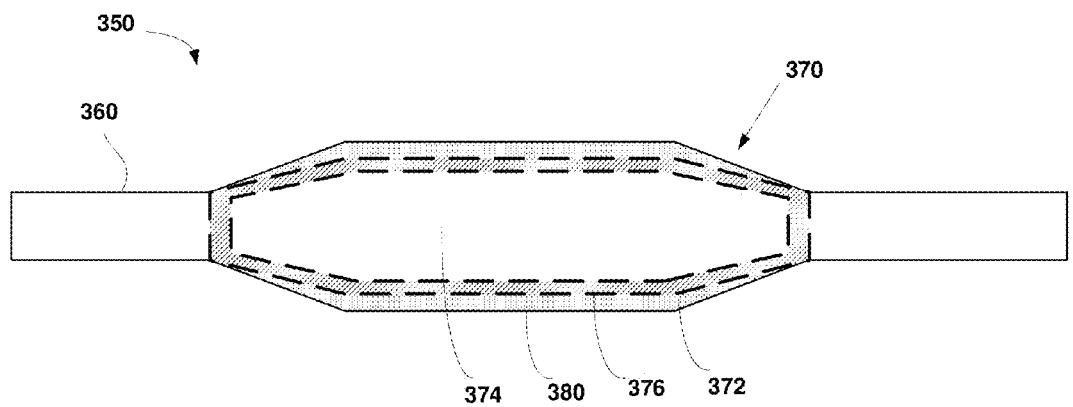

FIG. 30 shows a schematic of an exemplary medical device (an angioplasty balloon on a catheter) comprising stretchable electrically conductive composite materials in accordance with certain aspects of the present disclosure.

Figure 31:
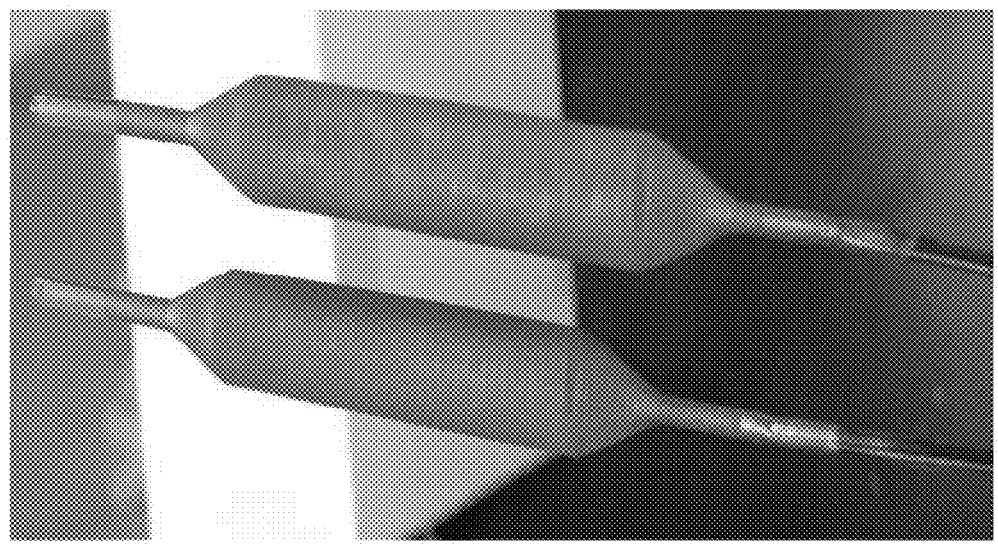

FIG. 31 shows pictures of catheters having angioplasty balloons comprising a coating of stretchable electrically conductive composite materials in accordance with certain aspects of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and the may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It should be understood for any recitation of a method, composition, device, or system that "comprises" certain steps, ingredients, or features, in certain alternative variations, it is also contemplated that such a method, composition, device, or system may also "consist essentially of" the enumerated steps, ingredients, or features, so that any other steps, ingredients, or features that would materially alter the basic and novel characteristics of the invention are excluded therefrom.

Throughout this disclosure, the numerical values represent approximate measures or limits to ranges to encompass minor deviations from the given values and embodiments having about the value mentioned as well as those having exactly the value mentioned. Other than in the working examples, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints given for the ranges. Thus, unless specified otherwise, ranges are inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight or volume percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The present disclosure provides in various aspects, a stretchable composite material. By "stretchable" it is meant that materials, structures, components, and devices are capable of withstanding strain, without fracturing or other mechanical failure. Stretchable materials in accordance with certain aspects of the present disclosure are extensible and thus are capable of stretching and/or compression, at least to some degree, without damage, mechanical failure or significant degradation in performance.

"Young's modulus" is a mechanical property referring to a ratio of stress to strain for a given material. Young's modulus may be provided by the expression:

$$E = \frac{(\text{stress})}{(\text{strain})} = \frac{\sigma}{\epsilon} = \frac{L_o}{\Delta L} \times \frac{F}{A}$$

wherein engineering stress is $\sigma$, tensile strain is $\epsilon$, E is the Young's modulus, $L_o$ is an equilibrium length, $\Delta L$ is a length change under the applied stress, F is the force applied and A is the area over which the force is applied.

In certain aspects, stretchable materials, structures, components, and devices may undergo a maximum tensile strain of at least about 15% without fracturing; optionally greater than or equal to about 50% without fracturing, optionally greater than or equal to about 75% without fracturing, optionally greater than or equal to about 100% without fracturing, optionally greater than or equal to about 200% without fracturing, optionally greater than or equal to about 300% without fracturing, optionally greater than or equal to about 400% without fracturing, and in certain embodiments, greater than or equal to about 450% without fracturing as will be described in more detail below.

Stretchable materials of the present disclosure may also be flexible, in addition to being stretchable, and thus are capable of significant elongation, flexing, bending or other deformation along one or more axes. The term "flexible" can refer to the ability of a material, structure, or component to be deformed (for example, into a curved shape) without undergoing a permanent transformation that introduces significant strain, such as strain indicating a failure point of a material, structure, or component.

Thus, the present disclosure provides in certain aspects, a stretchable electrically conductive composite material that comprises a polymer and a plurality of conductive nanoparticles. The polymer may be an elastomeric or thermoplastic polymer and in certain aspects, may have a strain equal to or exceeding about 50%, and in certain aspects, optionally with a strain limit of greater than or equal to about 100%, as will be described in greater detail below. The high conductivity and stretchability of the inventive materials can be obtained by using nanoparticles having small aspect ratios, as compared to conventional carbon nanotubes that have very high aspect ratios. The inventive composite material is capable of a self-assembly process for the nanoparticles in the material, as it being stretched. This is important to achieving the high conductivity at high strains that is realized by various embodiments of the inventive technology.

A "nanoparticle" is a solid or semi-solid material that can have a variety of shapes or morphologies, however, which are generally understood by those of skill in the art to mean that the particle has at least one spatial dimension that is less than or equal to about 10 µm (10,000 nm). In various aspects, a nanoparticle is understood to have a low aspect ratio (AR) (defined as a length of the longest axis divided by diameter of the component) of typically less than or equal to about 10, and in certain preferred variations, equal to about 1.

In certain preferred variations, a nanoparticle's longest dimension is less than or equal to about 100 nm. In certain aspects, a nanoparticle has at least one spatial dimension that is greater than or equal to about 10 nm and less than or equal to about 100 nm. In certain embodiments, the nanoparticles selected for inclusion in the stretchable electrically conductive composite material comprise substantially round-shaped nanoparticles. "Substantially round-shaped" includes nanoparticles having low aspect ratios as defined above and also having a morphology or shape including spherical, spheroidal, hemispherical, disk, globular, annular, toroidal, cylindrical, discoid, domical, egg-shaped, elliptical, orbed, oval, and the like. In certain preferred variations, the morphology of the nanoparticle has a spherical shape.

Furthermore, in certain aspects, a particularly suitable nanoparticle for use in accordance with the present teachings and has a particle size (an average diameter for the plurality of nanoparticles present) of greater than or equal to about 10 nm to less than or equal to about 100 nm. In certain variations, the nanoparticle has an average particle size diameter of greater than or equal to about 5 nm to less than or equal to about 50 nm; optionally greater than or equal to about 10 nm to less than or equal to about 50 nm, and in certain variations, optionally greater than or equal to about 10 nm to less than or equal to about 30 nm. The conductive nanoparticles may be formed of a variety of conductive materials including metallic and semiconducting nanoscale particles with dimensions generally below about 100 nm. The nanoparticles may comprise gold, silver, copper, nickel, iron, carbon, platinum, silicon, cadmium, mercury, lead, molybdenum, iron, and alloys or compounds thereof. Thus, suitable nanoparticles can be exemplified by, but are not limited to, nanoparticles of gold, silver, copper, nickel, iron, carbon, platinum, silicon, CdTe, CdSe, CdS, HgTe, HgSe, HgS, PbTe, PbSe, PbS, $MoS_2$, $FeS_2$, FeS, FeSe, and other similar materials known to those of skill in the art. In certain preferred variations, however; the plurality of nanoparticles comprises gold nanoparticles. In other alternative variations, the nanoparticles can be selected from the group consisting of: silver, copper, nickel, carbon, as well as a variety of semiconductors listed above, and any combinations thereof.

In various aspects, such a stretchable composite material exhibits an electrical conductivity of greater than or equal to about 500 $Scm^{-1}$ at a tensile strain of greater than or equal to about 15%. In certain preferred variations, the plurality of conductive nanoparticles comprises gold nanoparticles. In certain variations, the polymer comprises polyurethane.

Conventional plain gold films are highly conductive, yet barely stretchable. However, by incorporating gold nanoparticles into a polymer matrix in accordance with certain aspects of the present teachings, highly conductive elastic composite materials are obtained capable of withstanding significant tensile strain.

As noted above, the molecular mechanisms underlying deformation and stiffening make combining high stretchability and conductivity in a material fundamentally difficult. Conventional best known stretchable conductors partially overcome these problems by using percolated networks from high aspect ratio nanotubes and/or nanowires. Surprisingly, however, it is demonstrated in accordance with the inventive technology that excellent stretchable conductor materials can be made from spherical conductive nanoparticles, despite their minimal aspect ratio.

In accordance with certain variations of the present teachings, stretchable electrically conductive nanoparticle composites can be made by two distinct methods. In one variation, the stretchable electrically conductive composite material is made by a layer-by-layer assembly (LBL) technique, while in a second variation, the stretchable electrically conductive composite material is made by vacuum-assisted flocculation (VAF). In certain variations, electrical conductivity for stretchable electrically conductive composite materials made by the LBL methods is as high as 11,000 S cm$^{-1}$ at 0% tensile strain (in a quiescent state) and as high as 2,400 S cm$^{-1}$ at 110% strain (in a deformed state). In other variations, electrical conductivity for stretchable electrically conductive composite materials made by the VAF methods of the present teachings is believed to achieve record high conductivities of 35 S cm$^{-1}$ at about 480% tensile strain. While not limiting the present teachings to any particular theory, these unexpectedly superior properties are believed to originate from dynamic self-organization of nanoparticles under stress and reconfigurable conducting pathways. The self-assembly processes and highly efficient charge transport make nanoparticle composites according to certain variations of the inventive technology similar to liquid metals. These inventive materials represent a new approach to nanoscale engineering of stretchable conductors and enable a new generation of flexible electronics and implantable devices.

As background to the development of the inventive materials and methods for making them, a discussion of molecular mechanisms underlying conventional material stretchability and electrical conductivity is discussed herein. Materials combining high stretchability and electrical conductivity are much needed, but pose fundamental difficulties to realize. Macroscale stretching of solids causes elongation and bending of chemical bonds. Such deformations lead to reduced overlap and delocalization of electronic orbitals as well as degeneration of conduction pathways required for electronic conduction. As such, conductivity for 130-150% tensile strain decreases significantly by 5-280 times, even for conventional stretchable conductor materials. Besides deformable solids, the dilemma between conductivity and stretchability can also be observed in liquid metals. In liquid metals, efficient electron transport pathways are retained upon large deformation of shape, but liquid metals cannot be stretched because interatomic bonds are not strong enough.

Thus, successful combination of stretchability and conductivity has been attempted using several materials engineering approaches. Conventional nanoscale conductive elements incorporate conductive particles with high aspect ratios, such as carbon nanotubes (CNTs) or nanowires (NWs). In certain aspects, a high aspect ratio (AR) (as discussed above as being defined as a length of the longest axis divided by diameter of the component) is typically greater than 25 to greater than or equal to 100. Thus, high aspect ratio components include tubes, wires, filaments, fibers, and the like. High aspect ratio CNTs or NWs have been deposited on or incorporated into elastic polymers resulting in low percolation threshold ($P_c$). Stretchable conductors from CNTs usually have $P_c$ below 1.0 vol. %. When single-walled carbon nanotubes with an aspect ratio as high as 300,000 (>1 mm in length) are finely dispersed in fluorinated copolymer matrix, a constant conductivity ($\sigma$) of 50 S cm$^{-1}$ is maintained for tensile strains ($\in$) as high as 60%. Typically though, 60% tensile strain of CNT composites results in 25 times reduction of conductivity and 140% strain results in 280 times reduction of conductivity down to 20 S cm$^{-1}$. For some of the best currently available conventional stretchable conducting composites, 150% strain amounts to 5 times reduction of conductivity to 2200 S cm$^{-1}$. In a different conventional stretchable conductor material, 130% strain is accompanied by 10 times reduction of conductivity to 6 S cm$^{-1}$. Reaching density of percolation pathways similar to that in metals generally requires further increases in CNT contents in composite materials. However, extensive research on different composites indicates that high volume content of CNTs or other high aspect ratio particles results in indubitable stiffening, and therefore, in the undesirable loss of stretchability.

For these reasons, the present technology instead uses an alternative approach to conventional high aspect ratio particles to make highly stretchable conductors. The present technology employs nanoparticles in a polymer composite. Initially, nanoparticles (NPs) would appear to be unfavorable candidates for this technology. First of all, spherical NPs have $P_c$ 10-100 times higher than high aspect ratio nanoscale components. Also, charge transport between NPs involves a large number of NP-NP junctions resulting in high contact resistance and charge carriers scattering. Additionally, NPs with strong attraction to polymers could potentially cause stiffening related to the high interfacial area. However, it has been surprisingly discovered in accordance with the present disclosure that in contrast to the apparent issues, NPs in a polymer matrix represent a more dynamic system that has greater freedom for reversible nanoscale restructuring important for stretchability. Although NP dynamics in polymer matrix at high stress/strain levels is not well understood, greater matrix mobility appears to occur from low aspect ratio NPs than high aspect ratio particles, like CNTs/NWs. Thus, the conducting pathways lost upon deformation can potentially be recovered in a different particle configuration when a plurality of NPs is employed in the composite. Also important, the conductance between two NPs does not depend on their mutual orientation.

As noted above, improved highly stretchable and electrically conductive conductor materials are desired for diverse technological areas. Flexible electronics, neuroprosthetic, and cardiostimulating implants, responsive curvilinear systems, advanced skins for robotics, and other applications require materials with increasingly high conductivity over increasingly large strains. For example, materials with electrical conductivity of about 10 S cm$^{-1}$ and a maximum tensile strength ($\in_{max}$) of 100% are required for new antistatic skins. However, for more advanced and performance-hungry devices, such as neuroprosthetic implants or stretchable displays, it would be desirable to have materials with conductivities 10,000 times higher (e.g., approaching the conductivities in metals (10$^5$ S cm$^{-9}$), while retaining strains of over 100%.

Therefore, according to various aspects of the inventive technology, conductive nanoparticles, such as gold nanoparticles, are a particularly desirable alternative to carbon nanotubes and/or nanowires having high aspect ratios. For example, gold nanoparticles provide greater matrix mobility and hence greater overall elasticity, as compared to CNTs and nanowires that are tangled within the polymeric matrix. When stretched, nanoparticles can adopt different configurations that still facilitate electron transport through the bulk of the composite material.

Thus, in certain variations, the present disclosure provides a stretchable composite material that comprises an elastic polymer having a maximum strain of greater than or equal to about 50%; optionally greater than or equal to about 75%, and in certain embodiments, greater than or equal to about 100%. The stretchable composite material also comprises a plurality of conductive nanoparticles, as described previously above. Such a stretchable composite material exhibits an electrical conductivity of greater than or equal to about 500 $Scm^{-1}$ at a tensile strain of greater than or equal to about 15%. In certain aspects, the plurality of conductive nanoparticles comprises gold nanoparticles. In certain variations, the plurality of conductive nanoparticles are present at greater than or equal to about 15 volume % to less than or equal to about 30 volume % of the total volume of the stretchable composite material.

The stretchable composite material may exhibit an electrical conductivity of greater than or equal to about 500 $Scm^{-1}$ at a tensile strain of 0% (quiescent state). In certain variations, the stretchable composite material may exhibit an electrical conductivity of greater than or equal to about 510 $Scm^{-1}$ at a tensile strain of 0% (quiescent state). In certain embodiments, the stretchable electrically conductive composite material may exhibit an electrical conductivity of greater than or equal to about 600 $Scm^{-1}$ at a tensile strain of 0% (quiescent state); optionally an electrical conductivity of greater than or equal to about 700 $Scm^{-1}$; optionally an electrical conductivity of greater than or equal to about 800 $Scm^{-1}$; optionally an electrical conductivity of greater than or equal to about 900 $Scm^{-1}$; optionally an electrical conductivity of greater than or equal to about 1,000 $Scm^{-1}$; optionally an electrical conductivity of greater than or equal to about 1,500 $Scm^{-1}$; optionally an electrical conductivity of greater than or equal to about 2,000 $Scm^{-1}$; optionally an electrical conductivity of greater than or equal to about 2,500 $Scm^{-1}$; optionally an electrical conductivity of greater than or equal to about 3,000 $Scm^{-1}$; optionally an electrical conductivity of greater than or equal to about 3,500 $Scm^{-1}$; optionally an electrical conductivity of greater than or equal to about 4,000 $Scm^{-1}$; optionally an electrical conductivity of greater than or equal to about 4,500 $Scm^{-1}$; optionally an electrical conductivity of greater than or equal to about 5,000 $Scm^{-1}$; optionally an electrical conductivity of greater than or equal to about 5,500 $Scm^{-1}$; optionally an electrical conductivity of greater than or equal to about 6,000 $Scm^{-1}$; optionally an electrical conductivity of greater than or equal to about 6,500 $Scm^{-1}$; optionally an electrical conductivity of greater than or equal to about 6,700 $Scm^{-1}$; optionally an electrical conductivity of greater than or equal to about 6,750 $Scm^{-1}$ at a tensile strain of 0%. In certain embodiments, the stretchable electrically conductive composite material may exhibit an electrical conductivity of greater than or equal to about 6,800 $Scm^{-1}$ at a tensile strain of 0% (quiescent state).

The stretchable composite material according to certain aspects of the present disclosure may also have a maximum tensile strain of greater than or equal to about 10% (maximum deformation). In certain embodiments, a maximum tensile strain of the stretchable composite material is greater than or equal to about 15% (maximum deformation); optionally the maximum tensile strain is greater than or equal to about 16%; optionally the maximum tensile strain is greater than or equal to about 20%; optionally the maximum tensile strain is greater than or equal to about 25%; optionally the maximum tensile strain is greater than or equal to about 30%; optionally the maximum tensile strain is greater than or equal to about 35%; optionally the maximum tensile strain is greater than or equal to about 40%; optionally the maximum tensile strain is greater than or equal to about 45%; optionally the maximum tensile strain is greater than or equal to about 50%; optionally the maximum tensile strain is greater than or equal to about 55%; optionally the maximum tensile strain is greater than or equal to about 60%; optionally the maximum tensile strain is greater than or equal to about 65%; optionally the maximum tensile strain is greater than or equal to about 70%; and in certain variations the maximum tensile strain is about 75%.

In yet other variations, the stretchable composite material exhibits the electrical conductivity of greater than or equal to about 510 $Scm^{-1}$ at a tensile strain of up to about 75%. Such a stretchable electrically conductive composite material may be formed by a vacuum assisted flocculation process. In other variations, the stretchable composite material exhibits an electrical conductivity of greater than or equal to about 6,800 $Scm^{-1}$ at the tensile strain of greater than or equal to about 15%. Such a stretchable electrically conductive composite material may be formed by a layer-by-layer formation process.

In certain aspects, the present disclosure provides a stretchable composite material comprising a plurality of laminated layers. Each respective layer of the plurality comprises a polymer and a plurality of conductive nanoparticles. In certain variations, the plurality of layers comprises at least two distinct layers, optionally at least three distinct layers, optionally at least four distinct layers, and in certain variations at least five distinct layers. In certain variations, the polymer comprises polyurethane and the plurality of conductive nanoparticles comprise gold. Each layer may be the same or distinct from one another in composition or method of formation. As discussed below, the consolidation of layers in a hot pressing or compression process enhances conductivity of the composite material (as compared to a single layer of conductive film) and moreover enhances tensile strength. Thus, in certain variations, the respective layers are laminated together (e.g., by compression or applying pressure, such as by rolling or pressing, optionally in the presence of heat). The lamination process for an assembly of a plurality of layers appears to further enhance the conductivity and stretchability (e.g., maximum tensile strain) of the composite material.

In certain variations, the stretchable composite material comprising the plurality of laminated layers may exhibit an electrical conductivity of greater than or equal to about 1,700 $Scm^{-1}$ at a tensile strain of 0% (quiescent state). In certain embodiments, the stretchable electrically conductive composite material may exhibit an electrical conductivity of greater than or equal to about 1,800 $Scm^{-1}$ at a tensile strain of 0% (quiescent state); optionally an electrical conductivity of greater than or equal to about 1,800 $Scm^{-1}$; optionally an electrical conductivity of greater than or equal to about 1,900 $Scm^{-1}$; optionally an electrical conductivity of greater than or equal to about 2,000 $Scm^{-1}$; optionally an electrical conductivity of greater than or equal to about 3,000 $Scm^{-1}$; optionally an electrical conductivity of greater than or equal to about 4,000 Scm$^{-1}$; optionally an electrical conductivity of greater than or equal to about 5,000 Scm$^{-1}$; optionally an electrical conductivity of greater than or equal to about 6,000 Scm$^{-1}$; optionally an electrical conductivity of greater than or equal to about 7,000 Scm$^{-1}$; optionally an electrical conductivity of greater than or equal to about 8,000 Scm$^{-1}$; optionally an electrical conductivity of greater than or equal to about 9,000 Scm$^{-1}$; optionally an electrical conductivity of greater than or equal to about 10,000 Scm$^{-1}$; optionally an electrical conductivity of greater than or equal to about 10,500 Scm$^{-1}$ at a tensile strain of 0%. In certain embodiments, the stretchable electrically conductive composite material may exhibit an electrical conductivity of greater than or equal to about 11,000 Scm$^{-1}$ at a tensile strain of 0% (quiescent state). Such a stretchable electrically conductive composite material may be formed by a layer-by-layer formation process.

In certain other embodiments, the stretchable composite material comprising the plurality of laminated layers exhibits an electrical conductivity of greater than or equal to about 1,700 Scm$^{-1}$ at a tensile strain of 0% (quiescent state) and a maximum tensile strain of the stretchable composite material is greater than or equal to about 110% (maximum deformation). In certain embodiments, the stretchable composite material comprising the plurality of laminated layers exhibits an electrical conductivity of greater than or equal to about 1,700 Scm$^{-1}$ at a tensile strain of 0% (quiescent state) and a maximum tensile strain of the stretchable composite material is greater than or equal to about 115% (maximum deformation); optionally the maximum tensile strain is greater than or equal to about 120%; optionally the maximum tensile strain is greater than or equal to about 150%; optionally the maximum tensile strain is greater than or equal to about 200%; optionally the maximum tensile strain is greater than or equal to about 250%; optionally the maximum tensile strain is greater than or equal to about 300%; optionally the maximum tensile strain is greater than or equal to about 350%; optionally the maximum tensile strain is greater than or equal to about 400%; optionally the maximum tensile strain is greater than or equal to about 450%; optionally the maximum tensile strain is greater than or equal to about 475%; optionally the maximum tensile strain is greater than or equal to about 480%; optionally the maximum tensile strain is greater than or equal to about 485%; and in certain variations the maximum tensile strain is about 486%. In certain aspects, such a stretchable electrically conductive composite material may be formed by a vacuum assisted flocculation process.

In certain other embodiments, the stretchable composite material comprising the plurality of laminated layers exhibits an electrical conductivity of greater than or equal to about 1,800 Scm$^{-1}$ at a tensile strain of 0% (quiescent state) and a maximum tensile strain of the stretchable composite material is greater than or equal to about 110% (maximum deformation). In certain embodiments, the stretchable composite material comprising the plurality of laminated layers exhibits an electrical conductivity of greater than or equal to about 1,800 Scm$^{-1}$ at a tensile strain of 0% (quiescent state) and a maximum tensile strain of the stretchable composite material is greater than or equal to about 115% (maximum deformation); optionally the maximum tensile strain is greater than or equal to about 120%; optionally the maximum tensile strain is greater than or equal to about 150%; optionally the maximum tensile strain is greater than or equal to about 200%; optionally the maximum tensile strain is greater than or equal to about 250%; optionally the maximum tensile strain is greater than or equal to about 300%; optionally the maximum tensile strain is greater than or equal to about 350%; optionally the maximum tensile strain is greater than or equal to about 400%; optionally the maximum tensile strain is greater than or equal to about 450%; optionally the maximum tensile strain is greater than or equal to about 475%; optionally the maximum tensile strain is greater than or equal to about 480%; optionally the maximum tensile strain is greater than or equal to about 485%; and in certain variations the maximum tensile strain is about 486%.

In certain variations, a stretchable composite material comprising the plurality of laminated layers exhibits an electrical conductivity of greater than or equal to about 3,500 Scm$^{-1}$ at a tensile strain of 60%. Such a stretchable electrically conductive composite material may be formed by a layer-by-layer formation process. In other variations, a stretchable composite material comprising the plurality of laminated layers exhibits an electrical conductivity of greater than or equal to about 2,400 Scm$^{-1}$ at a tensile strain of 110%. Such a stretchable electrically conductive composite material may be formed by a layer-by-layer formation process. In yet other variations, a stretchable composite material comprising the plurality of laminated layers exhibits an electrical conductivity of greater than or equal to about 210 Scm$^{-1}$ at a tensile strain of 60%. Such a stretchable electrically conductive composite material may be formed by a vacuum assisted flocculation process. In yet other variations, a stretchable composite material comprising the plurality of laminated layers exhibits an electrical conductivity of greater than or equal to about 94 Scm$^{-1}$ at a tensile strain of 110%. Such a stretchable electrically conductive composite material may be formed by a vacuum assisted flocculation process.

In certain variations, the stretchable electrically conductive composite material comprises at least five laminated layers. In certain aspects, a maximum tensile strain of the stretchable composite material is greater than or equal to about 486%. Thus, in certain variations, the stretchable composite material exhibits an electrical conductivity of greater than or equal to about 11,000 Scm$^{-1}$ when a tensile strain is 0%. In other embodiments, the stretchable composite material exhibits an electrical conductivity of greater than or equal to about 200 Scm$^{-1}$ at a tensile strain of greater than or equal to about 60%. In yet other embodiments, the stretchable composite material exhibits an electrical conductivity of greater than or equal to about 3,500 Scm$^{-1}$ at the tensile strain of greater than or equal to about 60%.

For example, the maximum conductivity of five layer composite stacks formed by layer-by-layer (5×LBL) or vacuum assisted flocculation (5×VAF) is 11,000 S cm$^{-1}$ and 1,800 S cm$^{-1}$ (FIG. 9B) for tensile strain ($\in$)=0%, respectively. A maximum tensile strain ($\in_{max}$) for 5×LBL and 5×VAF is 115% and 486%, respectively (FIGS. 9C and 9D). The conductivity of LBL and VAF composites decreases with the increase of $\in$. 60% strain results in a 2.5 times reduction of conductivity to 3,500 S cm$^{-1}$ for a 5×LBL stack assembly and 4.2 times reduction to 210 S cm$^{-1}$ for 5×VAF stack assembly. 110% strain results in as little as 3.5 times reduction to 2,400 S cm$^{-1}$ for 5×LBL and a 9.4 times reduction to 94 S cm$^{-1}$ for 5×VAF (FIG. 9E).

In certain variations, a stretchable composite material comprises polyurethane and a plurality of spherical gold nanoparticles. Such a stretchable composite material can exhibit an electrical conductivity of greater than or equal to about 510 Scm$^{-1}$ at a strain of greater than or equal to about 15%. In certain variations, citrate-stabilized gold (Au) nanoparticles are deposited via a method according to the present disclosure to provide a composite material having an overall thickness of about 1 µm. In certain variations, such a technique may involve layer-by-layer assembly or in alternative variations, a vacuum-assisted flocculation, onto polymeric substrates, such as polyurethane. In this regard, electrical conductivities as high as 11,000 Scm$^{-1}$ and 2400 Scm$^{-1}$ may be realized for quiescent (0% strain) and deformed states (110% strain), respectively. Thus, these materials are suitable for use in a new generation of flexible electronic devices and implantable devices, by way of non-limiting example.

In one embodiment of the present disclosure, a stretchable electrically conductive composite material is made by a layer-by-layer assembly (LBL) technique. See FIGS. 1A-1B. Layer-by-layer assembly (LBL) provides a reliable method for fabricating polymer composites with favorable physical characteristics for the inventive technology. The LBL technique is well known and relies on alternating adsorption of charged species or polyelectrolytes onto a substrate. Layers are built up by sequential dipping of a substrate into oppositely charged solutions having oppositely charged moieties that are attracted to the surface. Monolayers of individual components attracted to each other by electrostatic and van-der-Waals interactions are thus sequentially adsorbed on the substrate. LBL films can be constructed on a variety of solid substrates, thus imparting much flexibility for size, geometry and shape and further patterned or etched (with chemicals, plasma, electron beam, or high intensity lasers, for example). Further, the LBL composite films may be detached from the substrate to form an independent material. Additionally, LBL multilayers have both ionic and electronic conductivity that provides favorable charge transfer characteristics.

Figure 1A:
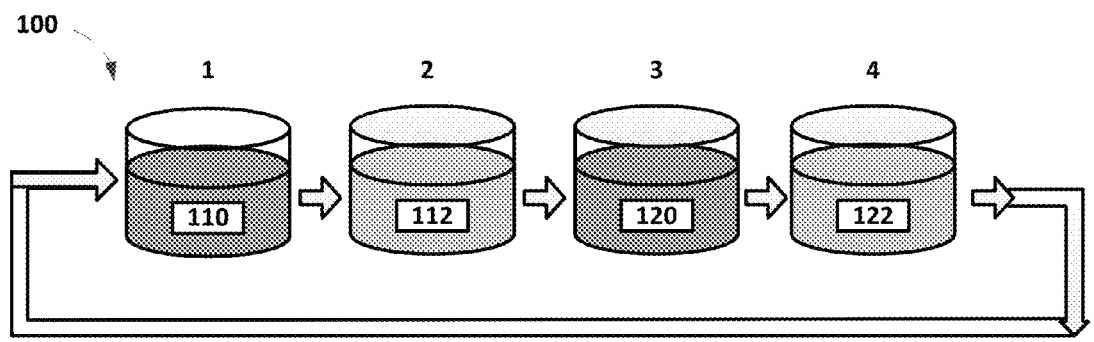
FIGS. 1A-1B show a method for forming a stretchable electrically conductive composite material via a layer-by-layer process according to certain aspects of the present disclosure. The process steps are shown in FIG. 1A, while a sectional schematic view of a layer of a stretchable electrically conductive composite material being formed is shown in FIG. 1B.
Figure 1B:
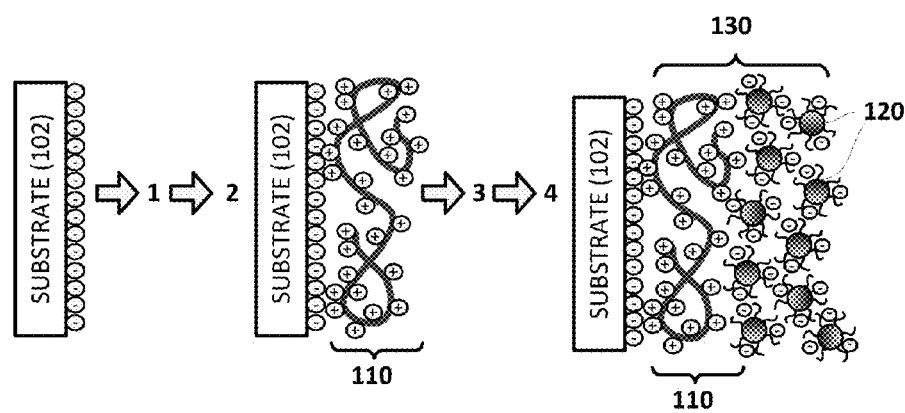

In an exemplary LBL method 100, a substrate 102 has a first charge. A first charged material or moiety 110 has a first polarity that is opposite to the charge of the substrate 102. As shown in FIGS. 1A-1B, the substrate 102 has a negative charge, while the first charged material 110 has a positive charge. The first charged material 110 is thus applied to substrate 102 in Step 1, for example, by dipping the substrate 102 into a bath of the first charged material 110. The driving force is electrostatic attraction. Additional steps may occur between application steps, such as washing of the surface before application of the next material. As shown in FIG. 1A, after application of the first charged material 110 to the substrate 102, the surface of the substrate 102 can be exposed to a first wash material 112 in Step 2, which is an optional step. Then, a second charged material or moiety 120 having a second polarity opposite from the first polarity is applied over the first charged material 110 in Step 3. Then, the surface having both the first charged material 110 and the second charged material 120 disposed thereon can be exposed to a second wash material 122 in Step 4, which like Step 2 is likewise optional.

Steps 1-4 serve as a single deposition cycle that may be repeated sequentially to build distinct alternating layers of the first charged material 110 and second charged material 120. A composite material layer 130 comprises the first charged material 110 and the second charged material 120. Depending on the charge of the substrate 102, the first charged material 110 may be either a polycation or a polyanion (so that it is attracted to and deposited onto the surface of the substrate). Thus, the second charged material 120 is the other of the polycation or the polyanion, having an opposite charge to the first charged material 110. Accordingly, a composite material formed by LBL is often referred to as: (polyanion/polycation)$_n$, where n represents the number of deposition cycles or layers present. LBL thus provides a simple tool for making thin film composite structures having homogeneously dispersed, well organized layered structures with high levels of both polyanion and polycation.

In certain aspects of the present disclosure, a first charged material or moiety 110 is a polycation in the form of a polyurethane (PU) having two sets of 28 repeating units of ductile moieties (FIG. 2A). The polyurethane has a strong positive charge that is complementary to the negative charge of NPs and permits layer-by-layer (LBL) deposition to make corresponding stretchable electrically conductive composite materials. The second charged material is a polyanion comprises a citrate-coated gold nanoparticle. The anionic citrate is shown in FIG. 2B. A thin citrate layer on the surface of the gold nanoparticles (NPs) makes them negatively charged. Citrate coating is believed to only present a minimal barrier for charge transfer. Of course, other coatings on metal nanoparticles are likewise contemplated. In certain variations, a citrate-stabilized 13.0±0.3 nm diameter gold (Au) nanoparticle (NP) is employed as the polyanion (shown in FIGS. 3A and 3B). The polyurethane is used as a polymeric partner for the gold NPs (1 vol. % aqueous solution). The use of such a layer-by-layer technique (LBL) permits (a) high NP loadings in the composite, (b) maintenance of uniformity of NP distribution throughout the polymeric material, and (c) ability to make adequate comparisons between composites with different nanoscale fillers.

After removal of the substrate, free-standing composite films are thus obtained after 500 LBL deposition cycles and denoted as (PU/NP)$_{500}$. Their respectively thickness is determined by scanning electron microscopy (SEM) to be about 2.0±0.2 µm. Ellipsometric thickness for 1-10 bilayers gives a total thickness of about 1.97 µm for 500 bilayers (FIG. 4A). It is nearly identical to the SEM thickness detected, which indicates excellent linearity of the LBL growth.

In yet other variations of the present teachings, stretchable electrically conductive composite material may be made by vacuum-assisted flocculation (VAF). In FIG. 5, such a VAF process 200 starts with a suspension 210 of a first charged material or moiety 212. A flocculent is typically a charged material or moiety to be flocculated, which can be mixed with a fluid. As shown in FIG. 5, the suspension 210 includes the plurality of nanoparticles 212 suspended in a liquid medium. In Step 1, a second charged material or moiety 214 (having a second polarity opposite from the first polarity) is introduced to the suspension 210 comprising the first charged material 212. As shown in Step 1 of FIG. 5, droplets 216 of the second charged material 214 are dispersed into the suspension 210. When the second charged material 214 is introduced, the flocculent 212 having the first charge attracts the oppositely charged second material 214. As they come together after Step 2, the first and second materials 212, 214 agglomerate and build increasingly larger particles until they start to settle out of the fluid (floc) 230. A composite material is formed by a single layer 230 of flocculated materials and comprises both the first and second charged materials 212,214.

In certain aspects, flocculation can employ charged polymers to form bridges between the flocs and bind the particles into large agglomerates or clumps that ultimately may form a continuous layer of material (e.g., layer 230). Bridging occurs when segments of the polymer chain adsorb on different particles and help particles aggregate. Once suspended particles are flocculated into larger particles or layers of materials, they can usually be removed from the liquid by sedimentation, provided that a sufficient density difference exists between the suspended matter and the fluid/liquid.

Such particles can also be removed or separated by media filtration, straining or flotation. In certain aspects, the process of flocculation can be conducted under vacuum conditions or sub-atmospheric pressure to expedite processing and enhance separation—vacuum assisted flocculation (VAF). The flocculation process may be repeated sequentially to form a plurality of layers 230 of the composite material. VAF thus provides yet another simple tool for making thin film composite structures by using electrostatic forces as a driving attraction to form randomly dispersed layered structures.

In certain aspects of the present disclosure, the first and second charged species 212, 214 may be the same as those discussed above in the context of the LBL pairs. Thus, a first charged material or moiety 212 for VAF processing can be a negatively charged polyanion comprises a citrate-coated gold nanoparticle suspended in water or other liquid solvents/vehicles. A second charged material 214 may be the positively charged polyurethane (PU) having two sets of 28 repeating units of ductile moieties (FIG. 2A). As noted above, the polyurethane has a strong positive charge, which when added to the suspension 210 comprising the negatively charge gold NPs, promotes flocculation of aggregated particles 212 that settle to form a composite layer 230 comprising PU and gold NPs having a random distribution.

This serves as a single deposition cycle that may be repeated sequentially to build distinct alternating layers 230 comprising the first charged material 212 and second charged material 214. Like in LBL, the driving force is electrostatic attraction for VAF. Additional steps not shown may occur between application steps, such as washing of the surface before application of the next material. Like in LBL, depending on the charge of the substrate, the first charged material 212 may be either a polycation or a polyanion. Thus, the second charged material 214 is the other of the polycation or the polyanion, opposite in charge to the first charged material 212. After formation of a composite material, it can be removed from the liquid of the suspension 210 and dried or further processed.

In certain alternative aspects, the present disclosure contemplates a stretchable electrically conductive composite material that is used as an optical plasmonic film. For example, in certain aspects, such stretchable electrically conductive composite materials have chirality and thus can be used as reversibly tunable chiroptical thin films. Control of chiroptical property in a visible region (e.g., in a visible portion of the electromagnetic spectrum) has been of growing focus, especially for biosensing and optoelectronic devices. However, most conventional chiral materials reported present monotonous optical responses fixed from their determined structures. Further, design of nanostructures with tailored properties mainly uses two fabrication techniques, either three dimensional (3-D) arrangement of nanoparticles (NPs) in a helical fashion using biomolecules or alternatively evaporation of plasmonic materials onto a tilted wafer. However, complex preparation steps and long-term stability of resultant colloids introduce uncertainty with respect to engineering applications for such conventional materials.

However, the inventive stretchable electrically conductive composite chiral plasmonic thin films have capability for reversibly tunable chiroptical response in a visible range. Such stretchable electrically conductive composite materials for use as chiral plasmonic thin films comprise a polymer and a plurality of conductive nanoparticles. The stretchable composite material used as chiral plasmonic films may be any of those previously described. In certain variations, the stretchable composite material used as a chiral plasmonic material comprises polyurethane and a plurality of spherical gold nanoparticles.

The stretchable composite material used as chiral plasmonic films may be fabricated by any of the techniques discussed above. To introduce chirality to a stretchable composite material to form the chiral plasmonic material, one or more layers of polymer/nanoparticle pairs may be formed on a pre-twisted elastic substrate. By "twisted" it is meant that a substrate has been rotated along a major axis (e.g., a longitudinal axis). The twisting of the substrate may be in a clockwise or counter-clockwise rotational orientation (along a major axis of the substrate). When the substrate (and film formed) are elastic and stretchable, they return from the deformed or twisted state to a relaxed or flat state. Thus, assemblies of conductive metallic nanoparticles/nanostructures with chirality or handedness exhibit strong chiroptical properties in the visible and near-infrared electromagnetic spectrum ranges, due to plasmonic resonance coupling.

In certain variations, the stretchable composite chiral plasmonic materials are fabricated from polymer (e.g., polyurethane (PU)) and nanoparticles (e.g., gold nanoparticles, AuNPs) using layer-by-layer (LBL) method deposited on a pre-twisted elastic substrate. After releasing the substrate from twisting, the polymer/nanoparticle (PU/AuNP) films experience buckling resulting in 3-dimensional twisted alignments of the nanoparticles (AuNPs). The chiroptical properties can be tailored by controlling certain parameters, such as size, shape, composition of, and distance between nanoparticles and their geometries.

The mirrored twisted alignments of conductive nanoparticles (Au NPs) in chiral plasmonic films can produce opposite signed circular dichroism (CD) spectra ranging from about 400 nm to about 800 nm, by way of example. Also, post-stretching with 50% of strain can amplify optical response up to 10 times and blueshift signals up to about 73 nm. As discussed further herein, simulation supports the fact that modulating chiroptical properties originates from a change of structural alignment of conductive nanoparticles (e.g., Au NPs) in plasmonic films. It should be noted that the macro-scale twisting of a substrate with different handedness (clockwise and counter-clockwise to form left handed chirality or right handed chirality) can be successfully transferred into the nano-scale alignment of nanoparticles (e.g., AuNPs) showing desired handedness of optical activity. Moreover, such a formation technique has an advantage in controllability and reversibility, which was not possible in conventional techniques for forming plasmonic films, such as nano-lithography or oblique deposition.

Strong and tailorable chiroptical properties in the visible range can lead to the very interesting and previously unseen optical applications, such as sensors for detection of biomolecules or of specific light, or negative refractive index materials. Reversibly fine-tuning chiroptical properties (handedness, intensity and location of peak) in the visible range is possible by simple control of mechanical stress in a solid-state form, rather than complex form of phase changes in the liquid-state. Such stretchable composite material used as chiral films according to certain aspects of the present technology are contemplated for use in spectral filters, switches, or advanced sensors with increased sensitivity and selectivity, as well as incorporation into flexible electronics. The technology of the present disclosure will greatly expand the current boundaries of chiral and metamaterials to various applications, including biochemistry, optics, and electronics, by way of non-limiting example. As discussed further herein in the examples, reversible change of chirality is demonstrated from assemblies of plasmonic nanomaterials and helical molecules driven by temperature changes. Such a technology is advantageous in providing responsiveness to various external stresses and simplified architectures, without requiring any assistance from chiral biomolecules/templates as in conventional materials.

Thus, in certain aspects, the present disclosure contemplates a stretchable composite chiral plasmonic material that comprises a twisted film comprising an elastic polymer having a maximum strain of greater than or equal to about 50%. The stretchable composite chiral plasmonic material also comprises a plurality of nanoparticles dispersed in the elastic polymer. The twisted film has either a left handed chirality or a right handed chirality based on a rotational direction of the twisted film (in other words, if a rotation of direction of the film as it twists is counter-clockwise, then the chirality is right handed, while a clockwise rotation of the film forms a left handed chirality). In certain aspects, the twisted film is capable of reversibly transitioning from a first twisted state to a second relaxed state to control chiroptical properties of the stretchable composite chiral plasmonic material. Thus, the chiroptical properties of a twisted film can advantageously be controlled by modifying an amount of mechanical strain.

In certain aspects, the twisted film is capable of reversible uniaxial mechanical stretching from 0% to less than or equal to about 50% to modify chiroptical properties of the stretchable composite chiral plasmonic material. As noted above, the stretchable composite chiral plasmonic material may be any of those described previously above in the context of other embodiments. Thus, a plurality of nanoparticles may have a maximum dimension of less than or equal to about 100 nm and in certain aspects, may be selected from the group consisting of: gold, silver, copper, nickel, iron, carbon, platinum, silicon, CdTe, CdSe, CdS, HgTe, HgSe, HgS, PbTe, PbSe, PbS, $MoS_2$, $FeS_2$, FeS, FeSe, and combinations thereof. In certain preferred variations, the plurality of nanoparticles comprises gold nanoparticles, while the polymer comprises polyurethane. The plurality of nanoparticles are present at greater than or equal to about 15 volume % to less than or equal to about 30 volume % of the total volume of the stretchable composite chiral plasmonic material.

The stretchable composite chiral plasmonic material may have any of the electrical conductivities at the strain rates specified above. Furthermore, the stretchable composite chiral plasmonic material is capable of producing opposite signed circular dichroism (CD) spectra ranging from greater than or equal to about 400 nm to less than or equal to about 800 nm. In various aspects, the opposite signed CD signals are substantially symmetric. Circular dichroism (CD) is differential absorption of left and right circularly polarized light. G-factor is the value of CD divided by its absorbance. G-factor is normally used as a metric that shows strength of chiroptical activities, as discussed herein.

In certain other aspects, the present disclosure contemplates applying a first charged material having a first polarity to a substrate, which may be elastic. The substrate is rotationally twisted and has a second polarity opposite to the first polarity. Then a second charged material having the second polarity is applied over the first charged material in a layer-by-layer process, where the first charged material and the second charged material are distinct from one another and selected from a polymer and a plurality of conductive nanoparticles. Then, the first charged material and the second charged material can be removed from the twisted substrate. The first and second charged materials can be permitted to relax from a first twisted state (while on the twisted substrate) to a second relaxed state, which facilitates buckling of the plasmonic film, either before or after removal from the twisted substrate. The first charged material and the second charged material together define at least one layer of a composite material that is a twisted film with either a left handed chirality or a right handed chirality based on a rotational direction of the twisted substrate and thus of the plasmonic film (in other words, if a rotation of direction of the twisted film is counter-clockwise then the chirality is right handed, while a clockwise rotation of the twisted film forms a left handed chirality). In certain aspects, the twisted film is capable of reversibly transitioning from a first twisted state to a second relaxed state to control chiroptical properties of the stretchable composite chiral plasmonic material. When the twisted film is initially removed from the twisted substrate and relaxes, buckling occurs in the film as it relaxes and creates irreversible chirality. However, the film is capable of further additional reversible mechanical strain that can re-twist or stretch the material to control the chiroptical properties of the stretchable composite chiral plasmonic material. Thus, the plasmonic film can be mechanically transitioned from a first twisted state to a second relaxed state to control chiroptical properties of the stretchable composite chiral plasmonic material. Hence, the chiroptical properties of a twisted film can advantageously be controlled by modifying an amount of mechanical strain applied thereto.

The methods may further comprise forming a plurality of layers of the composite material that will define the film by repeated sequential applying of the first charged material and the second charged material before the removing of the first charged material and the second charged material from the twisted substrate. Any of the embodiments of stretchable composite materials discussed previously can be used in such embodiments. In certain preferred aspects, the first charged material is a positively-charged polyurethane and the second charged material is a plurality of gold nanoparticles having a negatively-charged surface layer.

In certain other aspects, the present disclosure also contemplates medical devices that comprise the stretchable electrically conductive composite materials comprising a polymer and a plurality of conductive nanoparticles. In certain variations, the polymer and the nanoparticles are biocompatible and capable of introduction and/or implantation within an organism, such as an animal. A medical device includes any device that may be implanted temporarily or permanently in a human or other animal. The stretchable electrically conductive composite materials of the present disclosure are particularly suitable for medical devices that require an ability to remain electrically conductive while stretching or flexing. For example, the stretchable electrically conductive composite materials are particularly suitable for catheter-based surgeries. Examples of medical devices include, but are not limited to, angioplasty balloons, dilatation balloons, ablation balloons, stents, expandable stents, such as balloon-expandable stents, coronary stents, peripheral stents, stent-grafts, catheters, other expandable tubular devices for various bodily lumen or orifices, grafts, vascular grafts, arteriovenous grafts, by-pass grafts, pacemakers and defibrillators, leads and electrodes for the preceding, patent foramen ovale closure devices, artificial heart valves, anastomotic clips, arterial closure devices, cerebrospinal fluid shunts. In typical catheter-based surgeries, a balloon catheter is inserted (often through a brachial or femoral artery) in a deflated state, positioned within a body structure to be opened, ablated, or otherwise treated, unsheathed and inflated, electrically activated, and then deflated and removed. For example, in one illustrative example, a balloon catheter is inserted percutaneously and/or intravascularly to a treatment location for renal ablation using a guidewire, a guide catheter or other conventional means. Once in position, the balloon is inflated, typically to an extent that one or more electrodes are in contact with or immediately adjacent a vessel wall (having a nerve to be modulated or ablated). The one or more electrodes may be used to map the location for treatment, or a separate component of the medical device may be used for this purpose prior to placement of the balloon. For treatment, the one or more electrodes are activated and energy (e.g., RF energy) is transmitted into the adjacent tissue (e.g., for ablation or modulation of nerves). The balloon is then deflated and removed. A similar procedure occurs during angioplasty, where the balloon is positioned within a blocked or occluded lumen/vasculature, inflated to create an opening, and then deflated and withdrawn. Thus, the medical device may be intended for any vessel in an animal, including cardiac, renal, neurological, carotid, venal, coronary, aortic, iliac, femoral, popliteal vasculature, and urethral passages, by way of non-limiting example.

In certain aspects, a medical device according to the present technology can be designed for the localized delivery of a therapeutic or biofunctional agent. Moreover, the stretchable electrically conductive composite material may include one or more biofunctional agents in addition to the polymer and nanoparticles that can be released or interact with a localized environment in vivo. Suitable therapeutic or biofunctional agents include by way of non-limiting example, drugs, such as anti-rejection drugs; anti-thrombotic agents; anti-coagulants; anti-inflammatory agents; non-steroidal anti-inflammatory agents (NSAIDs); COX-I and II inhibitors; antimicrobial agents; antiviral agents; antifungal agents; antibiotics; anti-proliferative agents; anti-neoplastic/antiproliferative/anti-miotic agents; anesthetic, analgesic or pain-killing agents; antipyretic agents, prostaglandin inhibitors; platelet inhibitors; DNA de-methylating agents; cholesterol-lowering agents; vasodilating agents; endogenous vasoactive interference agents; angiogenic substances; cardiac failure active ingredients; targeting toxin agents; stem cell or gene therapies; antioxidants; free radical scavengers; nutrients; co-enzymes; ligands; cell adhesion peptides; peptides; proteins; nucleic acids; DNA; RNA; polysaccharides; sugars; nutrients; hormones; antibodies; immunomodulating agents; growth factors; growth factor receptors; transcriptional activators; translational promoters; anti-proliferative agents; growth hormones; growth factor inhibitors; growth factor receptor antagonists; transcriptional repressors; translational repressors; replication inhibitors; inhibitory antibodies; hormonal agonists; hormonal antagonists; inhibitors of hormone biosynthesis and processing; antigestagens; antiandrogens; aptamers; quantum dots; nano-materials; nano-crystals; and combinations thereof.

As noted above, in certain variations, a balloon catheter for nerve modulation, ablation, angioplasty, or other surgical procedures comprises a stretchable electrically conductive composite material and can be used for catheter-based surgeries, such as renal denervation, cardiac ablation, or angioplasty. In certain preferred variations, the stretchable electrically conductive composite materials are fabricated from polymer (e.g., polyurethane (PU)) and nanoparticles (e.g., gold nanoparticles, AuNPs), which are biocompatible materials. In various aspects, the polymer is an elastic polymer having a maximum strain of greater than or equal to about 50%, as described previously above.

By way of example, FIG. 30 shows a simplified schematic of a catheter medical device 350 comprising a catheter shaft 360 (having an internal lumen, not shown) with an inflatable balloon 370 disposed thereon. The inflatable balloon 370 comprises a stretchable substrate material 372 capable of expanding when inflated to contact one or more regions of a wall of a blood vessel or other body structure. The stretchable substrate material 372 is also capable of collapsing to a low profile when deflated. Some exemplary suitable materials for the stretchable substrate material 372 include polymers, including elastomeric materials. Examples of suitable polymeric materials include, but are not limited to, polyethylene terephthalate (PET), polyurethane, polytetrafluoroethylene (PTFE), polyamide (nylon), polyether, polyether block amide (PEBA), or other suitable equivalent materials, copolymers, and combinations thereof. FIG. 30 shows the stretchable substrate material 372 in an inflated and expanded state, where a central region 374 is filled (e.g., with a pressurized inflation medium delivered through a conduit (not depicted) inside catheter shaft 360). Notably, the stretchable substrate material 372 of catheter balloon 370 may have a variety of different shapes and is not limited to the exemplary cylindrical shape shown in FIG. 30.

In accordance with certain aspects of the present disclosure, a stretchable electrically conductive composite material 380 is disposed on an external surface 376 of the stretchable substrate material 372. The stretchable electrically conductive composite material 380 comprises a polymer (e.g., polyurethane (PU)) and a plurality of nanoparticles (e.g., gold nanoparticles, AuNPs). The stretchable electrically conductive composite material 380 can be applied over the stretchable substrate material 372 to form a coating thereon by using a layer-by-layer (LBL) method described above. The stretchable electrically conductive composite material 380 thus serves as an electrode of the inflatable balloon 370. While not shown, one or more regions of the stretchable electrically conductive composite material 380 can be in electrical communication with various wires or other components disposed within a lumen of catheter shaft 360 to deliver electrical current or potential, as is well known in the catheter arts. While the stretchable electrically conductive composite material 380 can be applied to the entire external surface 376 of the stretchable substrate material 372, it is also contemplated that the stretchable electrically conductive composite material 380 may be applied in discrete regions (either continuous or non-continuous regions on the surface) to define a predetermined surface pattern.

In various aspects, a medical device may be processed according to the present disclosure by applying a stretchable electrically conductive composite material made by a layer-by-layer assembly (LBL) technique, as previously described above. Thus, the medical device comprises a stretchable substrate (which may be an inflatable balloon, like stretchable substrate material 372 in FIG. 30), which may have a first charge or may be treated or activated to have a first charge by conventional and known processes. A first charged material has a first polarity that is opposite to the charge of the substrate. Then, a second charged material having a third charge, which is the same polarity as the substrate but opposite to the polarity of the first charged material, is applied over the first charged material. The surface may be washed and the process optionally sequentially repeated to form a plurality of layers comprising the first charged material and the second charged material. In certain preferred aspects, the first charged material is a positively-charged polyurethane and the second charged material is a plurality of gold nanoparticles having a negatively-charged surface layer. The LBL technique can be carried out as standard dipping process or in a spray modality. In this regard, a stretchable electrically conductive composite material layer is formed over the substrate, which can be configured to be in electrical communication with an energy source.

In various aspects, a stretchable electrically conductive composite material layer is deposited to provide sufficient electrical conductivity to a medical device substrate. The stretchable electrically conductive composite material may have any of the electrical conductivity levels described previously above. Necessary levels of electrical conductivity are well known and readily determined by those of skill in the art and may vary depending on the application and use of the medical device. In certain aspects, a stretchable electrically conductive composite material layer formed by LBL has greater than or equal to about 50 layers (each layer comprising a pair of the first charged material and the second charged material), optionally greater than or equal to about 70 layers, optionally greater than or equal to about 75 layers, optionally greater than or equal to about 80 layers, optionally greater than or equal to about 90 layers, and in certain aspects, optionally greater than or equal to about 100 layers. A stretchable electrically conductive composite material layer, including multiple layers of paired first and second materials, may have an overall thickness of greater than or equal to about 50 nm, optionally greater than or equal to about 100 nm, optionally greater than or equal to about 200 nm, optionally greater than or equal to about 300 nm, optionally greater than or equal to about 350 nm, and in certain aspects, optionally greater than or equal to about 400 nm.

In certain aspects of the present disclosure, a first charged material is a polycation in the form of a polyurethane (PU) (which as described above, has a positive charge). The second charged material may be a negatively charged citrate-coated gold nanoparticle. A stretchable electrically conductive composite material comprising gold nanoparticles thus creates a coating defining electrically conductive regions on the medical device's stretchable substrate. As noted above, in certain variations, the conductive stretchable electrically conductive composite material layers disposed on the balloons can be applied to select regions and thus the surface of the balloon is patterned to produce conducting circuits. Such patterning can be accomplished by using a removable mask on the surface of the balloon or substrate prior to deposition of the stretchable electrically conductive composite material. After the deposition process, the mask can be removed. In alternative aspects, patterning may be accomplished by first coating all of a surface of the substrate with a stretchable electrically conductive composite material, followed by depositing a protective layer over select regions of the stretchable electrically conductive composite material layer, followed by plasma etching. In other aspects, masking of the surface of the substrate can also be accomplished by depositing standard photoresists, followed by photolithography.

Certain aspects of the inventive technology may be better understood by preparation and testing of samples as described in the following non-limiting examples.

Example 1

In this example, a stretchable electrically conductive composite material is formed by a layer-by-layer process according to certain variations of the present disclosure.

As-received cationic polyurethane aqueous dispersion (PU, 30 vol. %, M. W. of approximately 92,000) (commercially available from Hepce Chem. Co., South Korea) is used after diluting to 1 vol. % solutions in deionized (DI) water. Dried films of this PU could be stretched to over ca. 450%. Microscope glass slides having dimensions of 25 mm×75 mm are used for the LBL film preparation. Hydrogen peroxide and concentrated sulfuric acid used in the piranha cleaning solution are both purchased from Sigma-Aldrich. Concentrated hydrofluoric acid (HF) is obtained from Sigma-Aldrich and a 1 vol. % HF solution used for preparation of freestanding films is prepared by diluting the stock solution with DI water.

Gold(III) chloride trihydrate ($HAuCl_4$) and sodium citrate tribasic dihydrate are obtained from Sigma-Aldrich and used as received. Citrate stabilized gold nanoparticles (Au NPs) with a diameter 13±0.3 nm are synthesized according to a slightly modified procedure described in Turkevich et al., "A Study of the Nucleation and Growth Processes in the Synthesis of Colloidal Gold," *Discuss Faraday Soc.*, Vol. 11, pp. 55-75 (1951), incorporated by reference herein. Briefly, $HAuCl_4$ (180.0 mg, 0.458 mmol) is added to ultrapure DI water (950 mL) in a 1 L glass beaker equipped with a magnetic stir bar. The mixture is heated to boil under vigorous stirring followed by additional heating for 20 min. Subsequently, 50 mL of 34 mM sodium citrate solution is added to the mixture. The aqueous solution (or suspension) is heated for 20 min followed by cooling to room temperature. In some cases, the aqueous solution/suspension is further concentrated when used as a dipping solution for forming LBL films. For the concentration process, the as-made aqueous Au NPs dispersions are transferred into 50 mL centrifuge tubes and concentration of the solutions increased via Sorvall Legend Mach 1.6R (commercially available from Thermo scientific, MA, USA) at the speed of 10,000 rpm for 1 hr. Less than 5 mL of concentrated of Au NPs solution is settled at the bottom of the tube. Supernatant of 45 mL is removed by suction pipettes, while taking special care to prevent disturbing of the sediment nanoparticles. Finally, the resultant NPs are collected to be used for LBL process.

Preparation of LBL Films

In a typical LBL assembly process, glass slides cleaned by piranha solution (3:1 of $H_2SO_4:H_2O_2$) overnight are dipped into a 1 vol. % solution of PU, for 5 min, rinsed with DI water for 1 min and gently dried with compressed air. Then they are dipped into a dispersion of concentrated Au NPs for 7 minutes, rinsed 1 minute, and again dried with compressed air. This deposition cycle constitutes one bilayer (n=1), and can be repeated n times as necessary to obtain desirable thickness. The resulting film is denoted as $(PU/NPs)_n$. Freestanding films are isolated by etching of the glass slides with 1 vol. % HF solution. After thorough rinsing with water, the detached films are dried in an oven at 60° C. overnight and then kept in ambient conditions (room temperature and relative humidity of 20-30%) for another overnight prior to measurement of properties. Conditions and procedures for preparation of LBL films with various Au contents as shown in FIG. 1A are same except dipping time to the dispersion of concentrated Au NPs. LBL films containing 15.4 vol. %, 16.2 vol. %, 16.9 vol. %, 19.4 vol. %, 21.7 vol. %, 24.0 vol. % of Au NPs are prepared with dipping times of 1 min, 2 min, 3 min, 8 min, 14 min, and 20 min, respectively.

When the substrate is dipped into the Au NPs dispersion, tiny amounts of PUs, which might be weakly bonded, are slowly diffused into dispersion of Au NPs. In the process of cyclic deposition, PUs are accumulated in the dispersion of Au NPs and when that amount is over a specific threshold, Au NPs are flocculated. To keep the homogeneity of LBL film, careful monitoring of flocculation is needed. If it is observed, the dispersion of Au NPs needs to be changed.

Example 2

In this example, a stretchable electrically conductive composite material is formed by a vacuum assisted flocculation process according to certain variations of the present disclosure is made. Components as in Example 1, unless otherwise indicated. Filter papers of 0.8 μm pore size with 47 mm diameter are used in this example with a filtration assembly obtained from Fisher Scientific for the VAF film preparation As noted above, citrate coated gold nanoparticles are formed by adding $HAuCl_4$ (180.0 mg, 0.458 mmol) to ultrapure DI water (950 mL), to which 50 mL of 34 mM sodium citrate solution is added to the mixture. The aqueous solution (or suspension) is heated for 20 min followed by cooling to room temperature. As-prepared aqueous solution (or suspension) is directly used for the preparation of VAF films.

Preparation of VAF Films

In preparing VAF composites, 1 L of as-prepared Au NPs dispersion (no additional concentration steps are applied) is introduced to a 1 L glass beaker containing equipped with a magnetic stir bar. To this aqueous dispersion, 1 mL of 1.0 vol. % aqueous PU is slowly added. The mixture is stirred for 15 min followed by filtration. The resultant gold-colored film is peeled off from the filter paper. In certain aspects, the film is completely dried before taking it out from the filtration assembly. Conditions and procedures for preparation of VAF films with various Au contents are the same except volumetric ratio of a dispersion of as-prepared Au NPs solutions. VAF films containing 15.9 vol. %, 16.4 vol. %, 17.3 vol. %, 18.0 vol. %, 19.1 vol. %, 21.0 vol. %, 21.7 vol. %, 22.8 vol. %, and 23.4 vol. % of Au NPs are prepared with 250 mL, 500 mL, 650 mL, 700 mL, 800 mL, 900 mL, 1000 mL, 1050 mL, and 1100 mL of as-prepared Au NPs dispersion, respectively. To make a 30 μm thick VAF film, total ca. 1800 mL solution needs to be filtered.

Example 3

In this example, a plurality of distinct film layers are laminated together to form a stack or assembly of consolidated layers, according to certain aspects of the present disclosure. A desired number of freestanding VAF or LBL films are stacked together and hot-pressed at 120° C. and about 20 MPa of pressure for 1 hr. Lamination temperature is chosen because no phase change is observed up to 130° C. for all materials according to DSC data (FIG. 16). Individual films peeled off have some fibrous material that came from the filter paper, thus removal of those extraneous materials is needed by gentle scratching.

Instrumental Analysis

Measurements of Conductivity

Conductivity measurements with two-probe and four-probe methods are obtained using an 34401A Digital Multimeter, 6½ Digit (Agilent Technologies, Inc., CA, USA). Measurements of conductivity as a function of strain (FIG. 9G) are done in a custom four-probe set up depicted in FIGS. 17A, 17C-17D. FIG. 17B shows a schematic of a sample before any stretching (as photographed in FIG. 17C), while FIG. 17E shows a schematic of the same sample after stretching and at a point before rupture (photographed in FIG. 17D). Measured resistance and applied tensile strain are recorded simultaneously by a video camera, and close up images of sample are photographed by a high-speed camera to calculate the thickness of sample at some strain level with the assumption that volume of sample was kept constant.

The temperature dependence of conductivity is measured by four probe method using a Magnetic Property Measurement System (MPMS) (Quantum Design, Inc., CA, USA). The MPMS is basically a cryogenic probe that integrates a superconducting magnet with a SQUID detection system and a temperature controller in a specially designed Dewar. These sophisticated configurations provide rapid precision measurements over a temperature range from 2 to 300 K.

Tensile Tests

Stress-strain curves are obtained by testing approximately 1 mm wide and 5-7 mm long rectangular strips of samples with a mechanical strength tester 100Q (TestResources Inc., MN, USA). Tests are performed at a rate of 0.01 mm/s for LBL films and 0.08 mm/s for VAF films with an approximate 111 N range load cell. Five samples are tested for each film.

The cyclic tensile test (FIG. 9G) is performed by a Servopneumatic Axial/Torsion Test Instrument with custom-made grips (EnduraTEC, MN, USA). Tests are performed at a rate of 0.01 mm/s.

UV/Vis Spectroscopy

Initial stages of LBL deposition are monitored using an 8453 UV-vis Chem Station spectrophotometer (Agilent Technologies, CA, USA). The reference for these measurements is ambient air and collected spectra of the adsorbed material are compared to UV-vis absorbance of a fresh, piranha-cleaned glass slide.

Ellipsometry

Thickness of initial assembly of LBL film is calculated using a BASE-160 Spectroscopic Ellipsometers (J. A. Woollam Co., Inc., NE, USA). The instrument is calibrated to the silicon wafer with a thin layer of silicon dioxide and the subsequent calculations are fitted using a Cauchy's model. The LBL film for ellipsometry is prepared on silicon wafers following the same procedure previously described as LBL film.

Thermogravimetric Analysis (TGA)

Samples are held in a platinum pan under an air atmosphere at a flow rate of 20 mL/min and analyzed on a Pyris 1 TGA (PerkinElmer, MA, USA). A temperature ramp is from 25° C. to 800° C. at 10° C./min.

Differential Scanning Calorimetry (DSC)

The DSC analysis is performed using a Q200 (TA Instruments, DE, USA). The sample is treated with the following heat/cool/heat method. The sample is first heated from 25° C. to 100° C. at a scan rate of 10° C./min. The heated sample is then cooled to −80° C., which is then reheated to 550° C. with the same rate.

Electron Microscopy

Scanning electron microscopy (SEM) images are obtained with an FEI Nova Nanolab dual-beam FIB and scanning electron microscope. The instrument is operated at 15 kV. Transmission electron microscopy (TEM) images are obtained with a JEOL 2010F Analytical Electron Microscope. HVEM images are obtained with the high voltage electron microscope (1,250 kV, JEOL, JEM-ARM 1300S). The specimens for HVEM imaging are prepared by using the focused ion beam (FIB, FEI, Quanta 3D FEG).

Atomic Force Microscopy (AFM)

Atomic force microscopy (AFM) imaging is performed with a Nanoscope III atomic force microscope (Digital Instruments/Veeco Metrology Group).

Small Angle X-Ray Scattering (SAXS)

X-ray scattering data are obtained with a Bruker NanoStar Small-Angle X-ray Scattering System equipped with Siemens Kristalloflex 770 X-Ray Generator, and Cu Kα Radiation (0.1542 nm) X-ray tube with Peak power of 1.5 kW on a Hi Star Area 2D detector with 1 min of exposure time.

Unless otherwise specified, LBL and VAF films had same gold contents in all the tests. The described measurements are performed under room temperature and relative humidity of 20-30% for both LBL and VAF composites.

Freestanding VAF films are measured to have an SEM thickness of 30±3.0 μm. Sheets made via LBL and VAF techniques both had unmistakable metallic appearance (FIGS. 6A-6D). FIGS. 6E-6H show scanning electron microscopy (SEM) images of 1×LBL and 1×VAF at the surface and within a cross-section. The designation n×LBL indicates that the composite material has "n" distinct layers and was formed in a layer-by-layer process described above, while n×VAF is a composite material having "n" distinct layers formed by vacuum assisted flocculation process also described above. Thus, FIGS. 6E-6H show a comparison of two embodiments of single layer composite materials formed in accordance with the present teachings (6E-6F showing the 1×LBL on a surface and cross-sectional view and 6G-6H showing 1×VAF on a surface and cross-sectional view). FIGS. 6I-6L show SEM images of cross-sections of comparative embodiments of a consolidated or laminated five layer (5×VAF) stack made by a layer-by-layer process according to certain aspects of the present disclosure (FIGS. 6I-6J) as compared to a consolidated or laminated five layer (5×VAF) stack made by a vacuum assisted flocculation process according to certain aspects of the present disclosure (FIGS. 6K-6L). The LBL and VAF composites are made to have same gold content, 21.7 vol. % (87.7 wt. %) (FIG. 7).

FIGS. 4A-4B show the dependence of thickness of films of stretchable electrically conductive composite materials comprising polyurethane (PU) polymer and gold nanoparticles (NP)–(PU/NP)$_n$, where n is number of deposition cycles each forming a distinct layer. As shown in FIG. 4A, PU (3P, 4P, 5P . . . ) and gold NPs (3A, 4A, 5A . . . ) layers with the same number correspond to one deposition cycle. Thickness change is measured by ellipsometry as the film is deposited via a layer-by-layer process on a silicon (Si) wafer as a substrate. Thickness of each layer is averaged based on three independent measurements. Average thickness increments for PU and Au NPs layers are 1.89 nm and 2.04 nm, respectively.

FIG. 4B shows UV-Vis absorbance spectra measured every 5th bilayers of (PU/NP)$_n$ LBL assemblies. The multilayers are formed on both sides of a glass substrate. The shift of the plasmon peak indicates from 515 nm (free Au NPs) to 650-660 nm for LBL films is indicative of strong plasmonic coupling and NP proximity to each other.

Theoretical values of percolation threshold (P$_c$) volume fractions for stretchable electrically conductive composite materials comprising nanoparticles (NP) assumes that (a) one nanoparticle (NP) takes a place of one lattice spot and (b) a cluster is connected only with nearest neighbors, for simple cubic lattice, body-centered cubic lattice, and face-centered cubic lattice are 0.3116, 0.246, and 0.198, respectively. Experimental P$_c$ may be compared to theoretical P$_c$ for dense face-centered cubic packing of particles equal to 19.8 vol. % (FIGS. 8A-8D). Other experimentally determined values of percolation threshold (P$_c$) for LBL and VAF films are 16.2 vol. % and 17.5 vol. %, respectively (FIG. 9A). Thus, experimental P$_c$ may be compared to theoretical P$_c$ for dense face-centered cubic (FCC) packing of particles equal to 19.8 vol. %. Lower-than-theory P$_c$ of the NP composites indicates that formation of percolating pathways in these composites is more efficient than in classical FCC lattices.

FIGS. 14A-14E show charge transport in stretchable electrically conductive composite materials in accordance with certain aspects of the present teachings. Three different conduction mechanisms are possible between neighboring gold nanoparticles (Au NPs): (a) direct contact; (b) variable-range hopping and (c) tunneling. The relative contribution of hopping and tunneling mechanisms depends on the shape of the barrier, the separation of the sites and thermal energy. Dependence of conductivity on temperature provides a reliable criterion by which conduction mechanism that dominates the samples can be unveiled. FIG. 14A is a schematic showing potential conduction behavior mechanisms in polyurethane-gold nanoparticle composites. This includes direct contact between nanoparticles, electron tunneling, and/or electron hopping. Equations for variable-range hopping and tunneling mechanisms are $$\sigma_{Hopping} = \sigma_0 \cdot \exp\left(-\frac{A}{T^{\frac{1}{4}}}\right)$$

for electron hopping and $$\sigma_{Tunneling} = \sigma_0 \cdot \exp\left(-\frac{B}{T^{\frac{1}{2}}}\right)$$

or for electron tunneling.

Fitting the equations for variable-range hopping and tunneling conduction mechanism demonstrate that electron transfer mechanism in LBL and VAF stretchable conductors prepared in accordance with certain aspects of the present teachings is governed neither by hopping nor by tunneling. FIGS. 14B and 14C plots of ln σ vs. $T^{-1/4}$ and $T^{-1/2}$ from data points of 1×LBL film (FIG. 9F), respectively. FIGS. 14D and 14E show plots of ln σ vs. $T^{-1/4}$ and $T^{-1/2}$ from data points of 1×VAF film (FIG. 9F), respectively. The plots of ln σ vs. $T^{-1/4}$ and $T^{-1/2}$ drawn from data points from FIG. 9F with equations above for tunneling and hopping did not conform to expected linear dependence.

To transition to fully macroscopic materials as-made LBL and VAF free-standing films separated from the substrates are compressed or laminated into stacks, as discussed above in the context of Example 3. Thus hot pressing of 3-10 freestanding layers or sheets together at 120° C. and pressure of 20 MPa for 1 hour reveals a high degree of consolidation (FIGS. 6I-6L). The laminated samples of five sheets are denoted, for instance, as 5×LBL or 5×VAF and have thicknesses of 6.5±0.7 μm and 110±10 μm, respectively (SEM).

LBL and VAF films have different properties for the same gold contents. As shown in FIGS. 8A-8D, distribution of nanoparticles within the polymer is distinct for each type of formation, although both types of formation provide distinct advantages and superior stretchable electrically conductive composite materials, as compared to conventional stretchable conductors. LBL composites have better dispersed nanoparticles NP (FIGS. 8A-8B and 9H-9J) leading to more efficient conducting pathways than VAF composites in which nanoparticles NPs are more aggregated (FIGS. 8C-8D and 9K). Simultaneously, the presence of larger PU domains appears to result in higher stretchability of VAF composites (FIGS. 9D and 9E). The freestanding 1×LBL and 1×VAF have conductivities of 6,800 S cm$^{-1}$ and 510 S cm$^{-1}$ and they could be stretched to 16% and 75%, respectively. As noted above, composite films formed by either layer-by-layer or vacuum assisted flocculation in accordance with certain aspects of the inventive technology, provide new materials with high stretchability and conductivity that are of significant technological importance.

Moreover, lamination increases conductivity of both types of films (FIG. 9B) and considerably improves stretchability (FIGS. 9C-9D). The conductivity of 5×LBL and 5×VAF composites is 11,000 S cm$^{-1}$ and 1,800 S cm$^{-1}$ (FIG. 9B) for tensile strain ($\in$)=0%. A maximum tensile strain ($\in_{max}$) for 5×LBL and 5×VAF is 115% and 486%, respectively (FIGS. 9C and 9D). The conductivity of 5×LBL and the stretchability of 5×VAF are believed to be the highest achieved for composite materials. As expected, the conductivity of LBL and VAF composites decreases with the increase of $\in$. 60% strain results in a 2.5 times reduction of conductivity to 3,500 S cm$^{-1}$ for a 5×LBL stack assembly and 4.2 times reduction to 210 S cm$^{-1}$ for 5×VAF stack assembly. 110% strain results in as little as 3.5 times reduction to 2,400 S cm$^{-1}$ for 5×LBL and a 9.4 times reduction to 94 S cm$^{-1}$ for 5×VAF (FIG. 9E). FIGS. 10C-10D show resistance over 10,000 stretching cycles for 1×LBL and 1×VAF composite layers. However, the conductivity values on the high-strain are slightly or considerably greater than similar values for CNT-based materials despite much smaller aspect ratio of NPs. Moreover, it is believed that no previous composites have displayed a conductivity of 35 S cm$^{-1}$ at strains of 480% (which occurs for 5×VAF). Additionally, anisotropy is also minimal. While being completely isotropic without stress, both NP composites became slightly anisotropic only after as many as 10,000 cycles at 5% strain (FIGS. 10A-10B).

How the inventive composite materials retain the capability to efficiently transport electrons at very high deformations is explored herein. First, nanoparticles (NPs) are capable of self-assembling in solution into chains. Atomic force microscopy (AFM), SEM, and transmission electron microscopy (TEM) images (FIGS. 9H-9J) indicate that NPs in composites formed by layer-by-layer processes (LBL) in accordance with certain aspects of the present disclosure produce chains of 20-40 NPs as being deposited. Such chains can behave similarly to high aspect ratio nanocomponents, while reducing percolation threshold ($P_c$) and displaying high conductance similar to bulk gold. Initially, it was hypothesized that this ability of NPs to self-assemble at the time of LBL deposition could be the cause of such unusual combination of properties. However, no evidence for NP chain formation was found in the bulk from SAXS data immediately after deposition at 0% strain (FIGS. 11A, 11C, 11F(1)-(2)) or in high voltage electron microscopy (HVEM) study (FIGS. 12A-12B) for LBL-formed and VAF-formed composite materials.

Then, it was hypothesized that while being almost disorganized initially, the NPs can self-organize under stress. Some elements of self-organization are seen for low filler concentrations and high aspect ratio nanomaterials. Indeed, stress-induced NP organization is observed in both LBL-formed and VAF-formed composites from SAXS data and SEM images (FIGS. 11A-11E and 11G-11N, showing different strain levels). At higher elongation, 50% of strain, the well-developed hourglass-shaped scattering pattern is observed in the SAXS data (FIGS. 11B, 11D, and 11E), indicating that the NPs are preferentially organized along the stretching direction as shown in the SEM images (FIGS. 9G and 9K). Intensity of the diffraction peak at q=0.045 Å$^{-1}$ also substantially increased after 50% of stretching for both 5×LBL and 5×VAF films (FIG. 9F). Unlike other stress-induced composite reorganization, beam patterns and intensity plots of SAXS data developed upon stretching disappeared when the tension is released. The self-organization NP patterns observed here are remarkably different from any other patterns observed before in either solutions or solids.

To highlight the nanoparticle (NP) patterns in the stretchable electrically conductive composite materials formed in accordance with certain aspects of the present disclosure, focused ion beam (FIB) milling is applied to a depth of 1-2 μm. SEM images of such samples remaining under strain of 110% for 5×LBL and 200% for 5×VAF reveal cellular self-organized patterns with characteristic dimensions of 1-5 μm (FIGS. 11I and 11M). These distinct NP networks can be the result of local phase separation of NPs dispersed in the polymer under high strain. Importantly, when the tension is released, these cellular networks under stress are not observed even after five consecutive stretches meaning NP networks are reconfigurable (FIGS. 11J and 11N). However, slight irreversible reconstruction of the material does occur, leading to the formation of the bands of the NPs running perpendicularly to the stress direction on the surface and the decreased stiffness (FIGS. 13A-13D).

With a 5% of strain, (the elastic limit of composites is regarded to be less than 10% of strain) films are repetitively stretched to observe changes of conductivity with deformation cycling. Interestingly, conductivity after 5,000 cycles increased substantially by 1.7 times for 1×LBL and 1.5 times for 1×VAF (FIG. 9G). Resistance of 1×LBL and 1×VAF after 10,000 cycled films measured parallel and perpendicular to the stretching direction also confirms gradual internal rearrangement of NPs. Resistances in both directions decrease, but that in the parallel direction decreased more than in the perpendicular direction. SAXS data on 10,000 cycled 1×LBL and 1×VAF also confirmed reorganization of NPs (FIGS. 10E and 10F).

While not limiting the present disclosure to any particular theory, the unexpectedly high conductivity found in stretchable electrically conductive nanoparticle-based composites in accordance with the inventive technology appears to be explained by self-organization of NPs making high density percolating pathways through cellular networks. The dynamic nature of these conductive pathways allows them to reconstruct and adapt to the strain as well as to the direction of the deformation. Importantly, the mobility of the matrix is also retained, which makes high stretchability possible.

Charge transport is also studied herein. Fitting temperature dependence of conductivity in a range of temperatures from 2 to 300 K (FIG. 9F) with variable-range charge transport equations reveals clearly metallic behavior via direct nanoparticle contact (see FIG. 9F and FIGS. 14A-14E), while that in the stretchable conductors from CNTs semiconducting behavior and hopping electron transport. Importantly, stretchable electrically conductive composites in accordance with the inventive technology comprising gold nanoparticles have high electron mobility: 1.75×10$^{-4}$ m$^2$ V$^{-1}$ s$^{-1}$ for 1×LBL and 5.45×10$^{-5}$ m$^2$ V$^{-1}$ s$^{-1}$ for 1×VAF. Carrier concentrations of 1×LBL at 300 K, 5.83×10$^{28}$ m$^{-3}$ approach that of gold, 5.90×10$^{28}$ m$^{-3}$ (FIGS. 15A-15B). Stretchable electrically conductive composites in accordance with the inventive technology comprising gold nanoparticles exhibiting metallic behavior are widely useful in many applications, including curvilinear conductive patches forming conformal interface with different organs (brain, heart, muscles) and novel consumer electronic devices.

Example 4

In this example, stretchable composite chiral plasmonic films are formed by a layer-by-layer process according to certain variations of the present disclosure. The reversibly tunable chiroptical thin films are composed of achiral building blocks, namely zero-dimensional gold nanoparticles (Au NPs, having an average particle size diameter of 13.0±0.3 nm), and a polyurethane (PU) polymer (See FIGS. 2A and 3B). These plasmonic nanostructures are prepared by layer-by-layer (LBL) assembly method. As discussed above, LBL assembly provides precise control when forming nanoscale structures, including making virtually defect-free structures via homogeneously distributed nanoparticles (NPs), which facilitates stable circular dichroism (CD) spectra response. LBL assembly also makes it possible to use a high fraction or amount of nanoparticle (NP) fillers, which in certain aspects, is important for obtaining high chiroptical properties in a material.

To induce homochirality to stretchable composite chiral plasmonic film in accordance with certain variations of the present disclosure, a pre-twisted substrate of elastic poly (dimethylsiloxane) (PDMS) is used, where clockwise and counterclockwise twisting along the x-axis for left-handed (LH) and right-handed (RH) is shown on the left and right sides in the FIGS. 18A-18B, respectively.

The elastic substrates are first prepared of polydimethylsiloxane (PDMS). PDMS (Dow Corning Sylgard 184; having a ratio of base to crosslinker, 10:1 by mass) is poured, mixed, and degassed in petri dish. Curing of the material is conducted in an oven at 70° C. for approximately 6 hours to produce PDMS membranes that are 0.5 mm thick. Then the membranes are cut into strips of 10 mm (width)×45 mm (length) as shown in FIG. 18A. To prepare chiroptical thin films, the following steps are taken. Strips of the PDMS are twisted to in a clockwise direction or a counterclockwise direction along the x-axis and fixed using clamps for LH and RH samples, respectively (FIGS. 18B and 23). Next, the surface of PDMS is activated for 30 min by UV Ozone cleaner (Model no. 342, Jelight Company, CA, USA) to modify the hydrophobic surface of PDMS with hydrophilic functionalities.

Polyurethane (PU) and gold nanoparticles (Au NPs) are prepared as follows. An as-received cationic polyurethane aqueous dispersion (30 vol. %, molecular weight (MW) of approximately 92,000, Hepce Chem. Co., South Korea) is used after diluting to 1 vol. % solutions in deionized (DI) water. Gold(III) chloride trihydrate, sodium citrate tribasic dihydrate (Sigma-Aldrich) are used as received. Citrate stabilized Au NPs with a diameter of about 13±0.3 nm are synthesized as described above in Example 1.

As-activated twisted-PDMS strips are dipped into a 1 vol. % solution of PU, for 5 min, rinsed with DI water for 1 min and gently dried with compressed air. Then they are dipped into a dispersion of concentrated Au NPs (as described above in Example 1), for 20 minutes, rinsed for 1 minute, and again dried with compressed air. Electrostatic attraction serves as a reasonable driving force for deposition. This one cycle deposition constitutes one layer pair of PU and Au NPs.

Five layer pairs of positively charged PU and negatively charged Au NPs, citrate-stabilized, are sequentially deposited (FIGS. 18B-18C, 2A-2B, and 3B). For the measurements of chiroptical properties, the samples are relaxed to be flat from a twisted state (FIG. 18D). See FIG. 23 for designation of sides of a sample and Cartesian coordinates used. A "crack-side" is opposite of "buckle-side" and the same designations are applied to all right-handed (counter clockwise) chirality. All parameters are defined to the right-handed Cartesian coordinate system, with the z-axis directed perpendicular to the buckle-side of the film. Optimized chiroptical properties are acquired after deposition of five layer pairs. Five layer pairs had thickness of 43 nm on silicon wafer by ellipsometry (FIG. 22).

As noted above, TEM images are obtained with a JEOL 2010F Analytical Electron Microscope and thickness of the initial assembly of the LBL film is calculated using the BASE-160 Spectroscopic Ellipsometer (J. A. Woollam, USA). Calculations are fitted using a Cauchy's model. The LBL film for ellipsometry is prepared on silicon wafers following the same procedure as described for the LBL film. Circular dichroism (CD) spectra are obtained by Jasco J-815 CD spectrometer. AFM (Atomic Force Microscope) images are obtained by Veeco Dimension Icon AFM and Bruker multimode AFM with ScanAsyst mode. CD spectra are simulated by computational simulations performed with wave-optics module embedded in COMSOL multiphysics. To reduce resources and costs on computational simulation, the geometry is simplified as one single lined array of gold nanoparticles without glass substrate. Details of geometrical parameters of models are shown in Table 1.

TABLE 1

Dimension of twisted helix measured from AFM images.

| | Left Handed (LH) Chirality | |
|---|---|---|
| | 0% stretching (nm) | 50% stretching (nm) |
| Width (w) | 711 ± 172 | 495 ± 79 |
| Height (h) | 75 ± 29 | 133 ± 47 |
| Length (l) | 479 ± 48 | 407 ± 38 |

Medium surrounding gold nanoparticles is set as air (∈=1). The optical constants of gold are taken from Johnson et al., "Optical Constants of the Noble Metals," *Physical Review B* 6, 4370-4379 (1972), incorporated herein by reference. Simulated CD is calculated from subtraction of cross-section extinction of left-handed circularly polarized light (LCP) to right handed circularly polarized light (RCP). CD=extinction of LCP−extinction of RCP, where cross-section extinction is a sum of cross-section absorption and cross-section scattering.

Chiroptical properties of as-prepared samples are measured for both forward (F or FLP) and backward (B or BLP) light propagation directions, corresponding to positive and negative z-direction, respectively (Coordinates are shown in FIG. 23). For backward light propagation, samples are rotated 180° to the y-axis. F-LH: Forward light propagation to Left-Handed (counter-clockwise chirality) sample, F-RH: Forward light propagation to Right-Handed (clockwise chirality) sample, B-LH: Backward light propagation to Left-Handed (counter-clockwise chirality) sample, and B-RH: Backward light propagation to Right-Handed (clockwise chirality) sample.

Chiroptical properties at their peak (wavelength in the parentheses) are as follows: CD value of 65.7 mdeg (670 nm) and −79.7 mdeg (667 nm) for F-LH and F-RH, −49.5 mdeg (630 nm) and 67.0 mdeg (635 nm) for B-LH and for B-RH (FIGS. 18E-18F and 19A-19D), anisotropy factor, g-factor, of 0.0027 (685 nm) and −0.0032 (687 nm) for F-LH and F-RH, and −0.0017 (630 nm) and 0.0023 (635 nm) for B-LH and for B-RH, respectively, (FIGS. 24A-25B). FIG. 20 shows intrinsic properties for left-handed (LH) embodiments, including CD signals to rotations for 0% and 50% stretching levels.

Surprisingly chiroptical properties are remarkably tunable by uniaxial mechanical stretching from 0% to 50% (stretching direction is indicated in FIG. 18D by a double arrow). Under forward light propagation, chiroptical properties are significantly amplified: CD increased by ×6.6 and ×5.4 (FIG. 18E) and g-factor increased by ×10.0 and ×9.0, for LH and RH, respectively, with small blueshift of <10 nm (FIG. 24A). Under backward light propagation, chiroptical properties are substantially blueshifted: peak of CD blueshifted by 49 nm and 66 nm (FIG. 18F) and peak of g-factor blueshifted by 59 nm and 73 nm for LH and RH, respectively, with increase of any spectra of less than ×4.6 (FIG. 24B). Absorbance decreased accordingly upon the stretching (FIG. 25). CD signals are typical bisignate dip-peak shape for F-LH and flipped over to be peak-dip shape for F-RH. CD of dispersed NPs on flat PDMS did not reveal any chiroptical responses within the wavelength range of interest (FIGS. 21A-21B show control experiments of chiroptical properties (CD and absorbance) of various materials, including 5 layer pairs on PDMS at 0% and 50% strain, dispersions of PU in water, Au NPs in water, PDMS only at 0% and 50% strain, a layer of PU deposited on a left handed film, a layer of PU deposited on a right handed film, a layer of AuNPs on a left handed film, and a layer of AuNPs on a right handed film).

As shown in FIGS. 24A-24B and 25, peak centers located at the plasmonic resonance wavelength of gold around 660-680 nm for forward light propagation at various strain levels, which are at much higher regions than those previously reported, and this is due strong plasmonic coupling from highly concentrated NPs by LBL assembly.

G-factor is often used as a measure to compare optical activities of chiral systems. Many examples showed high g-factors: 0.022 from Au NPs dispersed in chiral polymer template, 0.025 from helically arranged metallic core-shell structures by DNA-origami, <0.04 from resonance coupling of achiral gold nanostructure with chiral molecules, and about 0.35 from evaporated metallic NPs onto helically shaped dielectric templates. G-factor is about 0.029 (for 50% RH, FIGS. 24A-B). The stretchable composite material used as chiral plasmonic films with such optical activities are made from building blocks of minimal aspect ratio and did not have support from inherently helical templates, chiral molecules, or other materials with high polarizability, such as silver.

Also importantly, chiroptical properties are virtually reversible upon 50% stretching. For true CD, value at their maxima decreased reversibly by 15% for the strain of 50% up to five stretching cycles, and then showed stable response (FIG. 26B). Such desired chiroptical responses can be reliably obtainable in the visible electromagnetic spectrum range and thus have vastly applicable uses, including practical engineering applications, such as sensors.

FIGS. 26A-26B show CD signals excluding linear effects. FIG. 26A shows true CD spectra under various strain levels of 0%, 10%, 25%, and 50%, respectively. Designations (1)-(4) are for left-handed (LH) chirality and (5)-(8) for right-handed chirality. FIG. 26B shows true CD values at their peaks for five cycles of reversible stretching to 50% and releasing to 0%.

According to the dipole theory, CD signals become stronger when the particles are either larger or arranged in a tighter structure. Thus, under the same size of NPs, tunability of CD can come from change of arrangement of nanoparticles into a tighter structure. A reversible CD means that arrangement of nanoparticles is reversible and can be transitioned between loose (nanoparticles having maximal spacing there between) and tight structures (nanoparticles having minimal spacing there between). As noted above, nanoparticles in the stretchable composite chiral plasmonic materials have high mobile freedom to be self-organized into desired geometries by mechanical stress in the solid-state.

Next, morphology of the metallic nanostructures is examined using atomic force microscopy (AFM) to understand structural changes of the assembled nanoparticles in the stretchable composite chiral plasmonic films. FIGS. 28A-28L show a series of schematic diagrams depicting the change in morphology of NPs in layers on PDMS substrates with strain, as well as corresponding AFM images. See also, FIGS. 27A-27L. An as-deposited film exhibits homogeneously distributed nanoparticles NPs without any buckles. However, thin film released from twisting (FIG. 18D) shows diagonally symmetric buckled morphology for LH and RH (FIGS. 27A-27F and 28A-28F showing buckle side and FIGS. 27G-27L and 28G-28L for crack side). Out-of-plane buckling occurs as a balance of various parameters: stress (twist) applied to substrate, thickness of film, and stiffness of films and substrate.

The application of tensile stress made the buckles more oriented to it and to have higher amplitude and frequency (FIGS. 28C-28F and 27C-27F). From the AFM images, it can be seen that nanoparticles are aligned into mirror-symmetric twisted chains for LH and RH across the ridges of the buckles and those twisted chains of nanoparticles have increased height (75±29 nm at 0% to 133±47 nm at 25%) and decreased width (711±172 nm at 0% to 495±79 nm at 25%) and length (479±48 nm at 0% to 407±38 nm at 25%), which are directly correlated to the shape change of buckles (FIGS. 25, 27A-27F, 28A-28F, and Table 1 for actual calculations of the dimensions). Twisted chains of NPs along with valleys of buckles for LH and RH with strains of 0% and 25% are compared and each handed image is non-superimposable to its counterpart.

Therefore, the LBL assembled and pre-twist induced stretchable composite chiral materials comprising nanoparticles are believed to be responsible for plasmonic coupling, including chirality or handedness and change of geometry, determined by highly mobile nanoparticles NPs stretching that are responsible for reversible change of chiroptical properties.

Simulations on twisted geometry at different strain levels are explored here. Chiroptical properties of gold (Au) twisted chains are simulated with COMSOL multiphysics. Two different strain levels of 0% and 50% are selected as representative cases. Geometry of each model is greatly simplified as a single lined array of gold nanoparticles (Au NPs) taken as a smallest repeating structural unit in the stretchable composite chiral plasmonic films of certain variations of the present technology. Geometries of left-handed (LH) chirality films with strain of 0% and 50% are presented in FIGS. 29A-29B, respectively.

In FIGS. 29A-29B, an illustrative schematic showing simplified geometry is depicted, where a plurality of nanoparticles 300 are helically organized and represent a stretchable chiral plasmonic composite having left handed chirality (LH) in accordance with certain aspects of the present disclosure under strains of 0%, and 50%. In FIG. 29A, a plan view of the helical strand of nanoparticles 300 before stretching (0% strain) has a distance ($d_O$) between respective nanoparticles 300, while the strand of nanoparticles 300 has a length ($l_O$). A side view below shows that the strand of nanoparticles 300 at a strain of 0% has a width ($w_O$) and a height ($h_O$). FIG. 29B shows the same helical strand of nanoparticles 300 under 50% strain, where a length $l_{50}$ is less than initial length $l_O$ and a width $w_{50}$ is less than initial width $w_O$. However, height $h_{50}$ in the 50% strained sample is greater than $h_O$ in the 0% sample. In case of right handed (RH) chirality models, geometries are simply mirrored to those in LH models.

Geometrical parameters of each model are obtained from AFM images (FIGS. 28A-28L and 27A-27L). Width, height, and length of unit rectangular cells containing Au NP arrays are tabulated (as discussed above and set forth in Table 1). An average distance between centers of nanoparticles is obtained from SAXS measurement.

FIGS. 29C-29D show theoretical chiroptical activities of chiral films under strains of 0%, and 50% of CD spectra and G-factor, respectively. Simulated CD spectra and g-factors are shown in FIGS. 29C-29D, respectively. The left-handed (LH) chirality sample is designated (1—50% strain) and (2—0% strain) and right-handed (RH) chirality sample is designated (3—0% strain) and (4—50% strain). 0% of LH has a dip-peak shaped spectrum with small negative peak at 530 nm and large positive peak at 570 nm. When LH is stretched to 50%, amplitude of both peaks is increased about 2 times and red-shifted about 5 nm. RHs of 0% and 50% have same results but with opposite sign. Comparing the simulated results to experiments in FIG. 18E, overall trends are similar, but broadening and redshift of peaks dominantly appeared in experimental CD results. This is believed to be due to strong coupling effects originating from more proximate Au NPs existing in real samples, whereas only single array of Au NPs is accounted for in simulation. Also blue-shifted spectra in simulated results of g-factor can be explained in the same way, compared to experimental results. Consequently, the simulation results support the theory raised in the experiments that the direction of twisting in macro-scale, clockwise or counter-clockwise, can generate twisted alignment of nanoparticles (e.g., Au NPs), thus controlling the sign of CD spectra and intensifying chiroptical response of CD signals by stretching.

Example 5

In this example, a medical device comprising a coating comprising stretchable electrically conductive composite material according to certain aspects of the present technology is formed. Angioplasty balloons from Interface Catheter Solutions (CA, USA) are used. Polyurethane (30 vol %, MW of approximately 92,000) from Hepce Chem Co., (South Korea) is diluted to 1 vol. % solution in deionized (DI) water. Gold(III) chloride trihydrate and sodium citrate tribasic dihydrate (Sigma-Aldrich) are used as-received.

Citrate-stabilized Au NPs with an average particle size diameter of 13±0.3 nm are synthesized as follows. Gold(III) chloride trihydrate (180.0 mg, 0.458 mmol) is added to ultrapure DI water (950 mL) in a 1 L glass beaker equipped with a magnetic stir bar. The mixture is heated to a boil under vigorous stirring, followed by additional heating for 20 minutes. Subsequently, 50 mL of 34 mM sodium citrate solution is added to the mixture. The aqueous solution is heated for 20 minutes followed by cooling to room temperature.

The solution is further concentrated to be used as dipping solution for LBL films. For the concentration process, the as-made aqueous Au NPs dispersions are transferred into 50 mL centrifuge tubes and concentration of the solutions is increased via Sorvall Legend Mach 1.6R (Thermo scientific, MA, USA) at the speed of 10,000 rpm for 1 hour. Less than 5 mL of concentrated of Au NPs solution settled at the bottom of the tube. Supernatant of 45 mL is removed by suction pipettes, while taking special care to prevent disturbing of the sedimented nanoparticles. Finally, the resultant NPs are collected for use in the LBL process.

The as-received balloons are first dipped into a 1 vol. % solution of positively charged PU, for 5 minutes, rinsed with DI water for 1 minute and gently dried with compressed air. Then, the balloons are sequentially dipped into a dispersion of negatively charged and concentrated Au NPs, for 20 minutes, rinsed for 1 minute, and again dried with compressed air. This single deposition cycle constitutes one layer pair of PU and Au NPs. The coated surface of the angioplasty balloon became highly conductive after deposition of 80 layer pairs and had thickness of about 400±40 nm. Electrostatic attraction is believed to be a reasonable driving force for deposition. Two of the angioplasty balloons formed in this process are shown in FIG. 31.

Regardless of the application, fundamentally the stretchable electrically conductive composites of the inventive technology, which may comprise gold nanoparticles (such as those comprising high Au NP loading), display previously unknown high-stress reorganization processes into cellular NP networks, which are believed to be responsible for the unexpectedly high conductivity while avoiding matrix stiffening. To some degree such restructuring imitates the behavior of atoms in liquid metals, while retaining structural integrity and strong bonding. They offer greater matrix mobility and hence greater overall elasticity than entangled CNTs and nanowires.

For example, when the electrically conductive composite is stretched, nanoparticles distributed within the polymeric matrix can adopt a different configuration that will still facilitate electron transport. The dynamics of such stretchable electrically conductive composites enables developing new strategies for combining electrical and mechanical materials properties. In various aspects, the stretchable electrically conductive composites according to the present disclosure are flexible, lightweight, and highly conductive even when stretched. Thus, in accordance with various aspects of the present disclosure, stretchable electrically conductive composites comprising electrically conductive nanoparticles are particularly suitable for use in applications such as advanced medical devices or implants, including neurosynthetic implants, stretchable or flexible electronics, including stretchable plasmonic devices and optical filters, flexible, lightweight solar cells and batteries, electronic paper and electronic textiles, conductive membranes, or any other application where conductive materials that are elastic are required. As appreciated by those of skill in the art, when the stretchable electrically conductive composites are used in implantable medical devices or implants, the materials selected for the polymer and nanocomposites are preferably biocompatible.

All possible combinations discussed and enumerated above and herein as optional features of the inventive materials and inventive methods of the present disclosure are specifically disclosed as embodiments. In various aspects, the present disclosure contemplates a stretchable composite material comprising an elastic polymer having a maximum strain of greater than or equal to about 50%; and a plurality of conductive nanoparticles. The stretchable composite material exhibits an electrical conductivity of greater than or equal to about 500 Scm$^{-1}$ at a tensile strain of greater than or equal to about 15%. Also specifically disclosed are combinations including this stretchable composite material optionally with any one or any combination of more than one of the enumerated features (1)-(7).

The stretchable composite material of the first embodiment optionally has any one or any combination of more than one of the following features: (1) a plurality of conductive nanoparticles having a maximum dimension of less than or equal to about 100 nm; (2) a plurality of conductive nanoparticles selected from the group consisting of: gold, silver, copper, nickel, iron, carbon, platinum, silicon, CdTe, CdSe, CdS, HgTe, HgSe, HgS, PbTe, PbSe, PbS, MoS2, FeS2, FeS, FeSe, and combinations thereof; (3) a plurality of conductive nanoparticles comprising gold nanoparticles; (4) a plurality of conductive nanoparticles present at greater than or equal to about 15 volume % to less than or equal to about 30 volume % of the total volume of the stretchable composite material; (5) a polymer comprising polyurethane; (6) a stretchable composite material exhibiting an electrical conductivity of greater than or equal to about 510 Scm$^{-1}$ at a tensile strain of 0%, where a maximum tensile strain of the stretchable composite material is greater than or equal to about 75%; and/or (7) a stretchable composite material exhibiting an electrical conductivity of greater than or equal to about 6,800 Scm$^{-1}$ at a tensile strain of 0%, where a maximum tensile strain of the stretchable composite material is greater than or equal to about 15%.

In other aspects, the present disclosure contemplates a stretchable composite material that comprises a plurality of laminated layers, where each layer of the plurality comprises an elastic polymer having a maximum strain of greater than or equal to about 50% and a plurality of conductive nanoparticles. The stretchable composite material exhibits an electrical conductivity of greater than or equal to about 1,700 Scm$^{-1}$ at a tensile strain of 0%, where a maximum tensile strain of the stretchable composite material is greater than or equal to about 110%.

Also specifically disclosed are combinations including this stretchable composite material optionally with any one or any combination of more than one of the enumerated features (8)-(19). The stretchable composite material of this embodiment optionally has any one or any combination of more than one of the following features: (8) a plurality of conductive nanoparticles having a maximum dimension of less than or equal to about 100 nm; (9) a plurality of conductive nanoparticles selected from the group consisting of: gold, silver, copper, nickel, iron, carbon, platinum, silicon, CdTe, CdSe, CdS, HgTe, HgSe, HgS, PbTe, PbSe, PbS, MoS$_2$, FeS$_2$, FeS, FeSe, and combinations thereof; (10) a plurality of conductive nanoparticles comprising gold nanoparticles and a polymer comprising polyurethane; (11) a stretchable composite material comprising at least five laminated layers; (12) a stretchable composite material having a maximum tensile strain of greater than or equal to about 115%; (13) a stretchable composite material having a maximum tensile strain of greater than or equal to about 485%; (14) a stretchable composite material that exhibits an electrical conductivity of greater than or equal to about 1,800 Scm$^{-1}$ at a tensile strain of 0%; (15) a stretchable composite material exhibiting an electrical conductivity of greater than or equal to about 11,000 Scm$^{-1}$ at the tensile strain of 0%; (16) a stretchable composite material exhibiting an electrical conductivity of greater than or equal to about 210 Scm$^{-1}$ at the tensile strain of greater than or equal to about 60%; (17) a stretchable composite material exhibiting an electrical conductivity of greater than or equal to about 3,500 Scm$^{-1}$ at the tensile strain of greater than or equal to about 60%; (18) a stretchable composite material exhibiting an electrical conductivity of greater than or equal to about 94 Scm$^{-1}$ at the tensile strain of greater than or equal to about 110%; and/or (19) a stretchable composite material exhibiting an electrical conductivity of greater than or equal to about 2,400 Scm$^{-1}$ at the tensile strain of greater than or equal to about 110%.

In other aspects, the present disclosure contemplates a method for forming a stretchable electrically conductive composite material. The method comprises applying a first charged material having a first polarity to a substrate having a second polarity opposite to the first polarity. Then, a second charged material having the second polarity is applied over the first charged material in a layer-by-layer process. The first charged material and the second charged material are distinct from one another and selected from a polymer and a plurality of conductive nanoparticles. The method further comprises removing the first charged material and the second charged material from the substrate. The first charged material and the second charged material together define at least one layer of a composite material that exhibits an electrical conductivity of greater than or equal to about 6,750 Scm$^{-1}$ at a tensile strain of greater than or equal to about 15%.

Also specifically disclosed are combinations including this method optionally with any one or any combination of more than one of the enumerated steps or features (20)-(22). The method for forming a stretchable electrically conductive composite material optionally has any one or any combination of more than one of the following steps or features: (20) forming a plurality of layers of the composite material by repeated sequential applying of the first charged material and the second charged material before the removing of the first charged material and the second charged material from the substrate; (21) forming a plurality of discrete independent layers which are subsequently assembled and laminated together; and/or (22) a first charged material is a positively-charged polyurethane and a second charged material is a plurality of gold nanoparticles having a negatively-charged surface layer.

In yet other aspects, the present disclosure contemplates an alternative method for forming a stretchable electrically conductive composite material. The method comprises introducing a first charged material having a first polarity into a suspension comprising a second charged material having a second polarity opposite to the first polarity. The first charged material comprises a polymer and the second charged material comprises a plurality of nanoparticles. The step of introducing the first charged material causes flocculation of moieties comprising the first charged material and the second charged material. The method comprises filtering the flocculated moieties from the suspension and drying the flocculated moieties. The dried filtered flocculated moieties together define at least one layer of a composite material that exhibits an electrical conductivity of greater than or equal to about 500 Scm$^{-1}$ at a tensile strain of greater than or equal to about 75%.

Also specifically disclosed are combinations including this method optionally with the following step or feature: (23) a first charged material is a positively-charged polyurethane and the second charged material is a plurality of gold nanoparticles having a negatively-charged surface layer.

In other aspects, the present disclosure contemplates a stretchable chiral plasmonic material. The plasmonic material comprises a twisted film comprising an elastic polymer having a maximum strain of greater than or equal to about 50% and a plurality of nanoparticles dispersed in the elastic polymer. The twisted film has either a left-handed chirality or a right-handed chirality based on a rotational direction of the twisted film. Further, the twisted film is capable of reversibly transitioning from a first twisted state to a second relaxed state to control chiroptical properties of the stretchable composite chiral plasmonic material.

Also specifically disclosed are combinations including this stretchable chiral plasmonic material optionally with any one or any combination of more than one of the enumerated features (24)-(27). The stretchable chiral plasmonic material of this embodiment optionally has any one or any combination of more than one of the following features: (24) a plurality of nanoparticles having a maximum dimension of less than or equal to about 100 nm; (25) a plurality of nanoparticles comprising a material selected from the group consisting of: gold, silver, copper, nickel, iron, carbon, platinum, silicon, CdTe, CdSe, CdS, HgTe, HgSe, HgS, PbTe, PbSe, PbS, $MoS_2$, $FeS_2$, FeS, FeSe, and combinations thereof; (26) an elastic polymer comprising polyurethane and a plurality of nanoparticles comprising gold nanoparticles; and/or (27) a plurality of nanoparticles are present at greater than or equal to about 15 volume % to less than or equal to about 30 volume % of the total volume of the stretchable composite chiral plasmonic material.

In yet other aspects, the present disclosure contemplates a method for forming a stretchable chiral plasmonic material comprising applying a first charged material having a first polarity to a twisted substrate having a second polarity opposite to the first polarity. The method further comprises applying a second charged material having the second polarity over the first charged material in a layer-by-layer process. The first charged material and the second charged material are distinct from one another and selected from a polymer and a plurality of nanoparticles. The method further comprises removing the first charged material and the second charged material from the twisted substrate. The first charged material and the second charged material together define a plasmonic film having either a left-handed chirality or a right-handed chirality based on a rotational direction of the twisted substrate.

Also specifically disclosed are combinations including this method optionally with any one or any combination of more than one of the enumerated steps or features (28)-(30). The method for forming a stretchable chiral plasmonic material optionally has any one or any combination of more than one of the following steps or features: (28) after the applying, permitting the plasmonic film to relax from a first twisted state to a second relaxed state to facilitate buckling of the plasmonic film; (29) forming a plurality of layers by repeated sequential applying of the first charged material and the second charged material before the removing of the first charged material and the second charged material from the twisted substrate; and/or (30) a first charged material is a positively-charged polyurethane and a second charged material is a plurality of gold nanoparticles having a negatively-charged surface layer.

In other aspects, the present disclosure contemplates a medical device comprising a stretchable electrically conductive composite material that comprises an elastic polymer having a maximum strain of greater than or equal to about 50% and a plurality of conductive nanoparticles. The stretchable electrically conductive composite material exhibits an electrical conductivity of greater than or equal to about 500 $Scm^{-1}$ at a tensile strain of greater than or equal to about 15%. Also specifically disclosed are combinations including this stretchable electrically conductive composite material optionally with any one or any combination of more than one of the enumerated features (31)-(41).

The stretchable electrically conductive composite material of the first embodiment optionally has any one or any combination of more than one of the following features: (31) a plurality of conductive nanoparticles having a maximum dimension of less than or equal to about 100 nm; (32) a plurality of conductive nanoparticles selected from the group consisting of: gold, silver, copper, nickel, iron, carbon, platinum, silicon, CdTe, CdSe, CdS, HgTe, HgSe, HgS, PbTe, PbSe, PbS, MoS2, FeS2, FeS, FeSe, and combinations thereof; (33) a plurality of conductive nanoparticles comprising gold nanoparticles; (34) a plurality of conductive nanoparticles present at greater than or equal to about 15 volume % to less than or equal to about 30 volume % of the total volume of the stretchable composite material; (35) a polymer comprising polyurethane; (36) a stretchable electrically conductive composite material exhibiting an electrical conductivity of greater than or equal to about 510 $Scm^{-1}$ at a tensile strain of 0%, where a maximum tensile strain of the stretchable composite material is greater than or equal to about 75%; (37) a stretchable electrically conductive composite material exhibiting an electrical conductivity of greater than or equal to about 6,800 $Scm^{-1}$ at a tensile strain of 0%, where a maximum tensile strain of the stretchable composite material is greater than or equal to about 15%; (38) a stretchable electrically conductive composite material serves as an electrode in the medical device; (39) a medical device is an inflatable balloon catheter that comprises a surface having stretchable electrically conductive composite material; (40) a medical device that is an inflatable balloon catheter that comprises a surface having a patterned stretchable electrically conductive composite material disposed on certain regions of the surface; and/or (41) a stretchable electrically conductive composite material capable of serving as one or more electrodes of the medical device.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A stretchable composite material comprising:
a plurality of consolidated laminated layers in contact with one another, wherein each layer of the plurality comprises an elastic polymer and a plurality of conductive nanoparticles, wherein the stretchable composite material exhibits an electrical conductivity of greater than or equal to about 1,700 $Scm^{-1}$ at a tensile strain of 0%, wherein a maximum tensile strain of the stretchable composite material is greater than or equal to about 400%.

2. The stretchable composite material of claim 1, wherein the plurality of conductive nanoparticles has a maximum dimension of less than or equal to about 100 nm and is selected from the group consisting of: gold, silver, copper, nickel, iron, carbon, platinum, silicon, CdTe, CdSe, CdS, HgTe, HgSe, HgS, PbTe, PbSe, PbS, MoS$_2$, FeS$_2$, FeS, FeSe, and combinations thereof.

3. The stretchable composite material of claim 1, wherein the plurality of conductive nanoparticles comprises gold nanoparticles and the elastic polymer comprises polyurethane.

4. The stretchable composite material of claim 1 comprising at least five laminated layers.

5. The stretchable composite material of claim 1, wherein a maximum tensile strain of the stretchable composite material is greater than or equal to about 450%.

6. The stretchable composite material of claim 1, wherein a maximum tensile strain of the stretchable composite material is greater than or equal to about 485%.

7. The stretchable composite material of claim 1, wherein the stretchable composite material exhibits an electrical conductivity of greater than or equal to about 1,800 Scm$^{-1}$ at the tensile strain of 0%.

8. The stretchable composite material of claim 1, wherein the stretchable composite material exhibits an electrical conductivity of greater than or equal to about 11,000 Scm$^{-1}$ at the tensile strain of 0%.

9. The stretchable composite material of claim 1, wherein the stretchable composite material exhibits an electrical conductivity of greater than or equal to about 210 Scm$^{-1}$ at the tensile strain of greater than or equal to about 60%.

10. The stretchable composite material of claim 1, wherein the stretchable composite material exhibits an electrical conductivity of greater than or equal to about 3,500 Scm$^{-1}$ at the tensile strain of greater than or equal to about 60%.

11. The stretchable composite material of claim 1, wherein the stretchable composite material exhibits an electrical conductivity of greater than or equal to about 94 Scm$^{-1}$ at the tensile strain of greater than or equal to about 110%.

12. The stretchable composite material of claim 1, wherein the stretchable composite material exhibits an electrical conductivity of greater than or equal to about 2,400 Scm$^{-1}$ at the tensile strain of greater than or equal to about 110%.

13. A stretchable composite material comprising:
a plurality of consolidated laminated layers in contact with one another, wherein each layer of the plurality comprises an elastic polymer and a plurality of conductive nanoparticles and at least one of the plurality of consolidated laminated layers comprises gold nanoparticles, wherein the stretchable composite material exhibits an electrical conductivity of greater than or equal to about 200 Scm$^{-1}$ at a tensile strain of 60%.

14. The stretchable composite material of claim 13, wherein the stretchable composite material exhibits the electrical conductivity of greater than or equal to about 3,500 Scm$^{-1}$ at a tensile strain of 60%.

15. The stretchable composite material of claim 13, wherein the stretchable composite material exhibits the electrical conductivity of greater than or equal to about 94 Scm$^{-1}$ at a tensile strain of 110%.

16. The stretchable composite material of claim 13, wherein the stretchable composite material exhibits the electrical conductivity of greater than or equal to about 2,400 Scm$^{-1}$ at a tensile strain of 110%.

17. The stretchable composite material of claim 13, wherein the plurality of conductive nanoparticles is present at greater than or equal to about 15 volume % to less than or equal to about 30 volume % of the total volume of the stretchable composite material and the elastic polymer comprises polyurethane.

18. The stretchable composite material of claim 13, wherein the plurality of consolidated laminated layers comprises at least five layers.

19. A medical device comprising the stretchable composite material of claim 13.

20. A medical device of claim 19 comprising an inflatable balloon, wherein the stretchable composite material is disposed on one or more regions of a surface of the inflatable balloon to serve as one or more electrodes.

21. A stretchable composite material comprising:
a plurality of consolidated laminated layers in contact with one another, wherein each layer of the plurality comprises an elastic polymer and a plurality of conductive nanoparticles and at least one of the plurality of consolidated laminated layers comprises gold nanoparticles, wherein the stretchable composite material exhibits an electrical conductivity of greater than or equal to about 7,000 Scm$^{-1}$ at a tensile strain of 0%, wherein a maximum tensile strain of the stretchable composite material is greater than or equal to about 15%.

22. The stretchable composite material of claim 21, wherein the stretchable composite material exhibits the electrical conductivity of greater than or equal to about 3,500 Scm$^{-1}$ at a tensile strain of 60%.

23. The stretchable composite material of claim 21, wherein the stretchable composite material exhibits the electrical conductivity of greater than or equal to about 11,000 Scm$^{-1}$ at a tensile strain of 0% wherein a maximum tensile strain of the stretchable composite material is greater than or equal to about 115%.

24. The stretchable composite material of claim 21, wherein the stretchable composite material exhibits the electrical conductivity of greater than or equal to about 94 Scm$^{-1}$ at a tensile strain of 110%.

25. The stretchable composite material of claim 21, wherein the stretchable composite material exhibits the electrical conductivity of greater than or equal to about 2,400 Scm$^{-1}$ at a tensile strain of 110%.

26. The stretchable composite material of claim 21, wherein the plurality of conductive nanoparticles is present at greater than or equal to about 15 volume % to less than or equal to about 30 volume % of the total volume of the stretchable composite material and the elastic polymer comprises polyurethane.

27. The stretchable composite material of claim 21, wherein the plurality of consolidated laminated layers comprises at least five layers.

28. A medical device comprising the stretchable composite material of claim 21.

* * * * *